(12) United States Patent
Simons et al.

(10) Patent No.: US 7,785,900 B1
(45) Date of Patent: Aug. 31, 2010

(54) GLUTATHIONE BEADS AND GST FUSION PROTEINS

(75) Inventors: Peter C. Simons, Albuquerque, NM (US); Larry A. Sklar, Albuquerque, NM (US); Eric R. Prossnitz, Albuquerque, NM (US); Angela Wandinger-Ness, Albuquerque, NM (US); Mathewos Z. Tessema, Albuquerque, NM (US); John C. Reed, Ranch Santa Fe, CA (US); Dayong Zhai, San Diego, CA (US)

(73) Assignees: STC.UNM, Albuquerque, NM (US); Sanford-Burnham Medical Research Institute, La Jolla, CA (US)

( * ) Notice: Subject to any disclaimer, the term of this patent is extended or adjusted under 35 U.S.C. 154(b) by 582 days.

(21) Appl. No.: 11/652,432

(22) Filed: Jan. 11, 2007

Related U.S. Application Data

(60) Provisional application No. 60/757,951, filed on Jan. 11, 2006.

(51) Int. Cl.
*G01N 33/543* (2006.01)
*G01N 33/53* (2006.01)

(52) U.S. Cl. .................. 436/523; 436/501; 436/506; 436/518; 436/524; 436/528; 435/7.1; 435/7.21; 422/50; 422/61; 424/9.1; 530/300; 530/350

(58) Field of Classification Search .................. None
See application file for complete search history.

(56) References Cited

OTHER PUBLICATIONS

Tessema et al. (Cytometry, May 2006, vol. 69A, No. 5, pp. 326-334).*

* cited by examiner

*Primary Examiner*—Lisa V Cook
(74) *Attorney, Agent, or Firm*—Henry D. Coleman; R. Neil Sudol; William J. Sapone

(57) ABSTRACT

The present invention relates generally to glutathione derivatized beads which are adapted for use in conjunction with glutathione-S-transferase fusion proteins (generally, GST fusion proteins, which contain a fluorescent label such as fluorescent green protein) for use in flow cytometry. The present invention also relates to methods for detecting and/or quantifying interactions between a GST fusion protein and their binding partners, in particular, labeled binding partners such as fluorescently labeled binding partners. By creating glutathione beads with an appropriate high or increased site density, disadvantages often associated with low affinity systems and quick off-rates in solution may be resolved to provide a workable system and method. Methods of identifying potential agonists, antagonists and regulator compounds of proteins fused to GST from libraries of compounds represents another aspect of the present invention.

37 Claims, 23 Drawing Sheets

A.

B.

C.

FIGURE 7 A and 7B
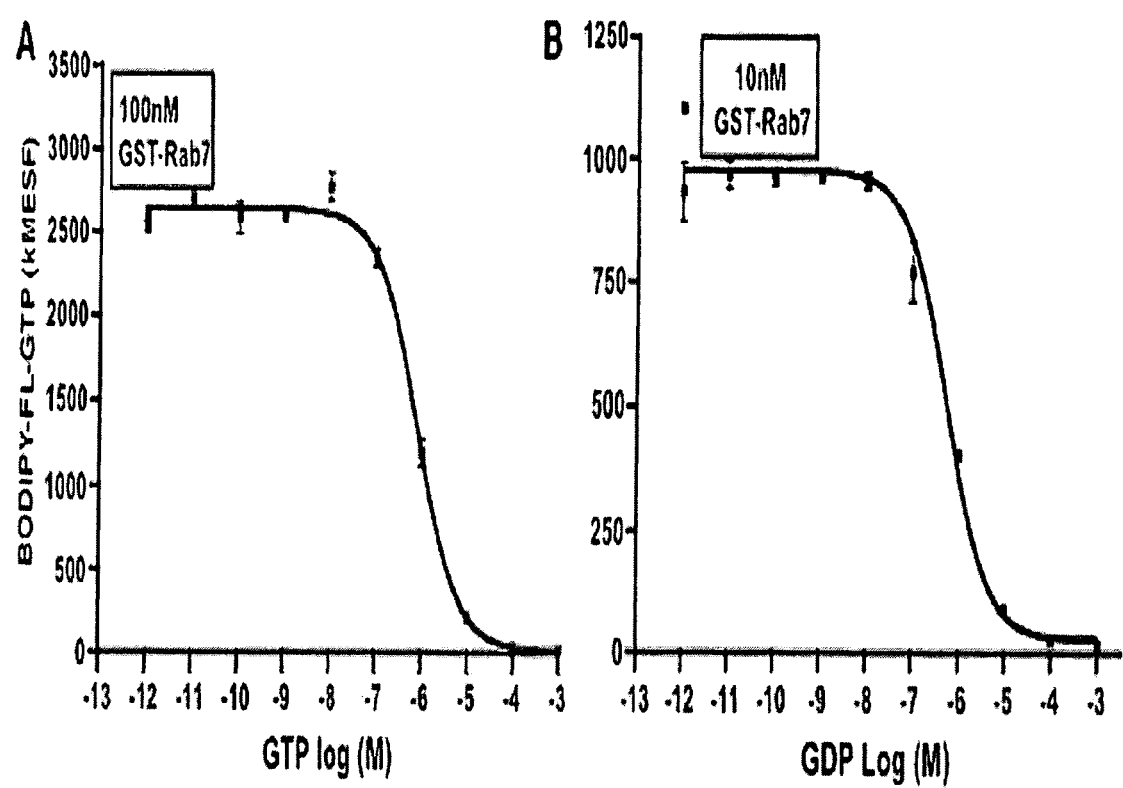

9A

9B

Fig. 1. Purification of GST-Bcl-2 proteins. 10 µg of each purified protein was analyzed by SDS-PAGE follow by Coumassie Blue staining. GST protein was used as control.

Fig. 2. FPA analysis of Bcl-2-family proteins using FITC-Bid BH3 peptide. Various concentrations of GST or GST-Bcl-2-famiily fusion proteins were incubated with 5 nM FITC-conjugated-Bid BH3 peptide in PBS [pH 7.4]. Fluorescence polarization (in milli-polars) was measured after 10 min.

Fig. 3. Competition assay analysis of green tea compound EGCG. 100 nM of GST-Bcl-2 fusion proteins were incubated with various concentrations of EGCG or control compound ECG ("C") for 2 min in PBS buffer in 50 uL. Then, 5 nM FITC-conjugated-Bid BH3 peptide was added, bringing final volume to 100 uL and final DMSO concentration to 1 %. Fluorescence polarization was measured after 20 min.

Microsphere Assay Assembly Schematic

18A

18B

Three ways to glutathione beads

Carbohydrate beads:

1. 0.3 M NaOH; 22°; 8 hrs;
   50% bis-epoxide
2. 100 mM glutathione; 40°;
   50 mM phosphate pH 7; 2 hrs Structure 1:

Amino-polystyrene beads:

1. 0.2 M Na₂CO₃; 40°; 2 hrs;
   50% bis-epoxide
2. 100 mM glutathione; 40°;
   50 mM phosphate pH 7; 2 hrs Structure 2:

Amino-polystyrene beads:

1. 50 mM phosphate, pH 7.5; 2 mM SMCC
   22°; 30 min
2. 20 mM glutathione; 40°;
   50 mM phosphate pH 7; 2 hrs Structure 3:

SEQUENCE LISTING

```
<160> NUMBER OF SEQ ID NOS: 7

<210> SEQ ID NO 1
<211> LENGTH: 14
<212> TYPE: PRT
<213> ORGANISM: Homo sapiens
<220> FEATURE:
<221> NAME/KEY: HELIX
<222> LOCATION: (2)..(10)
<223> OTHER INFORMATION: Unknown
<220> FEATURE:
<221> NAME/KEY: HELIX
<222> LOCATION: (12)..(12)
<223> OTHER INFORMATION: Unknown
<220> FEATURE:
<221> NAME/KEY: HELIX
<222> LOCATION: (13)..(13)
<223> OTHER INFORMATION: either Lys or Arg
<220> FEATURE:
<221> NAME/KEY: HELIX
<222> LOCATION: (14)..(14)
<223> OTHER INFORMATION: either His or Tyr

<400> SEQUENCE: 1

Lys Xaa Xaa Xaa Xaa Xaa Xaa Xaa Xaa Xaa Lys Xaa Xaa Xaa
1               5                   10

<210> SEQ ID NO 2
<211> LENGTH: 6
<212> TYPE: PRT
<213> ORGANISM: Homo sapiens

<400> SEQUENCE: 2

Cys Ala Asn Asn Thr Gly
1               5

<210> SEQ ID NO 3
<211> LENGTH: 6
<212> TYPE: PRT
<213> ORGANISM: Homo sapiens

<400> SEQUENCE: 3

Cys Ala Cys Gly Thr Gly
1               5

<210> SEQ ID NO 4
<211> LENGTH: 5
<212> TYPE: PRT
<213> ORGANISM: Homo sapiens
```

```
<220> FEATURE:
<221> NAME/KEY: BINDING
<222> LOCATION: (1)..(1)
<220> FEATURE:
<221> NAME/KEY: BINDING
<222> LOCATION: (4)..(4)

<400> SEQUENCE: 4

Xaa Pro Pro Xaa Pro
1               5

<210> SEQ ID NO 5
<211> LENGTH: 21
<212> TYPE: PRT
<213> ORGANISM: Homo sapiens
<220> FEATURE:
<221> NAME/KEY: DNA_BIND
<222> LOCATION: (2)..(3)
<223> OTHER INFORMATION: X is unknown
<220> FEATURE:
<221> NAME/KEY: DNA_BIND
<222> LOCATION: (5)..(7)
<223> OTHER INFORMATION: X is unknown
<220> FEATURE:
<221> NAME/KEY: DNA_BIND
<222> LOCATION: (9)..(13)
<223> OTHER INFORMATION: X is unknown
<220> FEATURE:
<221> NAME/KEY: DNA_BIND
<222> LOCATION: (15)..(16)
<223> OTHER INFORMATION: X is unknown
<220> FEATURE:
<221> NAME/KEY: DNA_BIND
<222> LOCATION: (18)..(20)
<223> OTHER INFORMATION: X is unknown

<400> SEQUENCE: 5

Cys Xaa Xaa Cys Xaa Xaa Xaa Phe Xaa Xaa Xaa Xaa Xaa Leu Xaa Xaa
1               5                   10                  15

His Xaa Xaa Xaa His
            20

<210> SEQ ID NO 6
<211> LENGTH: 22
<212> TYPE: PRT
<213> ORGANISM: Homo sapiens
<220> FEATURE:
<221> NAME/KEY: DNA_BIND
<222> LOCATION: (2)..(4)
<223> OTHER INFORMATION: X is unknown
<220> FEATURE:
<221> NAME/KEY: DNA_BIND
<222> LOCATION: (6)..(8)
<223> OTHER INFORMATION: X is unknown
<220> FEATURE:
<221> NAME/KEY: DNA_BIND
<222> LOCATION: (10)..(14)
<223> OTHER INFORMATION: X is unknown
<220> FEATURE:
<221> NAME/KEY: DNA_BIND
<222> LOCATION: (16)..(17)
<223> OTHER INFORMATION: X is unknown
<220> FEATURE:
<221> NAME/KEY: DNA_BIND
<222> LOCATION: (19)..(21)
<223> OTHER INFORMATION: X is unknown

<400> SEQUENCE: 6

Cys Xaa Xaa Xaa Cys Xaa Xaa Xaa Phe Xaa Xaa Xaa Xaa Xaa Leu Xaa
1               5                   10                  15

Xaa His Xaa Xaa Xaa His
            20
```

-continued

```
<210> SEQ ID NO 7
<211> LENGTH: 23
<212> TYPE: PRT
<213> ORGANISM: Homo sapiens
<220> FEATURE:
<221> NAME/KEY: DNA_BIND
<222> LOCATION: (2)..(5)
<223> OTHER INFORMATION: X is unknown
<220> FEATURE:
<221> NAME/KEY: DNA_BIND
<222> LOCATION: (7)..(9)
<223> OTHER INFORMATION: X is unknown
<220> FEATURE:
<221> NAME/KEY: DNA_BIND
<222> LOCATION: (11)..(15)
<223> OTHER INFORMATION: X is unknown
<220> FEATURE:
<221> NAME/KEY: DNA_BIND
<222> LOCATION: (17)..(18)
<223> OTHER INFORMATION: X is unknown
<220> FEATURE:
<221> NAME/KEY: DNA_BIND
<222> LOCATION: (20)..(22)
<223> OTHER INFORMATION: X is unknown

<400> SEQUENCE: 7

Cys Xaa Xaa Xaa Xaa Cys Xaa Xaa Xaa Phe Xaa Xaa Xaa Xaa Xaa Leu
1               5                   10                  15

Xaa Xaa His Xaa Xaa Xaa His
            20
```

GLUTATHIONE BEADS AND GST FUSION PROTEINS

RELATED APPLICATIONS

This application claims the benefit of priority of provisional application No. 60/757,951, entitled Glutathione-S-Transferase-GFP Fusion Protein Reveals Slow Dissociation from High Site Density Beads and Measures Free GSH, filed Jan. 11, 2006.

GOVERNMENT SUPPORT

This invention was made with government support under Grant nos. AI036357 and EB000264 awarded by the National Institutes of Health and Grant no. MCB0446179 awarded by the National Science Foundation. The government has certain rights in the invention.

FIELD OF THE INVENTION

The present invention relates generally to glutathione derivatized beads which are adapted for use in conjunction with glutathione-S-transferase fusion proteins (generally, GST fusion proteins, which contain a fluorescent label such as fluorescent green protein) for use in flow cytometry. The present invention also relates to methods for detecting and/or quantifying interactions between a GST fusion protein and their binding partners, in particular, labeled binding partners such as fluorescently labeled binding partners. By creating glutathione beads with an appropriate high or increased site density, disadvantages often associated with low affinity systems and quick off-rates in solution may be resolved to provide a workable system and method.

BACKGROUND OF THE INVENTION

Glutathione Conjugated Beads

Glutathione, a ubiquitous tripeptide, is an important cellular constituent, and measurement of reduced and oxidized glutathione is a measure of the redox state of cells. Glutathione-S-transferase (GST) fusion proteins bind naturally to beads derivatized with glutathione, and elution of such bead-bound fusion proteins with buffer containing millimolar glutathione is a commonly used method of protein purification. Many protein-protein interactions have been established by using GST fusion proteins and measuring binding of fusion protein binding partners by GST pulldown assays, usually monitored by Western blot methodology.

In the cellular context, glutathione is an important regulatory tripeptide, γ-glu-cys-gly (GSH), in which the glutamic acid residue is attached by the γ-carboxyl group. It is found in bacterial and mammalian cells at one to ten millimolar concentrations, and serves as a sulfhydryl buffer that maintains the cysteine residues of cellular proteins in the reduced state. Glutathione can be oxidized to a dimer form, 2GSH↔GSSG+2H, and is the major redox couple of animal cells (1). Free radicals are constantly produced by cells, mostly as reactive oxygen species, and an imbalance of pro-oxidant molecules and antioxidant defenses can result in oxidative stress (2); the GSH/GSSG ratio is used as a primary measurement of such stress. Oxidative stress contributes to the pathogenesis of over a hundred diseases or cellular disorders, including hypertension (2), cancer (3), Alzheimer's disease (4), and neuronal dysfunction (5).

Glutathione is also used extensively as a research tool for affinity purification strategies. Glutathione can be attached to carbohydrate-based supports such as Sephadex, and then serves as a matrix for the specific recovery of the enzyme glutathione-S-transferase (GST) (6). Recombinant DNA techniques make the construction of GST fusion proteins simple, which can then also be recovered on glutathione-conjugated beads. Interactions between GST fusion proteins and a proposed binding partner, be it another protein, polypeptide, DNA, RNA, small molecule or carbohydrate, can be studied by incubating the bead-bound GST fusion protein with the binding partner, followed by recovery of the complex on the beads by centrifugation and some accompanying washes. The amount of the bound partner is then frequently determined by Western blot. This is termed a 'GST pull-down' assay, and many variants of it exist (7).

GTPases-RAS and Ras-Related

Ras and Ras-related, small molecular weight GTPases function in the regulation of signaling and cell growth control and collectively serve to control cell proliferation, differentiation and apoptosis. There are over 150 known human proteins belonging to the Ras superfamily of GTPases. When mutant or hyperactivated, Ras family members contribute to oncogenesis and hereditary disorders affecting vision, immune and neurologic function. Strategies for inhibiting Ras to date have relied on altering membrane recruitment with drugs affecting prenylation. Inhibition of prenylation enzymes lacks specificity and is problematic because the cellular prenylation machinery is required for the proper function of many Ras superfamily members. The demonstrated efficacy of targeting drugs to the nucleotide binding pocket of specific kinases offers a paradigm that may be applied to the GTPases.

Ras and related small molecular weight GTPases function in the regulation of signaling and cell growth control, and collectively serve to control cell proliferation, differentiation and apoptosis [5,6]. Ras family members (Ras, Rap, Ral, Rheb among others) are best known for their control of growth factor receptor signaling cascades. When mutant or hyperactivated Ras family members contribute to oncogenesis. The Ras-related GTPases are divided into four subfamilies with the Rab proteins regulating membrane transport, Rho proteins (including Rac and Cdc42) regulating cytoskeletal rearrangements and responses to signaling, Arf/Sar proteins regulating membrane and microtubule dynamics as well as protein transport, and Ran protein controlling nucleo-cytoplasmic transport. Ran is the subject of an independent screening initiative (Weiss, K. UC Berkeley) and Arf family members are membrane anchored via their N-termini in contrast to other family members, which are anchored via their C-termini [7]. The present application will, therefore, focus on representative Ras, Rho, and Rab family members to validate the approach for the identification of new chemical compounds with novel therapeutic potential in cell signaling and growth control.

Ras and Ras-related GTPase functions are tightly regulated and dysregulation is causal in a wide variety of human diseases. Proper functioning of Ras and Ras-related GTPases is regulated at the level of localization and nucleotide binding and hydrolysis. Ras mutations resulting in impaired GTP hydrolysis and plasma membrane hyperactivation are linked to many human cancers [8-13]. Point mutations in the Rab and Rho GTPases are also causal in diverse human diseases affecting pigmentation, immune, and neurologic functions ([14-17] and preliminary findings). Rab and Rho mutants identified in human disease act as dominant negatives either due to a failure to bind GTP or due to inappropriate coupling of the active proteins with downstream effectors. To date, inhibition of Ras and Ras-related proteins has relied largely on altering membrane recruitment with various drugs affecting prenylation [18-20]. Generally, Ras proteins must be farnesylated for proper membrane localization, while Rab and Rho proteins are geranylated. Such strategies lack specificity and are problematic because each of these prenylation machineries is required for the proper function of many Ras superfamily members. Rational drug design has only recently been applied to identify the first two small molecule inhibitors of Rho GTPase family members [21, 22]. Therefore, broadly testing the Ras-related GTPases as targets for small molecule inhibitors and activators via the MLSCN is expected to identify new classes of compounds that may be useful in the treatment of human disease, as well as in unraveling the molecular details of how Ras-related GTPases function.

Flow cytometry enables the simultaneous quantitative analysis in individual cells of multiple optical markers of biochemical expression or physiological response. On microspheres, a variety of molecular interactions can be measured [23]. Five optical parameters are readily measured at once (3 fluorescence and 2 light scatter signals), and specially configured research instruments may simultaneously measure as many as 14 [24]. Flow cytometry is thus an inherently high content measuring methodology. It is also sensitive, capable of detecting fluorescent molecule concentrations as low as 10-100 pM, and as few as hundreds of molecules on a cell or bead. Moreover, due to the optical configuration, the laser in a flow cytometer only excites a very small volume of the sample fluid immediately surrounding the cell. This allows distinction of free and particle-bound fluorescent probe over a wide range of probe concentration. As a consequence, homogeneous (no-wash) assays may be easily implemented to streamline sample processing.

With respect to the serial analysis of individual cells or beads, the flow cytometer has always been considered a high-throughput analysis instrument, routinely analyzing from thousands to tens-of-thousands of particles per second. However, for automated analysis of multiple discrete samples of cells the throughput of flow cytometry has been severely limited, with commercial systems capable of processing only about 2 samples per minute. This is a significant bottleneck when the objective is to screen a large collection of compounds against replicate cell samples. Over a period of several years The New Mexico Team has evolved two successive generations of high throughput flow cytometry sample handling technology to address this issue. The first, designated Plug Flow cytometry, uses a reciprocating multiport flow injection valve to execute up to 10 endpoint assays per min, 4 on-line mixing experiments per min and, in secondary screens, a 15-point concentration gradient of soluble compound in ~2 min (Edwards et al., 1999, 2001a, 2001b) The second generation technology (Kuckuck et al., 2001) designated HyperCyt®, uses instead a peristaltic pump in combination with an autosampler to boost assay throughput to even higher levels. The HyperCyt technology, part of the New Mexico Molecular Libraries Screening Center, will be described in more detail.

Bcl-2 Family Proteins

Apoptosis is governed in part by Bcl-2 family proteins. The human genome contains six genes that encode anti-apoptotic Bcl-2 family members. Each of these proteins can be bound to endogenous proteins that contain a conserved peptidyl domain called the Bcl-2 homology region 3 (BH3). Pro-apoptotic family members include both multidomain proteins, including Bak, and "BH3-only" proteins, including Bim. As proof of concept, pro-apoptotic BH3 peptides that dock at this site in Bcl-2 and Bcl-XL also increased apoptosis of leukemia and lymphoma cells in culture and in SCID mice (Holinger et al., 1999; Wang et al., 2000; and Walensky et al., 2004). The binding of fluorochrome-conjugated BH3 peptides to Bcl-2 family proteins thus provides the basis for construction of fluorescence assays, suitable for high throughput screening (HTS)

BRIEF DESCRIPTION OF THE FIGURES

FIGS. 7A and 7B show the competition of nucleotides for binding to bead-bound GST-Rab7. To measure the competition between the fluorescent GTP analogue and non-fluorescent GTP or GDP, 100 nM (A) or 10 nM (B) GST-Rab7 was preloaded to bGSH. After the unbound GST-Rab7 was removed, 1 µM Bodipy-FL-GTP and increasing concentration ($1 \times 10^{-12}$ to $1 \times 10^{-3}$ M) of GTP (A) or GDP (B) were allowed to competitively bind to GST-Rab7. $EC_{50}$s were $8.3 \times 10^{-7}$ M (GTP) and $5.6 \times 10^{-7}$ M (GDP).

BRIEF DESCRIPTION OF THE INVENTION

Figure 1:
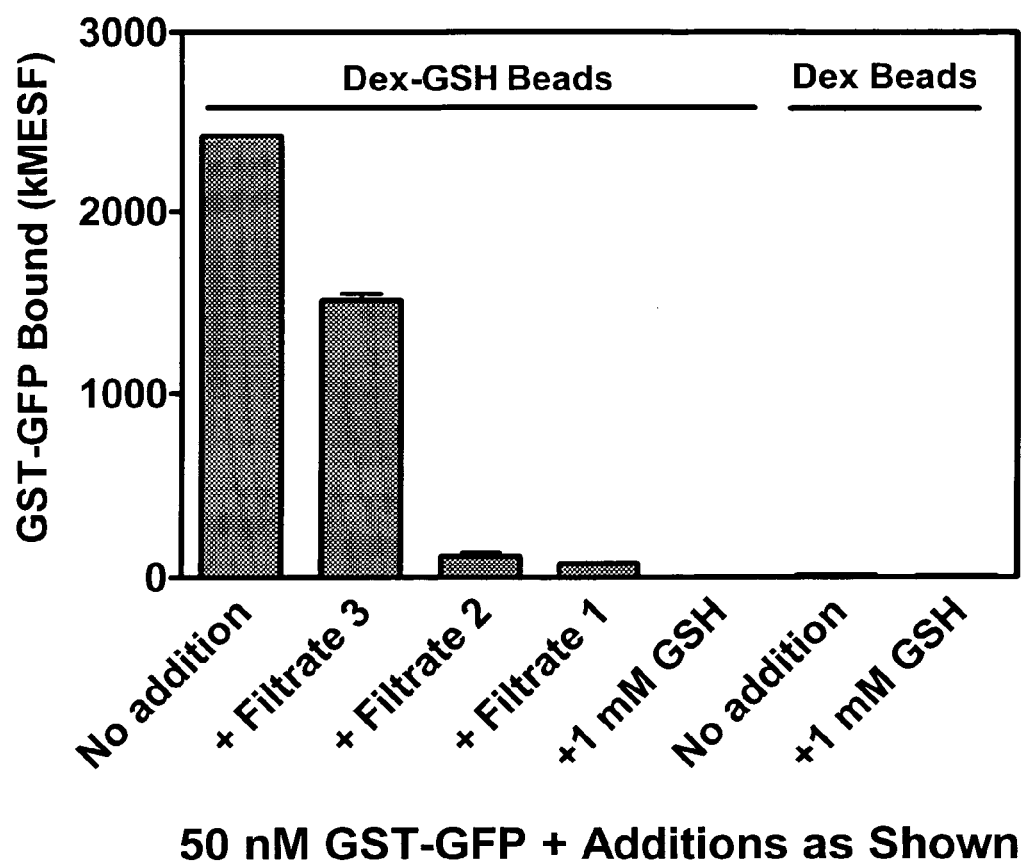
FIG. 1 shows that GSH removal increases GST-GFP binding. A crude bacterial lysate containing GST-GFP was concentrated by ultrafiltration and diluted by a factor of ten using a Microcon YM-30 three times, giving a macromolecular retentate including the GST-GFP, and three consecutive small-molecule filtrates. Each standard ten microliter assay consisted of two microliters of the 250 nM GST-GFP retentate, $10^4$ high site density dextran GSH beads or control dextran beads, and two microliters of buffer, GSH, or filtrate as shown. The mixtures were suspended gently with a vortex mixer as described in Materials and Methods for two hours at 4° C., then diluted to 200 microliters for determination of bead fluorescence.

According to a first broad aspect of the present invention, there is provided beads suitable for flow cytometry ("flow cytometry beads") which have been modified/derivatized with glutathione to provide a high site density. These beads may be used in flow cytometry applications, for example, in conjunction with labeled glutathione-S-transferase (GST) enzyme to measure glutathione in cellular lysates and in GST-fusion protein affinity chromatography eluates. In addition, the glutathione beads of the present invention may be used to quantify interactions between GST fusion proteins which are bound thereto and their labeled binding partners using flow cytometry, as well as identifying compounds which may function as agonists, antagonists or regulators (allosteric) of the proteins fused to GST (fused proteins) in the GST fusion proteins. The beads find utility in flow cytometry applications despite low affinity and/or a quick off-rate of typical GST-glutathione bead systems, because of the high binding site density. By virtue of the present invention, application of flow cytometry to GST fusion proteins is generalized.

This invention provides glutathione linked beads which allow a generalizable approach to investigating the interaction of a GST-fusion protein with a labeled soluble binding partner. Thus, the interactions between a protein fused ("fused protein") with GST in a GST fusion protein and its detectably labeled, preferably fluorescently labeled binding partner may be quantified using high throughput flow cytometry. The glutathione derivatized beads of the present invention are an advance in the art in that the high site density results in bound GST fusion proteins being constrained to the surface of a single bead without hopping to the next bead in multiplex assays, leading to enhanced accuracy in flow cytometry systems. The system may be used with any protein which may be fused with GST to produce a GST fusion protein which binds (from the GST protein) to glutathione beads of the present invention.

In the present invention, the soluble GST fusion protein comprises GST and a second fused protein, preferably a protein which has a known binding partner, which is detectably labeled, preferably fluorescently labeled. In certain aspects of the invention, the fused protein may be a fluorescent protein, including a green, red or cyan fluorescent protein, preferably a green fluorescent protein (GFP) or the fused protein may be further labeled with a fluorescent protein or other fluorescent label. The basic components of the present invention may be utilized to provide numerous assays which measure the impact (as antagonists, agonists or modulators) of potential drugs on the fused protein and its binding partners using bead-based flow cytometric analysis.

In a method aspect of the invention, compounds which have the potential for being antagonists, agonists or regulators (allosteric) of the fused protein are assayed by flow cytometry utilizing the above-described high site density glutathione beads, a soluble GST fusion protein comprising GST and a fused protein bound to said glutathione beads through glutathione GST binding, and a soluble detectably labeled (preferably fluorescently labeled) binding partner which binds to said fused protein to form a binding partner-fused protein complex, wherein a compound of unknown activity is exposed to said binding partner-fused protein complex in solution such that displacement of said fluorescent binding partner from said fused protein evidences that the unknown compound is an agonist, antagonist or regulator (allosteric) of said fused protein.

In a further method step(s), the compound identified in the above assay as an agonist, antagonist or regulator (allosteric) may be further assayed to determine its activity as an agonist, antagonist or regulator of the fused protein. The method can be applied generally to virtually any protein which is fused to GST to form a GST fusion protein to identify potential drug candidates which may influence the activity of said fused protein. Thus, the present invention also provides a generalizable drug discovery tool for various enzymes, receptors and other proteins which can presented in a GST fusion protein. In addition, binding partners of fused proteins which have unidentified binding partners may also be identified using the methods according to the present invention.

In certain preferred aspects of the invention, the fused protein is a GTPase, in particular, a RAS or RAS-related GTPas and in particular, RAS (H-Ras, K-Ras, N-Ras), Rab, Rac and Rho (Rab5, Rab7, CMT Rab7 mutants, Rab8, Rab9, Rab11, Rab 26, Rac1, Rac2, etc.) proteins as well as Cdc42 and RhoA as otherwise disclosed herein and the binding partner is a fluorescently labeled GTP, in particular, Bodipy fluorescently labeled GTP (Bodipy-FL-GTP), or the Rab7 effectors XAPC7, or Rab binding partners hVps150, hVps34 or myotubularins (for Rab GTPase) and RILP as otherwise described herein. In alternative embodiments, the fused protein is a Bcl-2 protein such as Bcl-2, Bcl-XL, Bfl-1, Mcl-1, Bcl-W and Bcl-B and the binding partner is a BH3 peptide, a BIM peptide or Bak protein, preferably a fluorescently labeled BH3 peptide (FITC-BH3 peptide-a BH3 peptide such as a BH3 peptide from Bid or Bid BH3 peptide which is conjugated with FITC-FITC-Bid BH3), F-Bim (Bim peptide fluorescently labeled with fluorescein) or F-Bak (Bak peptide fluorescently labeled with fluorescein). BH3 peptides are those generally based upon sequences found in Bcl-2 family proteins and include BH3 peptide base upon sequence(s) found in Bim (Bim BH3 peptide), sequence(s) found in Bid (Bid BH3 peptide, sequence(s) found in PUMA (PUMA BH3 peptide), sequence(s) found in Bak (Bak BH3 peptide).

These and other aspects of the invention are described in greater detail in the detailed description of the invention.

DETAILED DESCRIPTION OF THE INVENTION

Numbers in parentheses in context generally refer to the references which are set forth and listed in the section after the experimental in the present specification. Terms not specifically defined herein are to be given their common meaning as understood by those of ordinary skill in the art. Relevant portions of all references which are cited herein, within context whether, published papers, website information or related information, are incorporated by reference herein.

As used herein, the following terms have the following respective meanings.

The term "glutathione derivatived flow cytometer bead" is used to describe a flow cytometer bead which has been derivatized with glutathione and has a high glutathione site density. Flow cytometer beads useful in the present invention range in size from about 1 to about 30 microns (μm) in diameter, with a preferred range of about 3 to about 10 microns in diameter. The binding site density of the glutathione beads (the number of glutathione residues capable of binding GST fusion protein) according to the present invention ranges from about $7.5 \times 10^3$ binding sites/μm$^2$ to about $5 \times 10^5$ binding sites/μm$^2$, alternatively about $1 \times 10^4$ binding sites/μm$^2$ to about $1 \times 10^5$ binding sites/μm$^2$, alternatively about $1 \times 10^4$ binding sites/

μm² to about 5×10⁴ binding sites/μm². The term "binding site density" is used to indicate the number of binding sites (glutathione residues) upon which a GST fusion protein may bind per μm² on a flow cytometer bead according to the present invention. The above range of binding sites for GST fusion proteins unexpectedly produces a low GST fusion protein offrate, which is appropriate for flow cytometer assays for identifying and quantifying potential agonist, antagonist or regulatory (allosteric) activity of unknown compounds, which bind to the fused protein and displace an appropriately labeled binding partner.

It is determined that the above range of binding site densities is sufficiently high in glutathione binding sites for GST fusion proteins adequate to conduct flow cytometry assays. As noted, the high binding site density of the glutathione derivatized flow cytometer beads of the present invention have a low offrate bound GST-fusion protein offrate and consequently, may be used generally in flow cytometer assays according to the present invention. The glutathione derivatized flow cytometer beads of the present invention, because of the high binding site density and low offrate of the GST fusion proteins bound thereto, may be utilized generically in flow cytometer systems using a huge number of GST fusion proteins. The flow cytometer assays of the present invention are useful with any GST fusion proteins wherein the binding partner of the fused protein with the fused protein preferably has a $K_d$ (dissocation constant) which is lower than the offrate of the GST fusion protein from the glutathione derivatized bead, more preferably the binding partner of the fused protein with the fused protein has a $K_d$ (dissocation constant) which is lower than about 10 μmolar.

The flow cytometer beads may be made of any appropriate material, functionalized to covalently bind glutathione (generally, but not exclusively at the cysteinyl thiol residue of the glutathione molecule). Any polymeric material, including glass beads may be used, provided that they are of an appropriate diameter (as described above) for flow cytometry and may be derivatized to contain an appropriate electrophilic or nucleophilic group (preferably, an OH or $NH_2$ group). Thus, compounds such as amino-containing polystyrene, latex, polycarbohydrates including agarose dextran (Superdex), glass and other polymeric materials too numerous to many may be used in the present invention. It is noted that the polymeric material is derivatized to contain sufficient electrophilic or nucleophilic groups (preferably, OH or $NH_2$, more preferably $NH_2$) to be conjugated (linked covalently) with a glutathione group. Both carbohydrate fiber (hydrophilic) and amino-polystyrene beads are preferably used as the starting material. However, any type of bead material can be used, and using standard crosslinking chemistries containing two functional groups (which may contain preferably two electrophlic groups or an electrophlilic and nucleophilic group) well known in the art, glutathione may be readily attached to the polymeric material (preferably through the SH bond of the cysteinyl residue of glutathione to an electrophilic moiety of the crosslinking compound) in the high binding site density which is found useful in the present invention.

Figure 23:
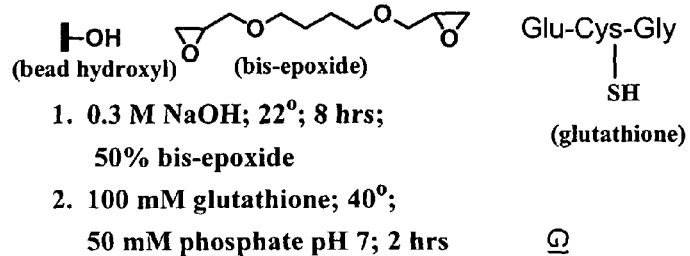
FIG. 23 shows exemplary chemistry which can be used to conjugate or crosslink a glutathione residue to a polymeric flow cytometer bead according to the present invention.
Figure 23:
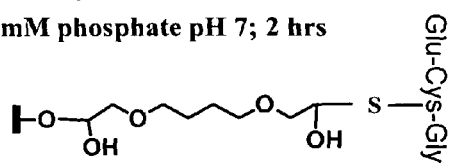
Figure 23:
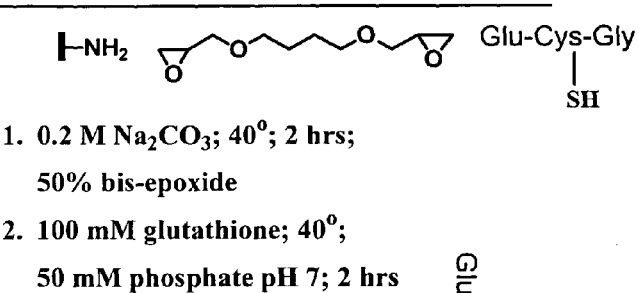
Figure 23:
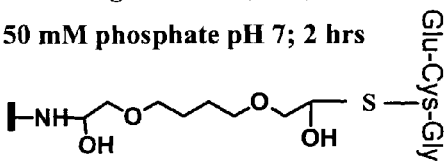
Figure 23:
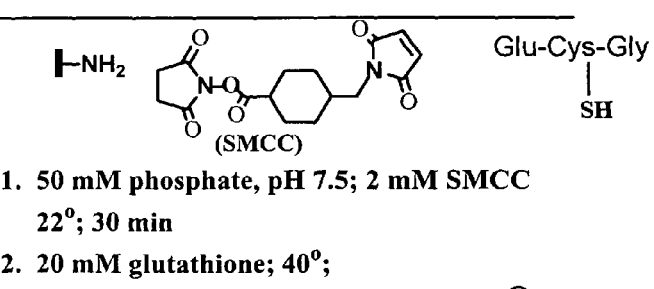
Figure 23:
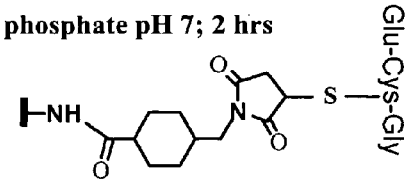

Specific examples of bead materials and chemistries which have found use include the following preferred examples:

a) 13 μm (micron) carbohydrate (Superdex peptide) beads using bis-epoxide crosslinker and glutathione;

b) 8 μm and 4 μm amino-polystyrene beads using bis-epoxide crosslinker and glutathione; and c) 6 μm and 4 μm amino-polystyrene beads using SMCC bifunctional crosslinker and glutathione As depicted in attached FIG. 23.

It is noted that nearly all soluble GST fusion proteins bind to the glutathione derivatized beads at high binding density according to the present invention, sometimes with minor modification. It is noted that in binding, the fused proteins, which are separated from the GST by a few amino acids, rotate in solution and are readily able to bind their normal cellular binding partners.

The present inventors have found that six GST-Bcl-2 family proteins: GST-Bcl-2; GST-Bcl-XL; GST-Bcl-W; GST-Bcl-B; GST-Bfl-1; and GST-Mcl-1 bind a fluorescently labeled peptide from one Bcl-2 family member, FITC-Bcl-Bid BH3 and that numerous GST-Rab family proteins and a number of mutants of same bind to fluorescently labeled GTP. The present invention is adaptable to virtually all soluble GST-fusion proteins and can be used with all detectably labeled (preferably, fluorescently labeled) binding partners of the fused proteins in the GST fusion proteins.

All the systems work for flow cytometry because the fusion protein, as a consequence of the high binding site density for the glutathione derivatized flow cytometry beads, stay on the bead after dilution for far longer than expected, by a factor of about 200 (unless displaced by free glutathione). This allows analysis and identification of potential agonists, antagonists or regulators (allosteric) to the fused protein by displacement of its labeled binding partner in flow cytometry assays.

The term "fusion protein", as used herein, is meant to refer to a chimeric protein which comprises the protein glutathione-S-transferase and an additional protein fused to the GST protein ("fused protein"). It is noted here that for practical purposes, any soluble fusion protein of GST wherein the GST binds to the glutathione linked beads of the present invention are contemplated for use herein. In the present invention, a GST fusion protein binds to the high site density glutathione beads. The fused protein of the GST fusion protein has a binding partner which typically binds to the fused protein of the GST fusion protein in the absence of a competitive antagonist or a regulator (allosteric) molecule. The present invention allows a quantitiative analysis of a fused protein with its binding partner by flow cytometry. In one aspect of the present invention, a molecule is assayed to determine whether or not it is an antagonist or other regulator (allosteric) of the fused protein by flow cytometry.

GST fusion proteins are well known in the art. Literally, thousands of GST fusion proteins are available for use in the present invention and virtually any target protein may be utilized to create a GST fusion protein. Many of the GST fusion proteins useful in the present invention are available from commercial sources, such as Chemicon (a division of Millipore), General Electric (Amersham Division), Sigma-Aldrich, Inc., among numerous other suppliers.

Alternatively, virtually any GST fusion protein may be created using techniques which are well-known in the art. One commercial system, the Glutathione S-transferase (GST) gene fusion system of Millipore, Inc. (Chemicon Division) is an integrated system for the expression, purification and detection of fusion proteins produced in bacterial, yeast, mammalian and insect cells. In this well-known approach, the sequence encoding the GST protein is incorporated into an expression vector, generally upstream of the multi-cloning site. The sequence encoding the protein of interest is then cloned into this vector. Induction of the vector results in expression of a fusion protein—the protein of interest fused (fused protein) to the GST protein. The fusion protein can then be released from the cells and purified.

Purification of the GST fusion protein is facilitated by the affinity of the GST protein for glutathione residues: The present glutathione-labeled beads of the present invention may be useful in purifying GST fusion proteins. In a similar fashion, glutathione residues are coupled to a resin and the expressed protein product is brought into contact with the resin. The fusion protein binds to the glutathione-resin complex and all other non-specific proteins in the sample can be washed off. The fusion protein can then be released from the resin using a mild elution buffer which is of low pH. Fusion proteins may also be purified using a number of GST antibodies now available on the market.

Fused proteins (in GST fusion proteins) for use in the present invention include small G proteins such as Rab, Rho and Ras GTPases, as well as the Bcl-2 family proteins which govern apoptosis in cells. These include the Ras-related small proteins H-Ras, K-Ras and N-Ras proteins; the Rac subgroup of Rho GTPases including Rac1 and Rac2; the Rab subgroup of GTPases including Rab 5, Rab 6, Rab 7, Rab 7 CMT mutants, Rab 8, Rab 9, Rab 11, Rab 26, Rab 27 and Rab 27 mutants, among others. Other fused proteins include Metnase and FEN (flap endonuclease I), numerous DNA or RNA sequence binding proteins, enhancer proteins which bind DNA and RNA, among numerous others.

The term "binding partner" refers to a molecule which under physiological conditions, binds to a fused protein to effect a response associated with that binding. The binding partner may be a protein, a polypeptide (in particular known protein regulatory or binding domains such as SH2, SH3, WD40, etc), a nucleotide sequence (RNA or DNA), a nucleotide (such as ATP, GTP, among others), or other natural ligand (including a small molecule) which binds to the fused protein. In the present invention, in most instances, when assaying for inhibitors, agonists and/or regulators of the fused protein, the binding partner will be detectably labeled, preferably with a fluorescent label, so that the presence or absence of the binding partner at a binding site on the fused protein may be detected. The term "ligand" refers to any molecule which binds to the fused protein or other target of interest and subsumes the term "binding partner" under its rubric. GTP is a preferred small molecule binding partner for the GTPase fused proteins and Bim BH3 is a preferred binding partner for the Bcl-2 proteins which are otherwise disclosed herein. Fused GST-proteins may have multiple binding partners and the assay may be modified to detect binding of multiple partners, e.g. small molecules and macromolecules, simultaneously or sequentially.

The term "DNA binding domain" refers to a protein which binds a sequence of a DNA molecule as a binding partner in the present application. There are several types of proteins with DNA binding domains including ANTH domain; ATP-binding motif; Leucine Zipper domain (BZIP); Basic-helix-loop-helix; Bromodomain; CARD domain; Death effector domain; ENTH domain; ETS domain; Helix-turn-helix (homeodomain; Homeobox; Immunoglobulin fold; KASH domain; Kringle domain; Krüppel associated box; Leucine-rich repeat; MSin3 interaction domain; Motif domain; PDZ domain; Pleckstrin homology domain; Ribonuclease inhibitor domain; SH2 domain; SH3 domain; SUN domain; Winged Helix; Unusual binding domain and Zinc finger.

The ANTH domain is a membrane binding domain that shows specificity for PtdIns(4,5)P2. Its structure is a solenoid of 9 helices. The PtdIns(4,5)P2 binding residues are spread over several helices at the tip of the structure. The PtdIns(4,5)P2 binding sequence is Kx9Kx(K/R)(H/Y). The ANTH domain is found in AP180 and in CALM. An ANTH domain is also found in HIP1 and HIP1R and the PtdIns(4,5)P2 binding sequence is conserved. See *Science*, 291, 1051-1055 (2001).

An ATP-Binding Motif is a specific sequence of protein subunits (and hence genomic DNA base pairs) that promotes the attachment of ATP to a target protein. An ATP binding site is a protein micro-environment where ATP is captured and hydrolized to ADP, releasing energy that is utilized by the protein to "do work" by changing the protein shape and/or making the enzyme catalytically active. The same ATP binding motif is used in many proteins: hence a "motif" that is similar across a range of proteins. The genetic and functional similarity of such a motif demonstrates micro-evolution: proteins have co-opted the same binding sequence from other enzymes rather than developing them independently. ATP binding sites, which may be representative of an ATP binding motif, are utilized on many proteins which perform function requiring an input of energy (from ATP). Such sites are located on active membrane transporters, microtubule subunits, and various hydrolytic and proteolytic enzymes.

The Basic Leucine Zipper Domain (bZIP domain) is found in many DNA binding eukaryotic proteins. One part of the domain contains a region that mediates sequence specific DNA binding properties and the Leucine zipper that is required for the dimerization of two DNA binding regions. The DNA binding region comprises a number of basic aminoacids such as arginine and lysine. bZIP domain containing proteins include AP-1 fos/jun heterodimer that forms a transcription factor; Jun-B transcription factor; CREB cAMP response element transcription factor; and OPAQUE2 (O2) transcription factor of the 22-kD zein gene that encodes a class of storage proteins in the endosperm of maize (*Zea Mays*) kernels. The leucine zipper contains an alpha helix with a leucine at every $7^{th}$ amino acid. If two such helices find one another, the leucines can interact as the teeth in a zipper, allowing dimerization of two proteins. When binding to the DNA, basic amino acid residues bind to the sugar-phosphate backbone while the helices sit in the major grooves.

Basic-helix-loop-helix (bHLH) is a protein structural motif that characterizes a family of transcription factors. The motif is characterized by two α helices connected by a loop. Transcription factors including this domain are typically dimeric, each with one helix containing basic amino acid residues that facilitate DNA binding (Lodish et. al., *Molecular Cell Biology* 5/e, 2004, W.H. Freeman). One helix is typically smaller and due to the flexibility of the loop, allows dimerization by folding and packing against another helix. The larger helix typically contains the DNA binding regions. bHLH proteins typically bind to a consensus sequence called an E-box, CANNTG. The canonical E-box is CACGTG (palindromic), however some bHLH transcription factors bind to different sequences, which are often similar to the E-box. Examples of transcription factors containing a bHLH include: BMAL1-Clock, c-Myc; MyoD; HIF; NPAS1, MOP5; Scl, also known as Tall and proneural bHLH genes like p-CaMKII, and pSer (336)NeuroD. bHLH transcription factors are often important in development or cell activity. BMAL1—Clock is a core transcription complex in the molecular circadian clock. Other genes, like c-Myc and HIF-1 have been linked to cancer due to their effects on cell growth and metabolism. Since many bHLH transcription factors are heterodimeric, their activity is often highly regulated by the dimerization of the subunits. One subunit's expression or availability is often controlled while the other subunit is constitutively expressed.

A bromodomain is a protein domain that recognizes acetylated lysine residues on the N-terminal tails of histones. This recognition is often a prerequisite for protein-histone association and chromatin remodeling. The domain itself adopts an all-α protein fold, a bundle of four alpha helices.

Caspase recruitment domains, or CARD domains, are interaction motifs found in a wide array of proteins, typically those involved in processes relating to inflammation and apoptosis. These domains mediate the formation of larger protein complexes via direct interactions between individual CARDs. CARD domains are found on a strikingly wide range of proteins, including helicases, kinases, mitochondrial proteins, caspases, and other cytoplasmic factors. CARD domains are a subclass of protein motif known as the death fold, which features an arrangement of six to seven antiparallel alpha helices with a hydrophobic core and an outer face composed of charged residues. Other motifs in this class include the pyrin domain (PYD), death domain (DD), and death effector domain (DED), all of which also function primarily in regulation of apoptosis and inflammatory responses. CARD domains were originally characterized based on their involvement in the regulation of caspase activation and apoptosis. The basic six-helix structure of the domain appears to be conserved as far back as the ced-3 and ced-4 genes in *C. elegans*, the organism in which several components of the apoptotic machinery were first characterized. CARD motifs are present on a number of proteins that promote apoptosis, primarily caspases 1, 4, 5, 9, and 15 in mammals. CARD domains are involved in apoptosis, mammalian immune response and autoimmunity.

The death-effector domain (DED) is a protein interaction domain found in inactive procaspases (cysteine proteases) and proteins that regulate caspase activation in the apoptosis cascade such as FAS-associating death domain-containing protein (FADD). FADD recruits procaspase 8 and procaspase 10 into a death induced signaling complex (DISC). This recruitment is mediated by a homotypic interaction between the procaspase DED and a second DED in an adaptor protein that is directly associated with activated TNF receptors. Complex formation allows proteolytic activation of procaspase into the active caspase form which results in the initiation of apoptosis (cell death).

The ENTH domain is a membrane binding domain which is found in members of the epsin protein family. In epsin-1 it shows specificity for the membrane protein phosphatidylinositol-4,5-bisphosphate (pi-4,5-bp), however not all ENTH domains bind to this molecule. Binding causes tubulation of liposomes and in vivo this membrane-bending function is normally coordinated with clathrin polymerisation. When pi-4,5-bp binds to the domain an additional helix folds around the headgroup (helix 0) and thus the lipid headgroup gets buried in a pocket. The outer surface of this new helix is hydrophobic and inserts into the membrane like a wedge and helps to drive membrane curvature.

The ETS domain was first discovered in the ETS oncogene. The domain is 85-90 amino acids long and is folded into a structure with 3 helices and a 4-strand beta-sheet, where the third helix is the recognition helix. ETS proteins are transcription factors that are activated via phosphorylation by the MAP kinases.

Helix-turn-helix (also called homeobox or homeodomain) domains were originally discovered in bacteria. This motif is commonly found in repressor proteins and is about 20 amino acids long. In eukaryotes, the homeodomain is comprised of 3 helices, of which the third recognizes the DNA (aka recognition helix). They are common in proteins that regulate developmental processes.

A homeobox is a DNA sequence found within genes that are involved in the regulation of development (morphogenesis) of animals, fungi and plants. Genes that have a homeobox are called homeobox genes and form the homeobox gene family. A homeobox is about 180 base pairs long; it encodes a protein domain (the homeodomain) which can bind DNA. Homeobox genes encode transcription factors which typically switch on cascades of other genes, for instance all the ones needed to make a leg. The homeodomain binds DNA in a specific manner. However, the specificity of a single homeodomain protein is usually not enough to recognize only its desired target genes. Most of the time, homeodomain proteins act in the promoter region of their target genes as complexes with other transcription factors, often also homeodomain proteins. Such complexes have a much higher target specificity than a single homeodomain protein.

An Immunoglobulin Fold os a domain consisting of a beta-sheet structure with large connecting loops, which serve to recognize either DNA major grooves or antigens. Usually found in immunoglobulin proteins, they are also present in Stat proteins of the cytokine pathway. This is likely due to the fact that the cytokine pathway evolved relatively recently and has made use of systems that were already functional, rather than creating its own.

KASH (Klarsicht, ANC-1, Syne Homology) domains are conserved C-terminal protein regions less than ~30 amino acids. KASH domains always follow a transmembrane domain. Most proteins containing KASH domains are thought to be involved in the positioning of the nucleus in the cell. It is thought that KASH domains interact with proteins containing SUN domains in the space between the outer and inner nuclear membranes to bridge the nuclear envelope and transfer force from the nucleocytoskeleton to the cytoplasmic cytoskeleton. Some mammalian proteins that contain KASH domains are the Nesprins-1, 2, and 3 (also called Synes, Mynes, Nuance, Enaptin).

Kringle Domains are conserved sequences that fold into large loops stabilized by 3 disulfide linkages. These are of some importance in protein-protein interactions with blood coagulation factors. The name Kringle comes from the Scandinavian pastry that these structures resemble.

The Krüppel associated box (KRAB) domain is a category of transcriptional repression domains present in approximately 200 human zinc finger protein-based transcription factors. The KRAB domain typically consists of about 75 amino acid residues whilst the minimal repression module is approximately 45 amino acid residues. It is predicted to function through protein-protein interactions via two amphipathic helices. Substitutions for the conserved residues abolish repression. Over 10 independently encoded KRAB domains have been shown to be effective repressors of transcription, suggesting this activity to be a common property of the domain. Examples of KRAB-ZFPs include ZNF43, ZNF91, HPF4, HTF10 and HTF34.

A leucine-rich repeat (LRR) is a protein structural motif that forms an α/β horseshoe fold. It is composed of repeating 20-30 amino acid stretches that are unusually rich in the hydrophobic amino acid leucine. Typically, each repeat unit has beta strand-turn-alpha helix structure, and the assembled domain, composed of many such repeats, has a horseshoe shape with an interior parallel beta sheet and an exterior array of helices. One face of the beta sheet and one side of the helix array are exposed to solvent and are therefore dominated by hydrophilic residues. The region between the helices and sheets is the protein's hydrophobic core and is tighly sterically packed with leucine residues.

The mSin3 interaction domain (SID) is present on several transcriptional repressor proteins including TGFβ (transforming growth factor β) and Mad. It interacts with the paired amphipathic alpha-helix 2 (PAH2) domain of mSin3, a transcriptional repressor domain attached to some transcription repressor proteins such as the mSin3A corepressor. Action of histone deacetylase 1 and 2 (HDAC1/2) is induced by the interaction of mSin3A with a multi-protein complex containing HDAC1/2. Transcription is also repressed by histone deacetylase-independent means.

Motif Domains are protein domains that contain periodic short sequence motifs that interact with other proteins. They are in contrast to folded structured domain. For example proline rich domains are motif domain and frequently contain multiple different SH3 binding motifs scattered throughout these relatively unstructured domains. Motif domains are also found in many endocytic proteins, where they again are generally unstructured domains designed to contain a large number of possible protein interaction motifs. For example the motif domain of Eps15 contains at least 15 repeats of DPF and thus can interact with many copies of the AP2 alpha appendage. Other sequence motifs often frouwnd in motif domains are NPF motifs that bind to EH domains and clathrin terminal domain binding motifs The PDZ domain is a common structural domain of 80-90 amino-acids found in the signaling proteins of bacteria, yeast, plants, and animals. PDZ is an acronym combining the first letters of three proteins—post synaptic density protein (PSD95), *Drosophila* disc large tumor suppressor (DIgA), and zo-1 protein—which were first discovered to share the domain. PDZ domains are also referred to as DHR (Dig homologous region) or GLGF (glycine-leucine-glycine-phenylalanine) domains. These domains help anchor transmembrane proteins to the cytoskeleton and hold together signaling complexes. See, Ponting, *Protein Sci* 6 (2): 464-8 (1997); and Ranganathan, et al. *Curr Biol* 7 (12): R770-3 (1997).

Pleckstrin homology domain (PH domain) is a protein region of approximately 120 amino acids that can bind phosphoinositides (such as inositol 1,4,5-trisphosphate and phosphatidylinositol 4,5-bisphosphate), the βγ-subunits of heterotrimeric G proteins and protein kinase C. Through these interactions, the PH domain plays a role in the membrane recruitment of proteins containing the PH domain, thus targeting them to appropriate cellular compartment or enabling them to interact with other components of the signal transduction pathways.

Ribonuclease inhibitor (RI) is a large (~450 residues, ~49 kDa), acidic (pI ~4.7), leucine-rich repeat protein that forms extremely tight complexes with certain ribonucleases. It is a major cellular protein, comprising ~0.1% of all cellular protein by weight, and appears to play an important role in regulating the lifetime of RNA. RI has a surprisingly high cysteine content (~6.5%, cf. 1.7% in typical proteins) and is sensitive to oxidation. R1 is also rich in leucine (21.5%, compared to 9% in typical proteins) and commensurately lower in other hydrophobic residues, esp. valine, isoleucine, methionine, tyrosine, and phenylalanine.

The Src homology 2 domain ("SH2 domain") is a protein domain of about 100 amino acid residues first identified as a conserved sequence region among the oncoproteins Src and Fps. Similar sequences were later found in many other intracellular proteins involved in signal transduction, such as Abl, ZAP70, STAT proteins, Grb2, and RasGAP. A large number of SH2 domain structures have been solved and many SH2 proteins have been knocked out in mouse (see the SH2 domain website). SH2 domains typically bind a phosphorylated tyrosine residue in the context of a longer peptide motif within a target proteins, and SH2 domains represent the largest class of known pTyr-recognition domains[1]. Phosphorylation of tyrosine residues in a protein occurs during signal transduction and is carried out by tyrosine kinases. In this way, phosphorylation of a substrate by tyrosine kinases acts as a switch to trigger binding to an SH2 domain-containing protein. The intimate relationship between tyrosine kinases and SH2 domains is supported by their coordinate emergence during eukaryotic evolution. SH2 domains are not present in yeast and appear at the boundary between protozoa and animalia in organisms such as the social amoeba *Distyostelium discoidum*[2]. A detailed bioinformatic examination of SH2 domains of human and mouse reveals 120 SH2 domains contained within 110 proteins encoded by the human genome[3], representing a rapid rate of evolutionary expansion among the SH2 domains.

Many biological signaling proteins use this mode of regulated protein-protein interactions as a means to localize proteins to various sub-cellular compartments, control enzymatic activities of proteins as well as nucleate multiprotein complexes, to name a few. The SH2 domain has thus become a prototype for a large number of modular interaction domains that have been since identified. The discovery of the SH2 domain and its many roles in signal transduction introduced the critical concept of how biology has exploited the use of modular interaction domains to create complex signaling networks. Examples of SH2 domain proteins include: Abl; GRB2; RasGAP; STAT proteins; ZAP70; SHP2; PI3K; Phospholipase C γ form; CRK; SOCS and Src.

Src homology 3 domain (or SH3 domain) is a small protein domain of about 60 amino acid residues first identified as a conserved sequence in the non-catalytic part of several cytoplasmic tyrosine kinases such as Abl and Src and it has been then identified in several other protein families such as: phospholipases, PI3 Kinase, ras GTPase activating protein, adaptor proteins, CDC24 and CDC25. The SH3 domain has a characteristic fold which consists of five or six β-strands arranged as two tightly packed anti-parallel β sheets. The linker regions may contain short helices. The SH3 domain is found in proteins that interact with other proteins and they mediate assembly of specific protein complexes via binding to proline-rich peptides in their respective binding partner. SH3-binding domains have a consensus sequence:

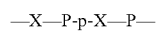

1 2 3 4 5 with 1 and 4 being aliphatic amino acids, 2 and 5 always and 3 sometimes being proline. The sequence binds to the hydrophobic pocket of the SH3 domain. SH3 domains are often found in functions concerning the cytoskeleton, the ras protein, and the src kinase. They also increase the substrate specificity of tyrosine kinases by binding far away from the catalytic center of the kinase. Examples of proteins containing SH3-binding domains include: Adaptor proteins; CDC24; CDC25; PI3 kinase; Phospholipase; Ras GTPase activating protein; Vav proto-oncogene and ZAP70.

SUN (Sad1p, UNC-84) domains are conserved C-terminal protein regions a few hundred amino acids long. SUN domains are usually found following a transmembrane domain and a less conserved region of amino acids. Most proteins containing SUN domains are thought to be involved in the positioning of the nucleus in the cell. It is thought that SUN domains interact directly with KASH domains in the space between the outer and inner nuclear membranes to bridge the nuclear envelope and transfer force from the nucleocytoskeleton to the cytoplasmic cytoskeleton. Some proteins that contain SUN domains include the mammalian proteins SUN1, 2, and 3 and SPAG4.

Winged Helix domain consists of about 110 amino acids, having four helices and a two-strand beta-sheet. These proteins are classified into 17 families called FoxA-FoxQ. Mutations in FoxP proteins are implicated in human autoimmune diseases.

A Zinc finger is a protein domain that can bind to DNA. A zinc finger consists of two antiparallel p strands, and an α helix. The zinc ion is crucial for the stability of this domain type—in absence of the metal ion the domain unfolds as it is too small to have a hydrophobic core. One very well explored sub-set of zinc-fingers (the $C_2H_2$ class) comprises a pair of cysteine residues in the beta sheets and two histidine residues in the alpha helix which are responsible for binding a zinc ion. The two other classes of zinc finger proteins are the $C_4$ and $C_6$ classes.

The structure of each individual finger is highly conserved and consists of about 30 amino acid residues, constructed as a ββα fold and held together by the zinc ion. The α-helix occurs at the C-terminal part of the finger, while the β-sheet occurs at the N-terminal part. The consensus sequence of a single finger is: $Cys-X_{24}-Cys-X_3-Phe-X_5-Leu-X_2-His-X3-His$. Many transcription factors (such as Zif268), regulatory proteins, and other proteins that interact with DNA contain zinc fingers. These proteins typically interact with the major groove along the double helix of DNA in which case the zinc fingers are arranged around the DNA strand in such a way that the α-helix of each finger contacts the DNA, forming an almost continuous stretch of α-helices around the DNA molecule. The binding specificity for 3-4 base pairs are conferred by a short stretch of amino acid residues in the α-helix. The primary position of the amino acid residues within the α-helix interacting with the DNA are at positions-1, 3 and 6 relative to the first amino acid residue of the α-helix. Other amino acid positions can also influence binding specificity by assisting amino acid residues to bind a specific base or by contacting a fourth base in the opposite strand, causing target-site overlap. Some primary neuron-specific transcriptional regulator that may be involved in mediating early neural development are also zinc finger-based.

The term "crosslinking agent" or "coupling agent" refers to a bifunctional organic compound containing either two electrophilic functional groups or one electrophilic and one nucleophilic functional group which is used to covalently link the flow cytometer polymeric bead material to glutathione. Preferred crosslinking agents according to the present invention include bis-epoxide crosslinking agents such as 1,4-butanediyl diglycidyl ether or the crosslinking agents succinimidyl-4-(N-maleimidomethyl)cyclohexane-1-carboxylate (SMCC) or sulfosuccinimidyl-4-(N-maleimidomethyl)cyclohexane-1-carboxylate (Sulfo-SMCC).

The term "detectably labeled" as used herein is meant to refer to a binding partner of a fused protein which contains a label which is detectable and is preferably fluorescently detectable. The term "fluorescently labeled" as used herein is meant to refer to a binding partner of a fused protein, or, in some cases, the fused protein itself, which is detectably labeled with a fluorescent moiety such that the binding partner may be detected by measuring fluorescent light being emitted from the moiety after exposure to a fluorescent light source, preferably in a flow cytometer system. The fluorescent moiety may be a a small molecule or a protein, such as fluorescent green, fluorescent red or fluorescent cyan polypeptides, all well known in the art. Fluorescent proteins may be used by organically conjugating the fluorescent protein to a binding partner or alternatively, and preferably, where appropriate, the fluorescent protein may be introduced as a fused protein in a chimeric or fusion protein along with the binding partner (which is a protein or polypeptide). Methods for producing fluorescently-labeled proteins as fusion proteins or fusion polypeptides are well known in the art and are similar in principal to methods which are used to create GST fusion proteins according to the present invention. These methods are all well known.

In a preferred embodiment according to the present invention, one or more positions or substituents on binding partners (or, fused proteins) according to the present invention are derivatized or labeled to chemically link a small fluorescent moiety. In this aspect of the invention, at a position or functional group substituent of a binding partner of a fused protein or its derivative (or a fused protein), a fluorescent dye may be attached to the compound through a chemical linker from through carbon (carbon-carbon), amide, ester, ether, or $S(O)_n$ (where n=0, 1 or 2) bonds, among others. Representative fluorescent dyes include fluorescein, Alexa, Bodipy, Cyanin, coumarin, Dansyl, rhodamine and pyrene, among others. Specific fluorescent dyes to be used in the present invention include Alex® (350, 405, 430, 488, 500, 514, 532, 546, 555, 568, 594, 610, 633, 647, 660, 680, 700 and 750), AMCA-X, Bodipy® (630/650, 650/665, FL, TMR, TR), Cascade Blue®, Dinitrophenyl, fluorescein (FAM), HEX, JOE®, cyan, Marina Blue®, Oregon Green® (488 and 514), Pacific Blue®, Pacific Orange®, Rhodamine Green®, QSY® (7, 9, 21 and 35), ROX, Rhodamine Red®, TET, Tetramethylrhodamine (TAMRA) and Texas Red®, among others, available from suppliers such as Invitrogen, Ltd (UK) and Molecular Probes, Inc. (Eugene, Oreg.), among others. One of ordinary skill will readily be able to derivatize linking parts (or fused proteins) according to the present invention and link them through the above-referenced groups to fluorescent moieties to provide fluorescent versions of binding partners according to the present invention. Once bound these binding partners may be used in flow cytometry to assist in qualifying and quantitying one or more compounds as potential drugs as agonists, antagonists, or regulators (allosteric) of the fused protein. This approach represents a viable approach to finding molecules which can influence fused proteins and potential drugs for disease states which are mediated through the target fused protein.

In this aspect of the invention, a known (or determined) binding partner of a fused protein is conjugated or linked to one or more of the above-described fluorescent dyes. In one aspect of the invention, compounds according to the present invention may by synthesized which contain or are modified to contain nucleophilic functional groups such as OH, SH, $NH_2$, which are coupled with reactive dyes containing electrophilic functional groups. The result is a conjugated fluorescently labeled compound according to the present invention. In another aspect of the invention, compounds according to the present invention which contain or are modified to contain electrophilic functional groups including aldehydes, ketones, maleimide, epoxide, carboxylic acid or esters, may be coupled with nucleophilic reactive dyes to produce fluorescently labeled compounds according to the present invention. Alternatively, compounds according to the present invention which contain or are modified with or to contain bifunctional linkages such as aminohexanoic acid, succinic acid, etc. are coupled with a reactive dye accordingly to produce fluorescently labeled compounds according to the present invention. This chemistry is well developed in the art.

Examples of Reactive Fluorescent Dyes:

Amine reactive:
Fluorescein isothiocyanate
[Tetramethylrhodamine-5-(and-6)-isothiocyanate]
[6-(Fluorescein-5-carboxamido)hexanoic acid, succinimidyl ester]

[5-(and-6)-Carboxyrhodamine 6G, succinimidyl ester]
[5-(and-6)-Carboxytetramethylrhodamine, succinimidyl ester]
[6-(Tetramethylrhodamine-5-(and-6)-carboxamido) hexanoic acid, succinimidyl ester]
[5-(and-6)-Carboxyfluorescein, succinimidyl ester]
1-pyrenebutanoic acid succinimidyl ester
7-Hydroxy-4-methylcoumarin-3-acetic acid, succinimidyl ester
7-Methoxycoumarin-3-carboxylic acid, succinimidyl ester
[6-((7-Amino-4-methylcoumarin-3-acetyl)amino)hexanoic acid, succinimidyl ester]
[5-Dimethylaminonaphthalene-1-sulfonyl chloride]
[Tetramethylrhodamine-5-iodoacetamide]
[5-((((2-Iodoacetyl)amino)ethyl)amino)naphthalene-1-sulfonic acid]
[6-Bromoacetyl-2-dimethylaminonaphthalene]

Thiol reactive
[N-(7-Dimethylamino-4-methylcoumarin-3-yl)maleimide]

Aldehyde, ketone (electrophilic) reactive

Sulforhodamine 101 hydrazide

"Antagonist" as used herein is meant to refer to an agent that down-regulates (e.g., suppresses or inhibits) at least one activity of a compound, e.g., the binding of a binding partner of a fused protein to the fused protein. In general, in the present invention an antagonist prevents or inhibits the binding of a labeled binding partner to the fused protein in the GST fusion protein. An antagonist can be a compound which inhibits or decreases the interaction between a protein and another molecule, e.g., a target peptide or enzyme substrate. An antagonist can also be a compound that downregulates expression of a gene or which reduces the amount of expressed protein present.

The term "regulator" as used herein is meant to refer to an agent which binds to the fused protein and influences the activity of the fused protein. Technically, a regulator (allosteric) is neither an agonist nor antagonist, but is an agent which binds to the fused protein and otherwise influences the fused protein's activity.

The term "agonist", as used herein, is meant to refer to an agent that mimics or upregulates (e.g., potentiates or supplements) an activity of a fused protein. An agonist can be a wild-type protein or derivative thereof having at least one bioactivity of the wild-type protein, but preferably is a small molecule, more preferably a potential drug. An agonist can also be a compound that upregulates or which increases at least one bioactivity of a protein. An agonist can also be a compound which increases the interaction of the fused protein such as a polypeptide with another molecule, e.g., a target peptide, nucleotide or nucleic acid.

The term "DNA sequence encoding a polypeptide" refers to any nucleic acid that encodes a polypeptide, including, e.g., a cDNA, a cDNA fragment, a genomic DNA, a genomic DNA fragment, and a synthetic DNA. Moreover, certain differences in nucleotide sequences may exist between individual organisms, of the same or different species, which are called alleles. Such allelic differences may or may not result in differences in amino acid sequence of the encoded polypeptide yet still encode a polypeptide with the same biological activity.

The term "equivalent", with respect to a nucleotide sequence, is understood to include nucleotide sequences encoding functionally equivalent polypeptides. Equivalent nucleotide sequences will include sequences that differ by one or more nucleotide substitutions, additions or deletions, such as allelic variants and therefore include sequences that differ due to the degeneracy of the genetic code. "Equivalent" also is used to refer to amino acid sequences that are functionally equivalent to the amino acid sequence of a mammalian homolog of a protein, but have different amino acid sequences, e.g., at least one, but fewer than 30, 20, 10, 7, 5, or 3 differences, e.g., substitutions, additions, or deletions.

"Homology", "homologs of", "homologous", or "identity" or "similarity" refers to sequence similarity between two polypeptides or between two nucleic acid molecules, with identity being a more strict comparison. Homology and identity can each be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e., structurally related, at positions shared by the amino acid sequences. An "unrelated" or "non-homologous" sequence shares less than 40% identity, though preferably less than 25% identity, with one of the sequences of the present invention.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences. Other techniques for determining sequence identity are well-known and described in the art.

The term "interact" as used herein is meant to include detectable interactions (e.g., biochemical interactions) between molecules, such as interaction between protein-protein, protein-nucleic acid, protein-nucleotide and protein-small molecule in nature.

As used herein, the term "nucleic acid" refers to polynucleotides such as deoxyribonucleic acid (DNA), and, where appropriate, ribonucleic acid (RNA). The term also includes, as equivalents, analogs of RNA or DNA made from nucleotide analogs, and single (sense or antisense) and double-stranded polynucleotides. ESTs, chromosomes, cDNAs, mRNAs, and rRNAs. The term "nucleotide sequence complementary to the nucleotide sequence of SEQ ID NO. "x" refers to the nucleotide sequence of the complementary strand of a nucleic acid strand having SEQ ID NO. x. The term "complementary strand" is used herein interchangeably with the term "complement". The complement of a nucleic acid strand can be the complement of a coding strand or the complement of a noncoding strand.

As used herein, the term "promoter" means a DNA sequence that regulates expression of a particular DNA sequence operably linked to the promoter, and which effects expression of the particular DNA sequence in cells. The term encompasses "tissue specific" promoters, i.e., promoters which regulate expression of the selected DNA sequence as a function of cellular state, e.g., differentiation state. Typically tissue specific promoters are active only in specific cells (e.g., cells of a specific tissue). The term also covers so-called "leaky" promoters, which regulate expression of a selected DNA primarily in one tissue, but cause expression in other tissues as well. Other promoters that can be used include non-tissue specific promoters and promoters that are constitutively expressed or that are inducible (i.e., expression levels can be controlled). The terms "protein", "polypeptide", and "peptide" are used interchangeably herein to refer to a polymer of amino acids. However, a protein may include more than one polypeptide chain. A polypeptide can be a gene product, although some polypeptides can be produced synthetically.

The term "recombinant protein" refers to a polypeptide of the present invention which is produced by recombinant DNA techniques. In an exemplary method, DNA encoding a polypeptide is inserted into a suitable expression vector which is in turn used to transform a host cell to produce the heterologous protein. In another exemplary method, homologous recombination is used to insert a heterologous regulatory sequence into an endogenous gene. Moreover, the phrase "derived from", with respect to a recombinant gene, is meant to include within the meaning of "recombinant protein" those proteins having an amino acid sequence of a native polypeptide, or an amino acid sequence similar thereto which is generated by mutations including substitutions and deletions (including truncation) of a naturally occurring form of the polypeptide.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon-containing) or inorganic molecules.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' 0-methyl rather than phosphodiesterase linkages within the oligodeoxyribonucleotide backbone.

A "compound" or "test compound" can be any chemical compound, for example, a macromolecule (e.g., a polypeptide, a protein complex, or a nucleic acid) or a small molecule (e.g., an amino acid, a nucleotide, an organic or inorganic compound). The test compound can have a formula weight of less than about 10,000 grams per mole, less than 5,000 grams per mole, less than 1,000 grams per mole, or less than about 500 grams per mole. The test compound can be naturally occurring (e.g., a herb or a nature product), synthetic, or both. Preferably, the term compound refers to a small molecule which is being tested to determine whether or not it has agonist or antagonist activity vis-à-vis the binding of the binding partner to the fused protein.

Examples of macromolecules are proteins, protein regulatory domains, protein complexes, and glycoproteins, nucleic acids, e.g., DNA, RNA (e.g., double stranded RNA or RNAi) and PNA (peptide nucleic acid). Examples of small molecules are peptides, peptidomimetics (e.g., peptoids), amino acids, amino acid analogs, polynucleotides, polynucleotide analogs, nucleotides, nucleotide analogs, organic or inorganic compounds e.g., heteroorganic or organometallic compounds. One exemplary type of protein compound is an antibody or a modified scaffold domain protein. A test compound can be the only substance assayed by the method described herein. Alternatively, a collection of test compounds can be assayed either consecutively or concurrently by the methods described herein.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity, in the present case, inhibitory (antagonist), agonist or regulatory (allosteric) activity vis-à-vis the fused protein. The compounds thus identified can serve as conventional "lead compounds" for further combinatorial synthesis and structure activity relationship generation or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like). Additional examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Some exemplary libraries are used to generate variants from a particular lead compound. One method includes generating a combinatorial library in which one or more functional groups of the lead compound are varied, e.g., by derivatization. Thus, the combinatorial library can include a class of compounds which have a common structural feature (e.g., framework).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

The test compounds of the present invention can also be obtained from: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al., (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological libraries include libraries of nucleic acids and libraries of proteins or regulatory domains thereof. Some nucleic acid libraries encode a diverse set of proteins (e.g., natural and artificial proteins; others provide, for example, functional RNA and DNA molecules such as nucleic acid aptamers or ribozymes. A peptoid library can be made to include structures similar to a peptide library. (See also Lam (1997) *Anticancer Drug Des.* 12:145). A library of proteins and protein domains may be produced by an expression library or a display library (e.g., a phage display library).

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310).

EXAMPLES

Glutathione Conjugated Beads

In the present methods dextran beads suitable for flow cytometry were derivatized with glutathione. A fusion protein of glutathione-S-transferase and green fluorescent protein (GST-GFP) was used to define kinetic and equilibrium binding characteristics of GST fusion proteins to glutathione beads. Free glutathione competes with this binding, and this competition was used to measure free glutathione concentration.

Results of this experiment showed a ten microliter assay can measure five microliters of twenty micromolar glutathione (100 pmol glutathione) in two hours by flow cytometry. This concentration is two orders of magnitude lower than cellular glutathione concentrations, and three orders of magnitude lower than affinity chromatography eluates. One important result is that by generating high site density, the GST fusion proteins can be constrained to the surface of one bead without hopping to the next bead in multiplex assays, an important feature for high flow cytometry.

Thus, glutathione in cellular lysates and GST-fusion protein affinity chromatography eluates can be measured by flow cytometry. Many interactions between GST fusion proteins and their fluorescent binding partners may be quantifiable by flow cytometry. Although a system may have the disadvantage that it has a low affinity and a correspondingly quick off-rate in solution, it may remain on beads if the site density can be increased to offer a slow apparent off rate. This is an unexpected result of the present invention.

In the present study, beads of a size suitable for flow cytometry were derivatized with glutathione (GSH beads), and used to measure directly the binding of a fusion protein composed of glutathione-S-transferase and enhanced green fluorescent protein (GST-GFP). Free GSH competes with GST-GFP binding, and the competition can serve as an assay for GSH. The assay is useful for ensuring the adequate removal of free GSH from GST fusion protein preparations that have been eluted from a glutathione column with millimolar concentrations of GSH. Removal of GSH is important for applications necessitating high efficiency rebinding of the affinity purified GST fusion protein to glutathione-derivatized beads. The kinetic and equilibrium binding constants for GST-GFP/GSH determined by flow cytometric assays define the range of interactions that can be quantitatively measured between a GST fusion protein and a binding partner by Western blot, or between a GST fusion protein and a fluorescent binding partner by flow cytometry.

Materials and Methods

All reagents were of analytical quality and unless otherwise noted were from Sigma (sigmaaldrich.com). Plasticware was from VWR (vwr.com). Sephadex G-25, glutathione Sepharose 4B, and Superdex Peptide beads were from Amersham Biosciences (amershambiosciences.com); the Superdex Peptide beads are 13 µm with an exclusion limit of 7,000 Da, and were extruded from a column. Fluorescein was from Molecular Probes (probes.com). Data fitting and analysis were done using Prism software (graphpad.com). Bead fluorescence at a given voltage for FL1 was determined by reference to beads with calibrated in thousands of mean equivalents of soluble fluoresceins, (kMESF), from Bangs Labs (bangslabs.com).

Expression and Affinity Purification of GST-GFP

Briefly, the GST-GFP vector was constructed, expressed in *E. coli* and affinity purified on GSH-Sepharose as follows. The vector encoding GST-GFP was constructed by inserting an EcoRI-NotI fragment from pEGFP—N2 (Becton-Dickinson Biosciences; www.bdbiosciences.com) into pGEX-6P-1 (Amersham Biosciences) using standard recombinant DNA techniques. Transformation of *E. coli* strain BL21(DE3) containing the plasmid pLysS with this vector gave a fusion protein with a 30 amino acid linker. 200 µl of an overnight culture of the transformed bacteria was diluted to 20 ml in fresh LB broth with 50 µg/ml ampicillin and 5 µg/ml chloramphenicol, and grown at 37° C. to 0.6 absorbance at 595 nm. For the induction of expression of the fusion protein, 0.25 mM IPTG was added and further incubated for 4-5 hrs at 30° C. The cells were then collected by centrifugation, resuspended in 2 ml of water, and frozen in 0.5 ml aliquots at −80° C. An aliquot was thawed, bacteria were carefully lysed (without foaming) using a Branson Sonicator 250 at a '3' setting with 15 bursts of 0.5 second, and the lysate was cleared by centrifugation in a microcentrifuge at 18,000×g for ten minutes. The supernatant was freed from small molecules by gel filtration using a 5 ml column of Sephadex G-25 in 30 mM HEPES, pH 7.5, 100 mM KCl, 20 mM NaCl, 1 mM EDTA. For affinity purification, this was applied to a 0.2 ml column of glutathione Sepharose 4B. The column was rinsed with 0.4 ml of buffer, then eluted with 5 mM glutathione in buffer and collected by eye. The affinity-purified GST-GFP was again passed through the gel filtration column that had been rigorously cleaned following the manufacturer's protocol to remove the majority of free GSH. This $2^{nd}$ gel filtrate was then concentrated to 40 µl using a Microcon YM-30, the retentate was washed twice with fresh buffer, and each of the three Microcon YM-30 filtrates was tested for glutathione as indicated in FIG. 1. Ethylene glycol was added to 40% by volume of the final retentate, the concentration of GST-GFP was determined by fluorimetry using fluorescein as a standard, and the preparation was stored at −20° C. for three months without noticeable degradation.

Synthesis of GSH Beads

Briefly, Superdex Peptide beads were extruded from a column, activated with a water-soluble bis-epoxide, and then coupled to glutathione. (Other derivatives of these beads have been used for flow cytometry previously (8,9).) One milliliter of a 50% slurry of beads in 20% ethanol was reduced to a wet cake using a 15 ml coarse sintered glass filter, and washed three times with 15 ml water to remove the ethanol. The wet cake was transferred to a small screw-cap tube, and the filter was rinsed with 0.3 ml of water which was added to the tube. The beads were suspended by vortexing, then 60 µl of 10 M NaOH and 300 µl of 1,4-butanediyl diglycidyl ether (formerly butanediol diglycidyl ether) were added, and the suspension was rocked gently at 40° C. for 4 h. The epoxy-activated beads were rinsed four times on the filter. For the preparation of high site density beads, 600 µl of 100 mM glutathione in 100 mM sodium phosphate, pH re-adjusted to 7.5, 1 mM EDTA, was added to the epoxy-activated beads. The beads were kept in suspension for 16 h at 40° C., then rinsed twice with 0.01% dodecyl maltoside. Low site density beads were prepared using 20 mM GSH and reacted for 2 h; by decreased concentration of GSH and time of reaction we expected 40 fold less derivitization, but we obtained about one eighth the site density of GSH found on the high site density beads. The remaining active sites were blocked with 1% 2-mercaptoethanol for 2 h. The beads were rinsed twice, then stored in 30 mM HEPES, pH 7.5, 100 mM KCl, 20 mM NaCl, 1 mM $MgCl_2$ (HPSM) with 0.01% dodecyl maltoside and 0.02% $NaN_3$ at 4° C. as a 50% slurry, which corresponds to ~2.5×10$^5$ beads per microliter, or 25 assays of 10$^4$ beads each per microliter.

Protocols for Measurement of Bead Fluorescence

Figure 3:
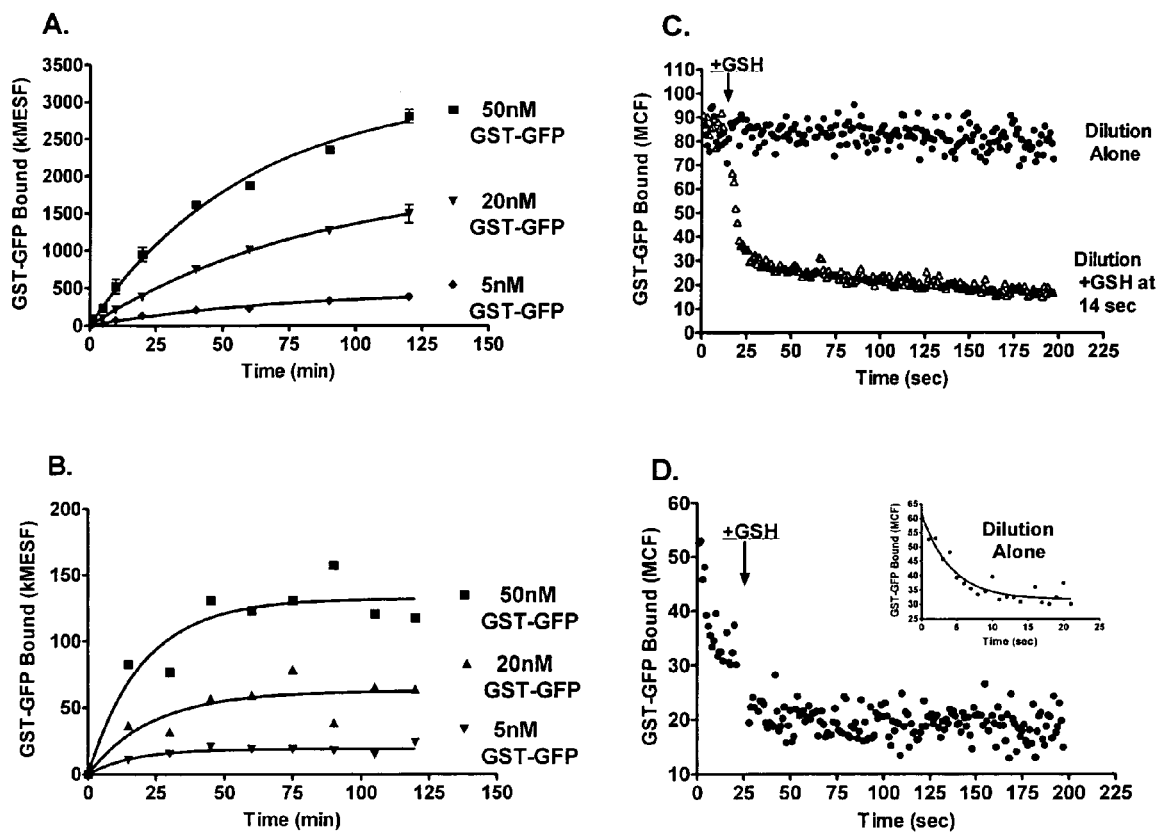
FIG. 3 shows the rates of GST-GFP binding and dissociation. A: GST-GFP, at concentrations of 5, 20, and 50 nM, was used to assess the approach to equilibrium at 4° C. for high site density beads. B. The approach to equilibrium was studied for the low site density beads as above. C: 10 nM GST-GFP was allowed to bind to high site density GSH beads for 2 h as above. Using the kinetic mode of the cytometer, beads were diluted and in the first experiment, and loss of fluorescence due to dilution alone was monitored (O). In the second experiment, bead fluorescence was monitored for ten seconds, the tube was removed, GSH was added to 1 mM and mixed, and the tube was returned to the cytometer to monitor loss of bead fluorescence due to GSH competition (A). The time of addition of GSH was estimated to be 14 sec. D: Low site density glutathione beads were loaded with 100 nM GST-GFP for two hours. The beads were then diluted as above, and loss of fluorescence was apparent within the first 21 seconds. The tube was then removed, GSH was added to 1 mM, and the tube was returned to the cytometer again. The inset shows the fit of the first 21 seconds of data to a calculated off-rate due to dilution alone.

For the high site density beads, suspensions of 10$^4$ beads were made in 10 µl of HPSM buffer with 0.01% dodecyl maltoside added to reduce nonspecific binding. GST-GFP with or without competitor was included at the desired concentration, and the suspension was shaken in a 96 V-bottomed well plate (Corning Costar #2897; www.corning.com) for the desired amount of time at 4° C. The suspensions were then diluted with 190 µl of buffer, and immediately transferred into a tube suitable for flow cytometric determination of bead fluorescence. Data was collected from 500 beads per sample in duplicates. For the high site density beads, bead-bound fluorescence remains stable during the time (20-30 seconds) necessary to count the 500 beads (FIG. 3B). However, with low site density beads dilution with the buffer resulted in dissociation of bead-bound fluorescence during the measurements (FIG. 3C inset). Therefore, we adopted a direct reading protocol for fluorescence measurement from low site density beads as follows. Instead of 10 µl, we used 40 µl of HPSM buffer with 0.01% dodecyl maltoside to suspend 10$^4$ beads. After incubation of the samples with shaking as above, the suspensions were transferred into small tubes placed inside tubes suitable for flow cytometers, and bead fluorescence data was immediately collected from 500 beads in duplicates. To ensure that the background (unbound) plus bead-bound fluorescence in the undiluted samples did not saturate the cytometer's phototube and give erroneously low bead fluorescence, it was necessary to reduce the voltage of FL1, keeping the fluorescence in the linear range.

Free Glutathione Assay

The standard assay for monitoring the concentration of free glutathione was performed in ten microliters of HPSM buffer with 0.01% dodecyl maltoside added to reduce nonspecific binding. Typically, two microliters of 50 nM GST-GFP and two microliters of bead suspension containing 10,000 beads (as determined using a hemacytometer) were added to six microliters of buffer, with or without some competitor, giving 10 nM GST-GFP in the suspension. The ten microliter assays were gently shaken in wells of a 96 V-shaped well plate (Corning Costar #2897) on a vortex mixer in a cold room for two hours. The suspensions were diluted with 190 µl of buffer immediately before flow cytometric determination of bead fluorescence, collecting data from 500 beads; the signal did not fall significantly due to dilution during the time of data collection, about 10-20 seconds (FIG. 3B), except with the low site density beads (FIG. 3C inset), which were not used for this determination.

Dissociation Rate Determinations

Beads were loaded with GST-GFP for two hours as above. The suspension was then diluted and the bead fluorescence was determined with the flow cytometer in the kinetic mode. The data were converted to ASCII format using IDLQuery (software available free from the authors). Raw data was binned over one second intervals, MCF (mean channel flourescence) values were calculated for each bin, and the results were exported and graphed using Prism. For control measurements, the tube of diluted beads was removed from the cytometer, excess GSH was added and mixed, and the tube was replaced on the cytometer.

Results

Flow Cytometric Assessment of GST-GFP Binding

Superdex Peptide beads were derivatized to display GSH as described in Materials and Methods. These 13 μm beads have small pores which exclude proteins greater than about 7,000 Daltons. GST-GFP was constructed and expressed as described in Materials and Methods. Initially, a crude bacterial lysate containing GST-GFP was cleared of contaminating small molecules by centrifugation to one tenth volume in a Microcon YM-30 filter, followed by replacement of buffer, three times. Because this method, designed to remove cellular GSH from the lysate, resulted in aggregation or gelling of the GST-GFP protein, we found it necessary to use gel filtration to remove the GSH from lysates in later experiments, as described in Materials and Methods. A standard binding assay of ten microliters was used to assess the binding of the crude, cleared GST-GFP onto high site density glutathione beads and underivatized beads, using about 50 nM (final concentration) GST-GFP. After two hours of mild shaking on a vortex mixer at 4° C., the 10 microliters of suspension was diluted to two hundred microliters for flow cytometric determination of bead fluorescence. A final concentration of 50 nM crude GST-GFP alone in the ten microliter assay gave about 2.4 million MESF (2,400 kMESF), as shown in the first bar of FIG. 1. The addition of two microliters of each of the filtrates, or two microliters of 5 mM GSH, decreased the binding, as expected, and binding to the underivatized dextran beads was negligible, again as expected (FIG. 1).

Equilibrium $K_d$ of GST-GFP for GSH Beads and for Free GSH

Figure 2:
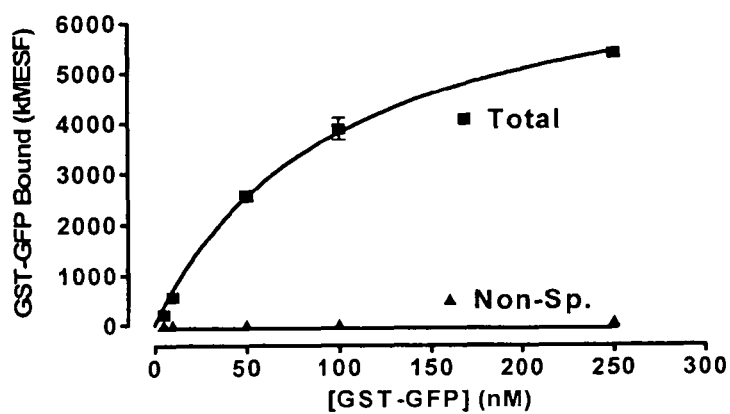
FIG. 2 shows GST-GFP binding to GSH beads in the absence and presence of soluble GSH competitor. A: Affinity-purified GST-GFP was used with the dilution protocol to obtain binding curves in the absence (total) and presence (non-specific) of 1 mM GSH, using high site density beads. B. Affinity-purified GST-GFP was used in the direct reading protocol to obtain binding curves as above, using low site density beads. C: 10 nM GST-GFP was used in the dilution protocol with increasing amounts of GSH to obtain a competition curve with high site density beads.
Figure 2:
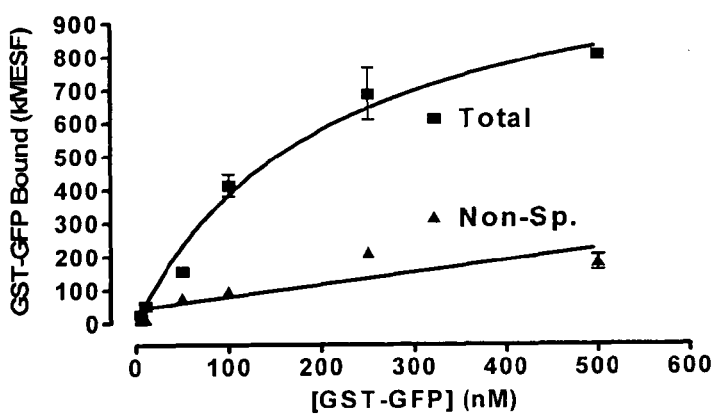
Figure 2:
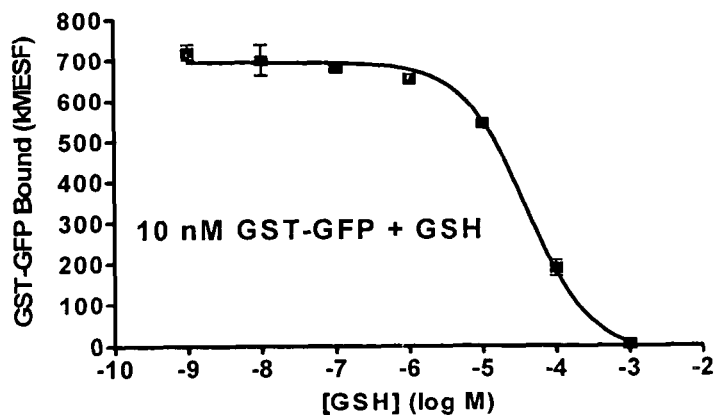

GST-GFP was affinity purified and cleared of contaminating GSH by gel filtration followed by concentration using ultrafiltration as described in Materials and Methods. An equilibrium binding experiment was carried out with varying concentrations of GST-GFP mixed for two hours with high site density beads. The beads suspensions were diluted at the cytometer to obtain bead fluorescences (see Materials and Methods), which were then analyzed to obtain a $K_d$ of 100 nM for the binding of GST-GFP to high site density GSH beads (FIG. 2A). This experiment was repeated with different preparations of GST-GFP, and the $K_d$ was determined to be 108 nM +/−47 nM (constants are collated in Table 1). The $B_{max}$ for these experiments was 7.1 million MESF +/−0.8 million. This represents 50% total surface coverage, about that expected from random fall onto a surface, if GST-GFP has a Stokes diameter of ~7 nm. The 5 million fluorophores found at 250 nM GST-GFP on a 13 μm bead might be expected to exhibit some self quenching, but the present study did not rigorously determine how much. Non-specific binding was negligible, even in the presence of 250 nM GST-GFP.

TABLE 1

Constants measured in this report.

| | HIGH SITE DENSITY BEADS | | LOW SITE DENSITY BEADS | |
| --- | --- | --- | --- | --- |
| Bmax (2 hours) | $7.1 \times 10^6$ GST-GFP/bead | | $8.6 \times 10^5$ GST-GFP/bead | |
| Kd (2 hours) | 108 nM | 80 nM av. | 190 nM | 220 nM av. |
| Kd (approach to equilibrium) | 50 nM | | 250 nM | |
| kf (approach to equilibrium) | $2.6 \times 10^3$ M-1 sec-1 | | $2.6 \times 10^3$ M-1 sec-1 | |
| kr (approach to equilibrium) | $1.3 \times 10^{-4}$ sec-1 | | $6.4 \times 10^{-4}$ sec-1 | |
| koff (dilution) | $\sim 1.3 \times 10^{-4}$ sec-1 | | 0.24 sec-1 | |
| koff (+GSH) | 0.23 sec-1 | | 0.22 sec-1 | |

Low site density beads did not give a steady fluorescence upon dilution (FIG. 3D), and a direct reading protocol was developed for these beads as detailed in Materials and Methods. The beads suspensions were larger (40 μl compared to 10 μl in the dilution protocol), and the bead fluorescences were read directly, not after dilution, at the cytometer. An equilibrium binding experiment for low site density beads was carried out as for the high site density beads, and is shown in FIG. 2B. The overall non-specific binding was higher, as expected using a direct reading, and the quality of data was a bit lower. The measured $K_d$ was 190 nM, larger but within a factor of two of the 108 nM obtained with high site density beads, and the measured $B_{max}$ was 0.86 million sites per bead, one eighth of the 7.1 million sites per high site density beads obtained above.

Using 10 nM GST-GFP, varying amounts of GSH were added to obtain a competition curve (FIG. 2C) using high site density beads. An $EC_{50}$ of $3.9 \times 10^{-5}$ M was obtained, and using the $K_d$ for GST-GFP binding to the beads with the Cheng-Prusoff approximation, a $K_i$ of $3.5 \times 10^{-5}$ M was calculated. The manufacturer's information for GST gives a $K_m$ for glutathione of $5 \times 10^{-3}$ M; we found the $K_i$ for free glutathione to be $3.5 \times 10^{-5}$ M, and the $K_d$ for the glutathione-linker on the bead to be $1.1 \times 10^{-5}$ M. These numbers will be compared in the Discussion. Using this curve to evaluate the filtrates obtained in FIG. 1, it appears that the "gelling" referred to above interfered with mixing, for filtration 2 reduced the free GSH concentration by only a factor of about two, rather than the factor of ten expected by volume: filtrate 1 corresponds to about $8 \times 10^{-4}$ M; filtrate 2 corresponds to about $4 \times 10^{-4}$ M; and filtrate 3 corresponds to about $4 \times 10^{-5}$ M. Note also that when using commercial large-pore glutathione beads for affinity purification, which have a thousand fold higher binding capacity, just adding more beads would quickly overwhelm the free GSH and bind most of the GST fusion protein.

Kinetics of Binding and Dissociation

GST-GFP binding to glutathione beads was examined by adding different concentrations of GST-GFP (5, 20, and 50 nM) to high site density beads and following the approach to equilibrium in bead fluorescence (FIG. 3A). The observed data were analyzed using the program Scientist (MicroMath™ Software; www.micromath.com). A single site binding model was utilized to fit the data, and the forward binding rate constant and reverse binding rate constant for high site density beads were obtained by fitting the three data sets simultaneously. The concentration of GSH on the beads was calculated using 7.1 million sites per bead and 10,000 beads in 10 μl, giving 12 nM GSH. The forward rate constant, $k_f$, was calculated to be $2.58 \times 10^3$ M$^{-1}$ sec$^{-1}$, and the reverse rate constant, k was calculated to be $1.3 \times 10^{-4}$ sec$^{-1}$. These numbers are both low compared to the constants obtained for the binding of $F_{ab}$ fragments to epitopes on cells, both partners comparably sized (10), and the likely reasons for this will be explored in the Discussion. The ratio of $k_r/k_f=K_d$ is then $5.04 \times 10^{-8}$ M, or one half that determined by the two hour 'equilibrium' binding seen in FIG. 2A. These are within experimental error; we shall use the average of these two numbers, 80 nM, as the $K_d$ for the high site density beads.

The same kinetic approach to equilibrium experiment was carried out for the low site density beads, FIG. 3B. The concentration of GSH on these beads in this experiment was calculated using $8.6 \times 10^5$ GSH per bead, and 10,000 beads in 40 µl, giving 0.36 nM GSH. Again, the quality of the data is lower, but a good fit was obtained by keeping the forward rate constant the same while increasing the reverse rate constant by a factor of five to $6.4 \times 10^{-4}$ sec$^{-1}$. The ratio of $k_r/k_f=K_d$ is then 250 nM, close to the 190 nM obtained in the equilibrium binding experiment. We will use the average of these two numbers, 220 nM, as the $K_d$ for the low site density beads.

The dissociation of GST-GFP from glutathione beads was examined in two ways: by the standard twenty fold dilution alone, and by dilution followed by addition of excess glutathione. High site density beads were coated with 10 nM GST-GFP as above, then diluted as usual for flow cytometric determination of bead fluorescence in the kinetic mode (FIG. 3C, •: each mark shows the mean channel fluorescence of the beads passing in one second). It can be seen that little fluorescence was lost over a period of three minutes, which shows that during the typical data collection period of 10-20 sec there is no large time-dependent loss of bead-bound GST fusion protein. The reverse rate constant for this 'dilution alone' experiment was not accurate, due to the small fraction of fluorescence which dissociated in the experiment, but was compatible with the reverse rate constant from the approach to equilibrium experiment of $1.3 \times 10^{-4}$ sec$^{-1}$. In the second type of experiment, an initial fluorescence was obtained for 10 seconds, the tube was removed from the cytometer, glutathione was added to 1 mM and mixed, and the tube was returned to the cytometer. We measured the time to mix the glutathione as four seconds, and have added the average of the first ten seconds as the 11-14 second data points. These data show a dramatic decrease in bead fluorescence (FIG. 3C, Δ) following glutathione addition. This gave a reverse rate constant of 0.23 sec$^{-1}$, closer to that expected for solution kinetics, and about 1,800 times faster than the reverse rate constant observed by dilution alone. This apparent discrepancy will be explored in the Discussion.

Similar experiments were performed on beads with about 8 fold less glutathione sites per bead, FIG. 3D. Using the low site density GSH beads, the bead-associated GST-GFP fluorescence dropped rapidly upon dilution alone, and quickly reached a resting value when glutathione was added. Analysis to obtain the reverse rate constant, shown in the inset to FIG. 3D, gave a value of 0.24 sec$^{-1}$, almost identical to the reverse rate constant obtained when GSH was added to the high site density beads in FIG. 3C. Note that this would appear to be the rate of dissociation in solution, with a half time of about 3 seconds.

Figure 4:
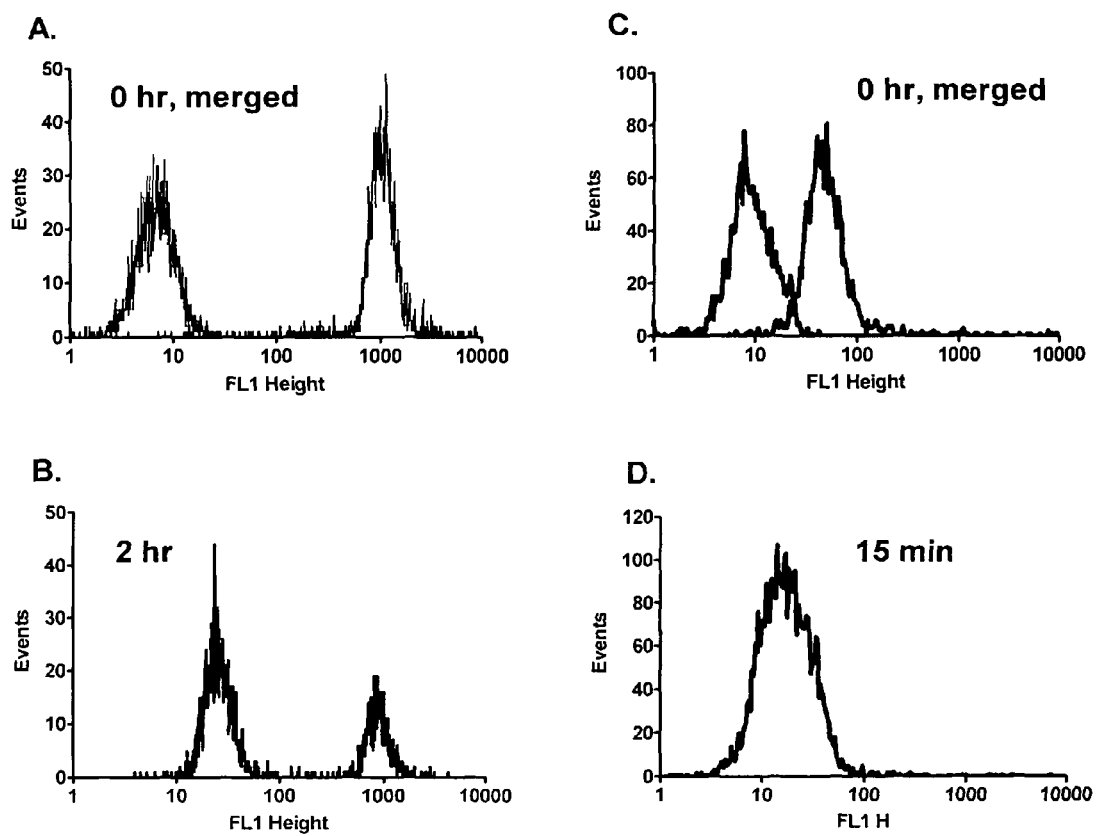
FIG. 4 shows GST-GFP bead hopping. A: One set of high site density beads was left untreated, giving an autofluorescence of 7 MCF. A second set of beads was loaded with 10 nM GST-GFP for two hours and washed. The histograms of both sets of beads are shown merged. B: The two sets of beads were gently shaken together with 13,000 of the empty beads plus 5,000 of the loaded beads in 10 µl of solution for 2 h at 4° C. The resulting histogram is shown; the low MCF was 27.2. C. A set of $10^4$ low site density beads was read to determine autofluorescence. A second set was suspended with 40 µl of 50 nM GST-GFP for two hours and read, then the supernatant was removed. The histograms of both sets of beads are shown merged. D. The two sets of beads were mixed together for minutes at 4° C., then the bead fluorescence was read.

The results above suggested that GST-GFP that had been loaded onto one set of high site density beads would not transfer significantly to other unloaded high site density beads during our typical two hour incubation. To monitor the transfer of GST-GFP from one bead to another, duplex assays were performed using different sets of beads. One set of beads was loaded with 10 nM GST-GFP and washed as above, giving 1160 MCF, while a second set was left uncoated, resulting in 8.1 MCF autofluorescence (FIG. 4A). The beads were mixed together for 2 hours at 4° C., and the resulting histogram displayed two widely separated peaks (FIG. 4B). Note that in this experiment, it was not necessary to color one set of beads red in order to distinguish one set of beads from the another. Only four percent of the fluorescence from the coated set of beads transferred to the uncoated beads (based on equal numbers of beads of each type being used). The low amount of transfer confirms the low reverse rate constant observed with high site density beads by dilution alone. In a second experiment, $2.5 \times 10^5$ beads (enough for 25 typical experiments) were loaded in the same manner and washed four times with 200 µl of buffer: they lost only 5% of their fluorescence. Thus, high GSH surface density beads can be washed to reduce nonspecific binding, and can be multiplexed to allow two or more measurements to be monitored in the same suspension. These results demonstrate that care must be taken to use high GSH surface density beads for assays designed to measure protein-protein interactions. Under conditions of high site density, the GST-GFP has a slow apparent dissociation rate, due to a high probability of immediate rebinding after dissociation to one of the many free binding sites on the same bead.

A similar experiment was performed using low site density beads. In FIG. 4C, it can be seen that the equilibrium bound value of GST-GFP was lower at the start, about 50 MCF, and the autoflourescence was the same at the start, compared to the high site density beads. When the supernatant of the beads with GST-GFP was removed, and the beads were resuspended with the other bead suspension, however, the transfer of fluorescence resulted in a merging of the two histogram peaks within 15 minutes, FIG. 4D. This rapid transfer indicates that low GSH surface density beads cannot be washed or multiplexed.

Discussion

We report equilibrium and kinetic data for the interaction of GST-GFP with glutathione beads using flow cytometry, which should be applicable to most GST fusion proteins. From this a new flow cytometric assay for glutathione was developed that can detect, for example, five microliters of $2 \times 10^{-5}$ M glutathione (100 pmol), two orders of magnitude lower concentration than that found in most cells. It was used to determine the level of glutathione contaminants which would interfere with the binding of a GST fusion protein to GSH beads. Many assays for glutathione exist which are more sensitive than the one given in this report (11); a table in this reference cites HPLC fluorometry and electron capture methods with a sensitivity of about 1 pmol, and special methodology taking sensitivity down to 2-20 fmol. A colorimetric kit has a sensitivity of 30 pmol (biovision.com), but lacks the biological specificity inherent in our assay, or the HPLC specificity of the referenced assays.

There are three large gaps between pairs of numbers which are expected to be the same in our data: 1) the $K_m$ of GST for GSH is reported as $5 \times 10^{-3}$ M but the $K_d$ for free GSH is $3.5 \times 10^{-5}$ M; 2) the $K_d$ for free GSH is $3.5 \times 10^{-5}$ M but the $K_d$ for the GSH-linker on the low site density beads is $2.2 \times 10^{-7}$ M; and 3) the $k_{off}$ for dilution alone on high site density beads is $1.3 \times 10^{-4}$ sec$^{-1}$ but the $k_{off}$ using addition of GSH on high site density beads and for dilution alone on low site density beads is 0.23 sec$^{-1}$. We suggest that the first gap can be rationalized by noting that enzymes use some substrate binding energy to stabilize the transition state, so it is expected that the $K_d$ for GSH in the absence of the second substrate (for example, dinitrofluorobenzene) is lower than the $K_m$ for GSH. The second gap can be resolved by assuming that GST binds to the glutathione linker more strongly than to free GSH. The third gap can be interpreted as evidence that GSH residues on the high site density beads are close enough to allow dimer binding. Dimerization of a different GST fusion protein has been shown at $10^{-6}$ M (13) and dimerization of GFP has been shown at $10^{-4}$ M (12), therefore dimerization of GST-GFP might occur at $10^{-8}$ M or less, but is not calculable (14). Dimerization could therefore increase both the affinity of GST-GFP binding to beads with suitably high GSH site density, and the residence time for GST-GFP on such beads, by a factor of $10^4$ or more. Below we show that a factor of 8 in residence time is expected from rebinding, but this still leaves a factor of 180 between the $k_{off}$ of high and low site density beads, and we attribute this to dimerization. The high site density beads have only three fold higher affinity while the reverse rate is 180 fold slower; this may be the result of complex topography or mathematics. We have performed preliminary simulations of off rates of dimers from high site density beads that show a thousand fold difference between dilution alone and dilution with added GSH, but have not been able to calculate $K_d$ values. The influence of covalent dimerization on avidity is complex (15) and a complete theoretical treatment of noncovalent dimers is beyond the scope of this report; our explanations are thus tentative. We note that the higher affinity of GST for bead-bound GSH residues, rather than free GSH, contributes to the widespread use of GSH beads, which bind GST fusion proteins even in the presence of micromolar GSH.

How can a moderate affinity interaction, with a $K_d$ of $5\times10^{-8}$ M, be the basis for the widespread use of GST fusion protein pull-downs? Why don't the fusion proteins dissociate during washing steps? The answer appears to be the high site density of GSH immobilized on the beads, for the off-rate observed for low site density beads is the same as the off-rate observed for high site density beads when millimolar glutathione is added. A lower off-rate can come from dimerization and from rate theory.

When receptors are clustered in space, as when they are confined to the surface of a beads or cell, the rates of binding can be quite different than when they are uniformly distributed in solution. For high surface receptor (here, glutathione) densities, theory predicts that both the forward and reverse rate constants for ligand (here, GST-GFP) binding will be reduced. The forward rate constant is lowered because nearby receptors compete for the same ligand, while the reverse rate constant is reduced because a ligand that dissociates from one receptor has a possibility of rebinding to another free receptor before diffusing away from the surface.

If $k_f$ and $k_r$ are the forward and reverse rate constants for the binding of a ligand to a receptor on a spherical surface, then $$k_r = k_{off}/[1+N k_{on}/4\pi Dr] \quad (1)$$

and $$k_f = k_{on}/[1+N k_{on}/4\pi Dr] \quad (2)$$

where N is the number of free sites (number of GSH molecules) on the beads, D is the diffusion coefficient of the GST-GFP, r is the radius of the bead, and $k_{on}$ and $k_{off}$ are the forward and reverse rate constants of binding of a ligand to a solution receptor (10). [Note that one must convert the units of $k_{on}$ (in $M^{-1}$ $s^{-1}$, or L/mole/s) to $cm^3$/molecule/s (L/mole=1000 $cm^3/6\times10^{23}$ molecules), so that ($N\times k_{on}$) is calculated as (molecules$\times cm^3$/molecule/s), or $cm^3$/s.] Since both rate constants are affected by the same factor, $(k_r/k_f) = (k_{off}/k_{on})$, the dissociation constant is unchanged.

If we assume that the diffusion constant for GST-GFP is $6\times10^{-7}$ $cm^2$/s, the radius of the beads are 6.5 μm, $k_{off}$=0.23/s, $K_d$=80 nM (giving $k_{on}$=2.9$\times10^6$ $M^{-1}$ $s^{-1}$), the theory predicts the reduction in the dissociation rate due to rebinding to be negligible with the low site density beads, but to be reduced by a factor of ~8 with the higher site density beads. However, we observed a 1,000 fold lower rate during dissociation experiments induced by dilution with the high site density beads, leaving us with a factor of about 120 unexplained. In addition to GST-GFP dimerization, there may be additional topographical features that could contribute to the difference, such as GSH being displayed randomly along dextran fibers protruding from the beads at high surface density, rather than randomly on a spherical surface.

When millimolar GSH is used to induce dissociation, rebinding is reduced for high site density beads. This is expected because in the presence of soluble receptors (such as adding GSH to compete with GSH derivatized beads for GST-GFP) equations 1 and 2 are modified such that:

$$k_r = k_{off}/[1+(N k_{on}/(4\pi Dr+(k_{on}Ba^2/D)^{1/2}))] \quad (3)$$

$$k_f = k_{on}/[1+(N k_{on}/(4\pi Dr+(k_{on}Ba^2/D)^{1/2}))] \quad (4)$$

where B is the concentration of free receptors (GSH) used to block rebinding.

There are commercial suppliers of glutathione beads suitable for flow cytometry, and the GST-GFP described here, and most GST fusion proteins, should work equally well for those beads. In the context of flow cytometric quantification of the binding of a GST fusion protein to a fluoresceinated binding partner, both the GST fusion protein and it's binding partner should first be freed from the GSH found in cell extracts or affinity eluates by gel filtration and ultrafiltration, as described above. The fusion protein and its fluoresceinated binding partner can then be added simultaneously to the beads, or the fusion protein can be loaded and washed before addition of the fluoresceinated binding partner. Duplex assays would provide a convenient approach to define the specificity of interaction of one fusion protein on an uncolored set of beads, compared to a second fusion protein bound to a differentially colored set of beads in the same well.

Nominally, the monovalent dissociation rate for GST from GSH on the time frame of seconds would preclude the use of the interaction to permit stable association for capture of assemblies or detection by a flow cytometer. We have presented a special case where the high surface density of the capture reagent leads to a residence time that can be lengthened by several orders of magnitude. This is enough residence time to allow washing and to allow the coated beads to serve as a stable platform for multiplex analysis. For GST pull downs, a high density of GST fusion protein should be attained in order for the binding partners to 'see' a high unoccupied site density, giving the binding partners an enhanced residence time. The principle of enhancing residence time by engineering high unoccupied site density may therefore apply to GST pull downs, immunoprecipitations, and other particle-based methods as well.

Example of Small Molecule Screen: Chemical Library Compounds Modulating Nucleotide Binding to GTPases-Ras and Ras-Related Ras and Ras-related, small molecular weight GTPases function in the regulation of signaling and cell growth control and collectively serve to control cell proliferation, differentiation and apoptosis. There are over 150 known human proteins belonging to the Ras superfamily of GTPases. When mutant or hyperactivated, Ras family members contribute to oncogenesis and hereditary disorders affecting vision, immune and neurologic function. Strategies for inhibiting Ras to date have relied on altering membrane recruitment with drugs affecting prenylation. Inhibition of prenylation enzymes lacks specificity and is problematic because the cellular prenylation machinery is required for the proper function of many Ras superfamily members. The demonstrated efficacy of targeting drugs to the nucleotide binding pocket of specific kinases offers a paradigm that may be applied to the GTPases. The inventors have established a fluorescent GTP-binding assay for GST-GTPase chimeras that can be monitored by flow cytometry. In addition, the method provides the ability to screen multiple GTPases simultaneously with multiplex analysis on a HyperCyt® high throughput flow cytometer. Advantages of the multiplex approach include single step analysis of drug specificity and selectivity, small reaction volumes and the discrimination of free and bound fluorescence that is conservative with respect to reagent usage when compared to polarization assays. The method provides a collection of small Ras-related GTPases as GST-fusion proteins that include members of the Rab, Rho, and Ras families. The present application is directed to methods to identify lead compounds that interfere with fluorescent GTP-binding to individual Ras superfamily members. Subsequent functional assays are then used to identify the compounds as direct and allosteric inhibitors or activators of GTPase function. The identification of small molecule nucleotide binding modulators of small GTPases is expected to have important utility in the future treatment of cancer and neurologic diseases where GTPase function is specifically altered.

The approach identifies inhibitors and activators of small molecular weight GTPases. Ras and Ras-related GTPases are important regulators of cellular processes and offer novel and as yet under explored therapeutic targets for the treatment of cancer, as well as for hereditary disorders of immune cells, platelets, retinal epithelia, and peripheral neurons.

The regulation of cell proliferation, differentiation and apoptosis is in part dependent on the proper functioning of over 150 human proteins belonging to the Ras superfamily of GTPases. Mutant Ras superfamily members are implicated in oncogenesis and a number of hereditary disorders, yet thus far there has been limited effort focused on small GTPases as therapeutic targets. The Ras superfamily consists of five distinct subfamilies, three of which are the focus of thes experiments. We elected to focus on the Ras protein family functioning in signal transduction cascades, as well as the Rab and Rho protein families, which regulate membrane transport and actin cytoskeletal dynamics for several reasons. First, Ras, Rab and Rho proteins have close functional connections through Ras signaling [1-4]. Second, GST-chimeras of Ras, Rab and Rho family members are readily available and are known to retain biological activity (Detailed in preliminary results). Third, established collaborations with investigators (B. Wilson, Ras; A. Wandinger-Ness, Rab; G. Bokoch, Rho) studying each of these families ensures seamless interfaces between high throughput screening and biological assays to further characterize the phenotypic effects of individual lead compounds identified in the screens. The aims of the experiment include the following:

1) To identify chemical regulators of GTP-binding, which may be competitive or allosteric in nature, by HTS of the MLSCN library of 100,000 compounds.
2) To optimize chemical regulators of GTP-binding that are identified in the initial screen and validated by independent secondary assays.

A fluorescent, flow cytometric GTP-binding assay has already been optimized for Rab7 and its applicability to other GTPases has been established. Multi-milligram quantities of purified recombinant, GST-fusion proteins have been obtained or are otherwise available from commercial sources. Representative members have been screened to establish the suitability of this homogeneous assay for the high-throughput environment. The investigators have applied high throughput multiplex flow cytometry methods and demonstrated the suitability of the assay for screening up to a six-plex of interactions using high throughput flow cytometry.

Purified Ras Superfamily Members and a Fluorescent GTP-Binding Assay

GST and N-terminal GST-fusions of representative Rab, Rho and Ras proteins have been expressed and purified or purchased from commercial vendors. Milligram quantities of GST-Rac1 or GST-Rac2 have been isolated and purified from bacterial preparations and yields of 200 μg to 1 mg of the prenylated proteins obtained from baculovirus (Bokoch lab). Milligram quantities of GST-Rab7 and disease-associated mutant forms have been isolated and purified to homogeneity from bacterial preparations (Wandinger-Ness lab). Milligram quantities of GST-RhoA, GST-Cdc42 wild type (wt) and constitutively active (act) Cdc42, GST-H-Ras act, Rac1 wt and Rac1 act were purchased from Cytoskeleton.

A fluorescent GTP-binding assay capable of being monitored by flow cytometry was developed and optimized using GST-Rab7 protein and Bodipy-FL-GTP (GTP*). The assay was used to evaluate nucleotide exchange to provide proof-of-principle for its utility in flow cytometric measurements and to demonstrate the capacity for detecting fluorescent nucleotide displacement by specific unlabeled molecules. Values are usually expressed as 1000 fluorescence equivalents of fluorescein in free solution (kMESF).

For this purpose, flow cytometry suited, high glutathione density beads (bGSH) were prepared by loading Superdex peptide beads or latex beads with GSH as previously described [26]. In published work, the GST-fusion protein binding characteristics of the beads were assessed using GST conjugated to green fluorescent protein [26]. The density of GSH on latex beads was shown to be adequate to permit binding of the GST fusion proteins that was sufficiently stable to permit simple ligand binding and multiplexed analysis with several fusion proteins on individual bead population distinguished by labeling the beads with different intensities of an "address" in a "suspension array". Proof of principle experiments were conducted on the larger dextran beads prior to using the multiplexed sets of latex beads. A competition experiment between $1.0 \times 10^{-7}$ M of GST-GFP and increasing concentration ($1 \times 10^{-12}$ M–$1 \times 10^{-3}$ M) of GST-Rab7 resulted in $EC_{50}$ $2.75 \times 10^{-7}$ M, thereby confirming that the two GST-fusion proteins have similar binding affinities for bGSH (not shown).

Figure 5:
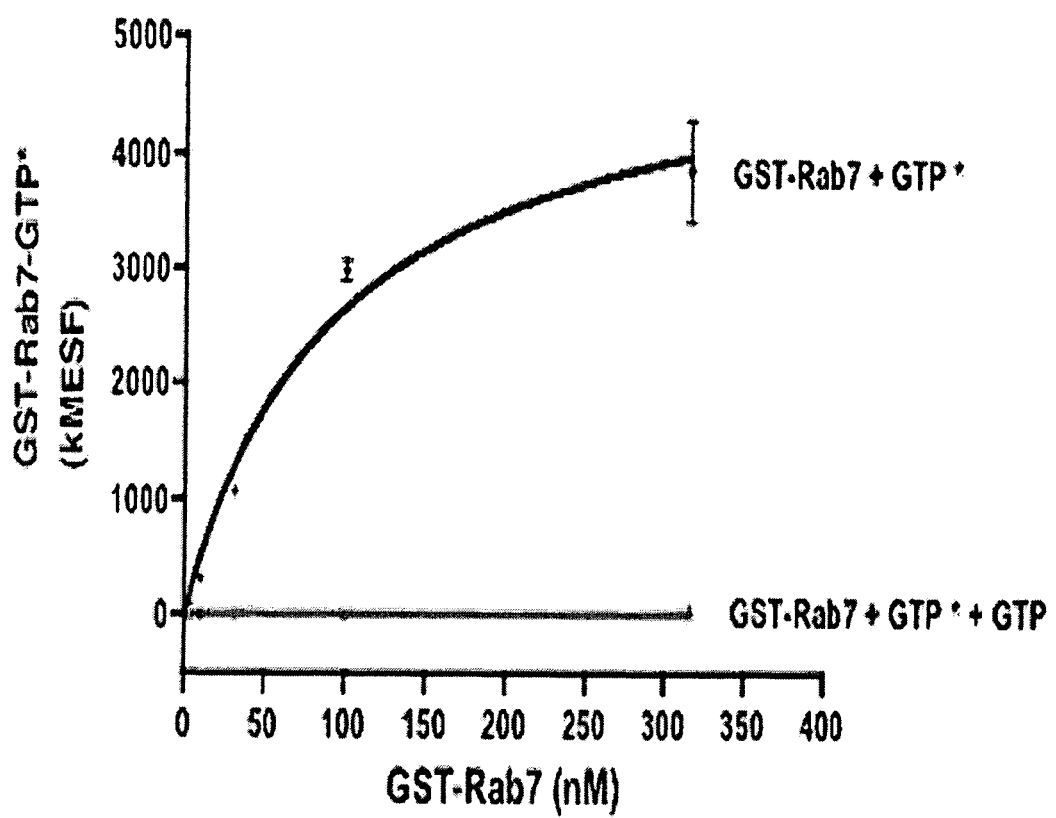
FIG. 5 shows the binding of Bodipy-FL-GTP loaded GST-Rab7 onto bGSH. To directly measure the binding affinity of GST-Rab7 to GSH-beads, increasing concentrations of GST-Rab7 were incubated for 2 h with a constant amount of excess GTP* (1 µM Bodipy-FL-GTP) and GSH-beads. Non-specific binding of GTP* was measured by including 100-fold higher (100 µM) non-fluorescent GTP in the reaction.

The binding of purified GST-Rab7 to bGSH was measured by using increasing concentrations (1.0-316.0 nM) of GST-Rab7 with a fixed amount of bGSH (~10,000 beads/reaction and excess (1.0 □M) GTP*). The specificity of the fluorescent signal to bead-binding of GST-Rab7-GTP* was verified using 100-fold excess (100 μM) unlabeled GTP or incubation of bGSH with GTP* in the absence of GST-Rab7, both of which showed extremely low non-specific fluorescent signal (FIG. 5) (Tessema and Wandinger-Ness, unpublished data).

Figure 6:
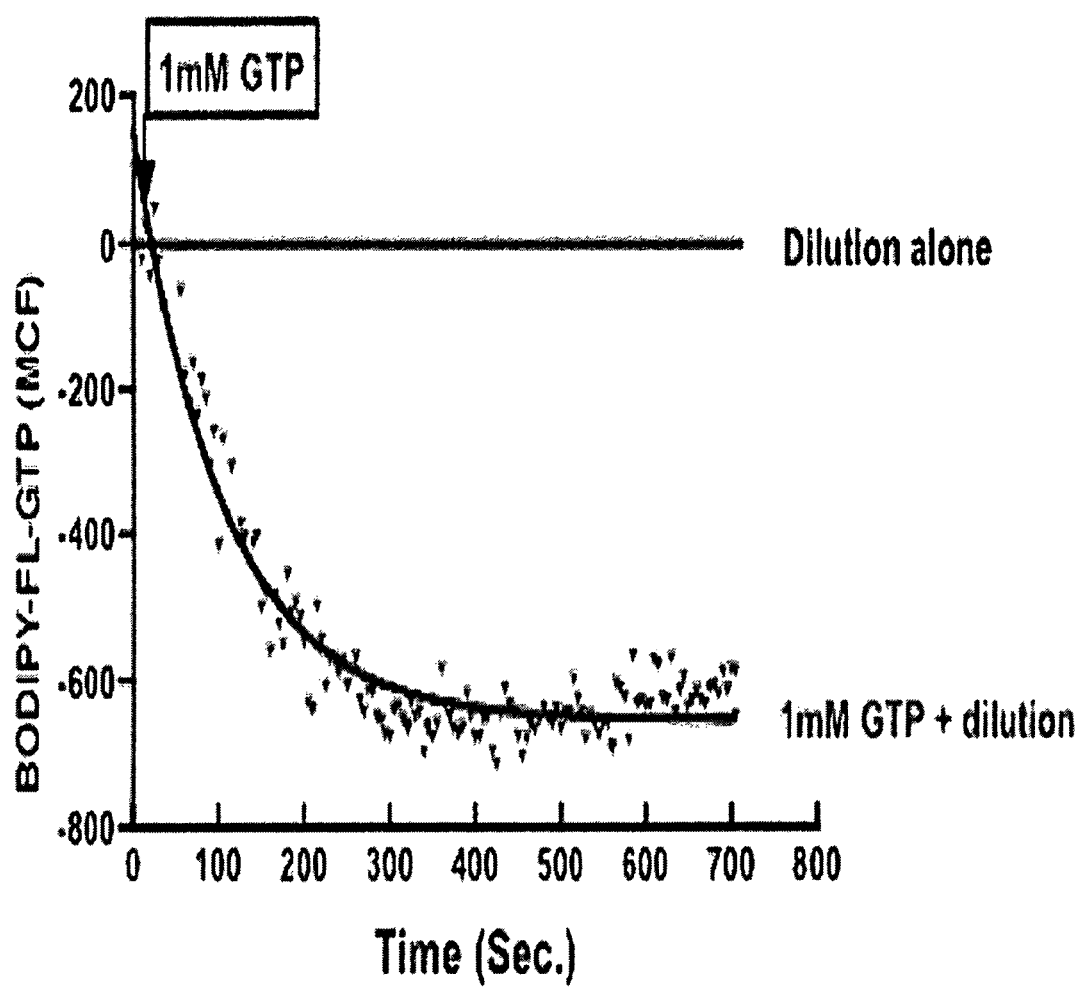
FIG. 6 shows the rates of GTP* dissociation from bead bound GST-Rab7. The rate of dissociation due to addition of 1 mM GTP alone was calculated by subtracting the dissociation due to dilution alone from that of the total dissociation. The rate of dissociation and the $t_{1/2}$ due to 1 mM GTP alone were, therefore, $9.6 \times 10^{-3}$ $s^{-1}$ and 72.7 s, respectively. Y axis shows mean channel fluorescence (MCF), where the voltage and gain on the cytometers is adjusted so that MCF is within 10% of kMESF.

In order to measure the rate of GTP* dissociation from bead-bound Rab7, bGSH were pre-loaded with 100 nM GST-Rab7 and incubated with 1 □M GTP* at 37° C. for 2 h. Dissociation of GTP* from the beads was then measured at 37° C. both for simple dilution with buffer as well as upon addition of 1000-fold higher (1 mM) non-fluorescent GTP (FIG. 6). The calculated half-time was 72.7s. The rate of dissociation in the presence of 1 mM unlabeled GTP alone was $9.6 \times 10^{-3} s^{-1}$.

In order to compare the affinity of bead bound GST-Rab7 to the fluorescent nucleotide analogue (GTP*) with that of non-fluorescent GTP, 100 nM GST-Rab7 loaded bGSH were incubated to equilibrium with 1 µM GTP* and an increasing concentration ($1 \times 10^{-12}$ to $1 \times 10^{-3}$ M) of the competitor (GTP) (FIG. 7A). From the resulting $EC_{50}$ of $8.3 \times 10^{-7}$ M, a $K_i$ of $2.36 \times 10^{-8}$ M was calculated, using the mean $K_d$ of 94 nM from the GTP* binding to GST-Rab7 and the Cheng and Prusoff equation, $K_i = EC_{50}/(1+([ligand]/K_d))$.

A similar competition experiment using bGSH pre-loaded with 10 nM GST-Rab7 and 1 µM GTP* and increasing concentrations ($1 \times 10^{-12}$ to $1 \times 10^{-3}$ M) of GDP resulted in an $EC_{50}$ of $5.6 \times 10^{-7}$ M (FIG. 7B). Taken together these results: 1) indicate that bead bound GST-Rab7 has comparable affinity for the fluorescent GTP analogue (GTP*) and the non-fluorescent nucleotides (GTP and GDP); and 2) the binding is well behaved in the sense that the equilibrium values are accounted for by the on and off rates. The signal to background levels are compatible with homogeneous analysis of the binding of the fluorescent GTP analog. Moreover, the assay is conservative with respect to protein, using <1 pmol of protein per well. This occurs because the GTP binding protein is typically displayed at hundreds of thousands of sites per bead at a total bead volume of 10 µl. This contrast with polarization assays in which larger volumes may be required at concentrations in the vicinity of the $K_d$ of the binding interaction (100 nM).

Rab7 Mutants in Charcot-Marie-Tooth Disease Bind GTP, but Behave as Dominant Negatives.

Figure 8:
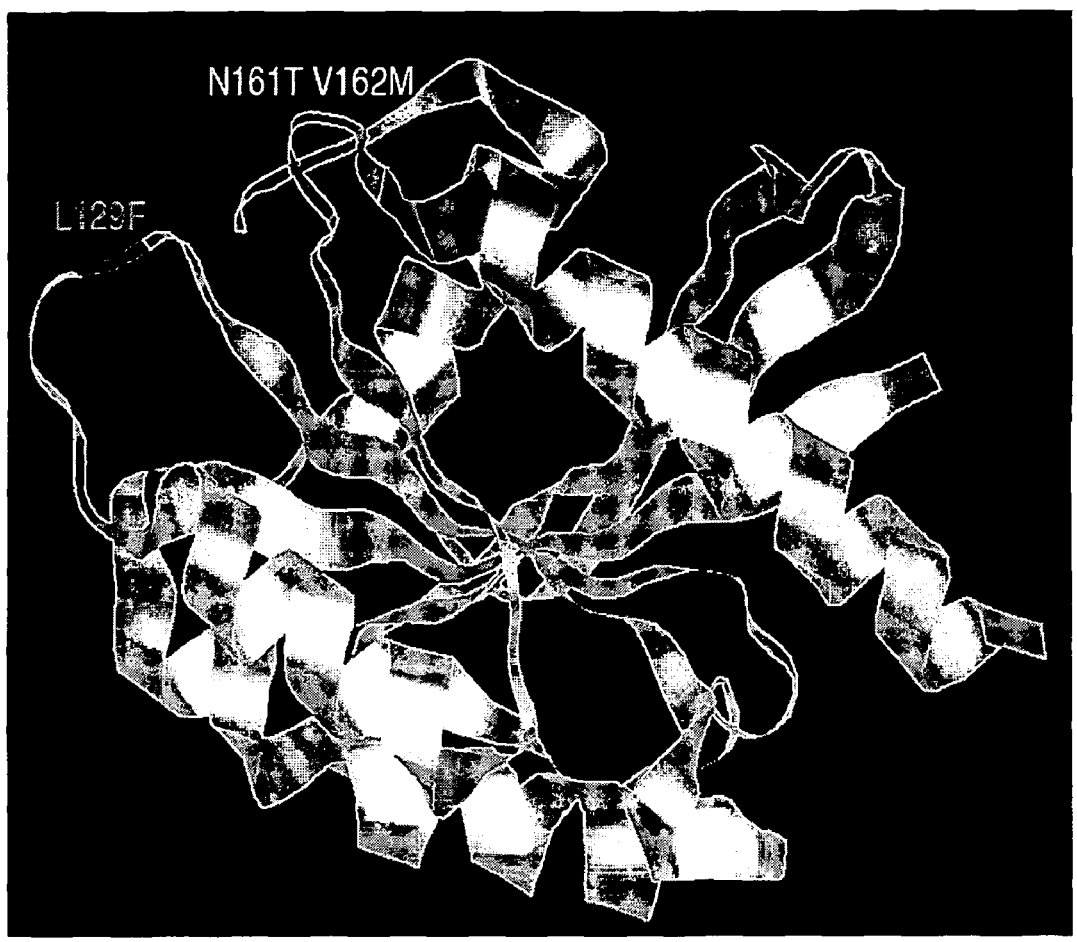
FIG. 8 shows the amino acid substitutions in Rab7 which result in CMT Disease. Rab7 mutants mapped on the known crystal structure of Rab7 reveal them to be at the mouth of the GTP-binding pocket.
Figure 9A:
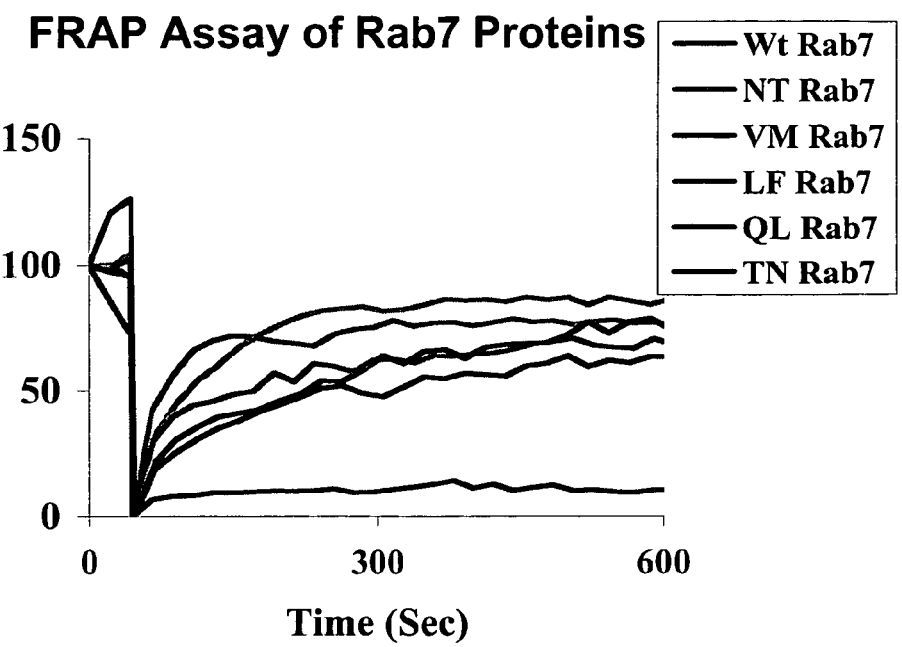
FIG. 9 shows GTP-Binding by CMT mutants of Rab7. (A) Fluorescence recovery after photobleaching (FRAP) was used to compare overall nucleotide and membrane binding properties of the CMT mutants (VM, LF, NT) relative to wild-type (wt) Rab7 and conventional GDP-binding T22N (TN) and GTP-binding Q67L (QL) mutants in vivo. The data suggest that CMT Rab7 mutants retain GTP-binding activity. (B) CMT Rab7 mutant proteins purified from *E. coli* were tested in vitro by flow cytometry. The assay directly demonstrated GTP-binding to the disease-associated Rab7 mutants.
Figure 9B:
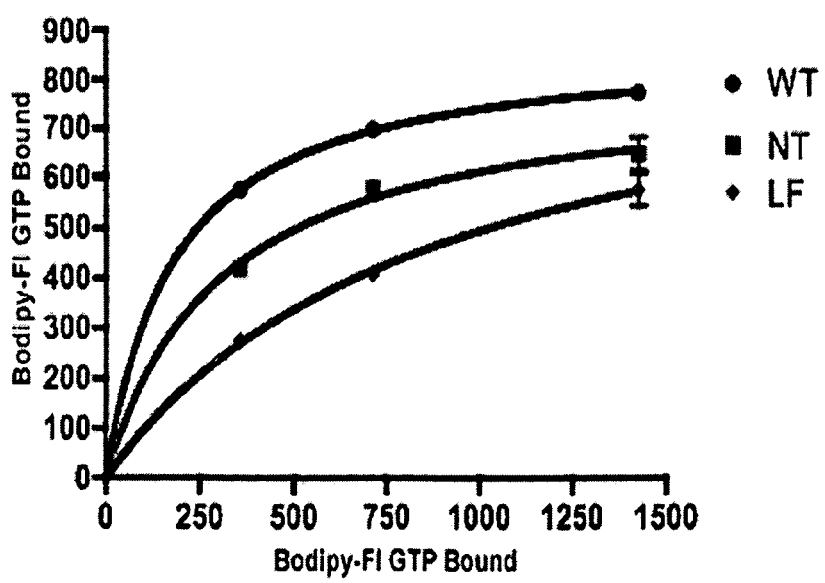

Charcot-Marie-Tooth (CMT) disease results in peripheral neuropathies caused by Schwann or nerve cell dysfunction [27]. Three different point mutations in the Rab7 GTPase (L129F, N161T and V162M) have been found associated with patients with neuropathy in Type 2B CMT disease [14, 15]. We have analyzed the GTP-binding and physiologic activities of these mutants by overexpression in human and rodent cell lines (Mukherjee and Wandinger-Ness, unpublished data). When superimposed on the known 3D structure of Rab7 [28], the mutations map close to, but not within the GTP binding pocket of Rab7 (FIG. 8). Evaluation of GTP and membrane binding using a FRAP assay [29] suggests the mutant Rab7 proteins associate with late endosomes and bind GTP analogous to the wild-type (WT) protein, but are distinct from the GDP-binding T22N (TN) mutant (FIG. 9A). Similar results were obtained using the flow cytometry assay, demonstrating directly that the mutants retain GTP-binding activity (FIG. 9B). Nevertheless, the mutant proteins are differentially altered in their abilities to bind specific downstream effectors and promote growth factor downregulation and neurite outgrowth (not shown). We plan to include the CMT mutants of Rab7 in the high throughput screen as bona fide disease targets and to assess if chemical compounds with different specificities for wild-type and mutant proteins can be identified and used for the inactivation of dominant negative proteins. Biological assays are in hand for secondary screens and GST-chimeras of the Rab7 mutants demonstrate their utility for flow cytometric screening.

Fluorescent GTP-Binding Assay Adapted to Multiplexed, High-Throughput Measurements.

Figures 10A, 10B, 10C, 10D:
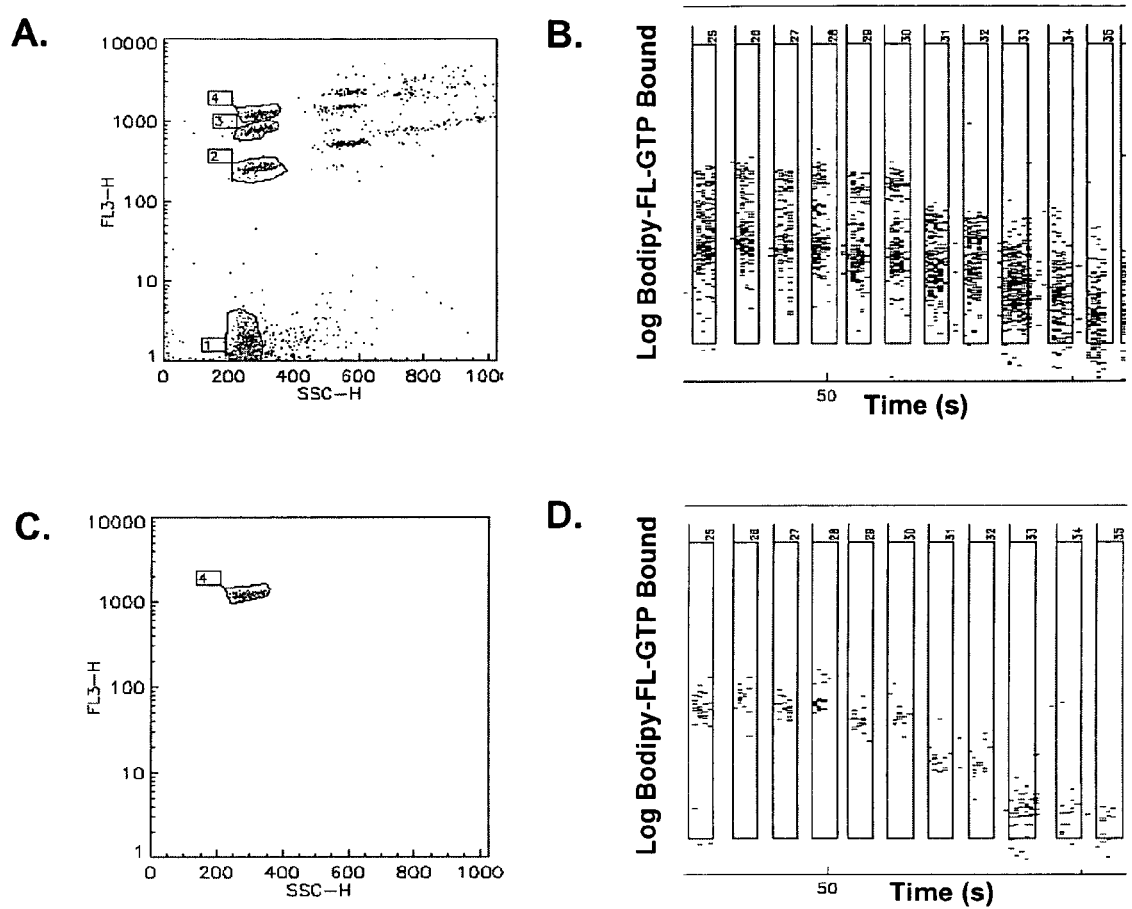
FIG. 10 shows raw multiplexed data and single bead type data.
Figure 11:
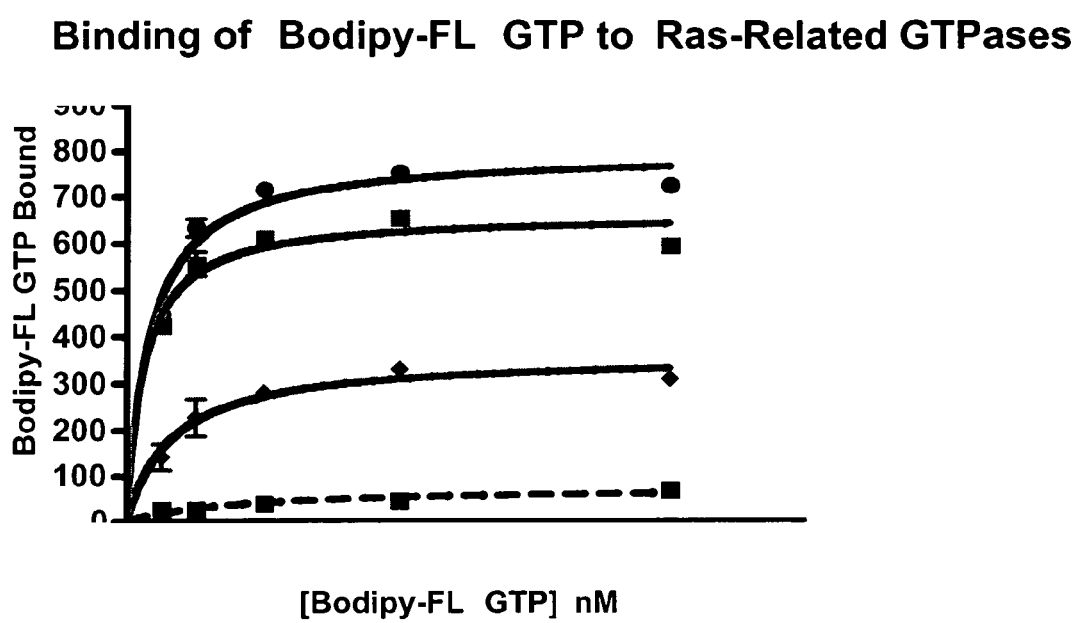
FIG. 11 shows that Ras superfamily members exhibit similar affinities for Bodipy-FL-GTP. Amount of Bodipy-FL-GTP bound to the beads expressed as kMESF. Binding was measured simultaneously in a fourplex using GST only as a control.
Figure 12:
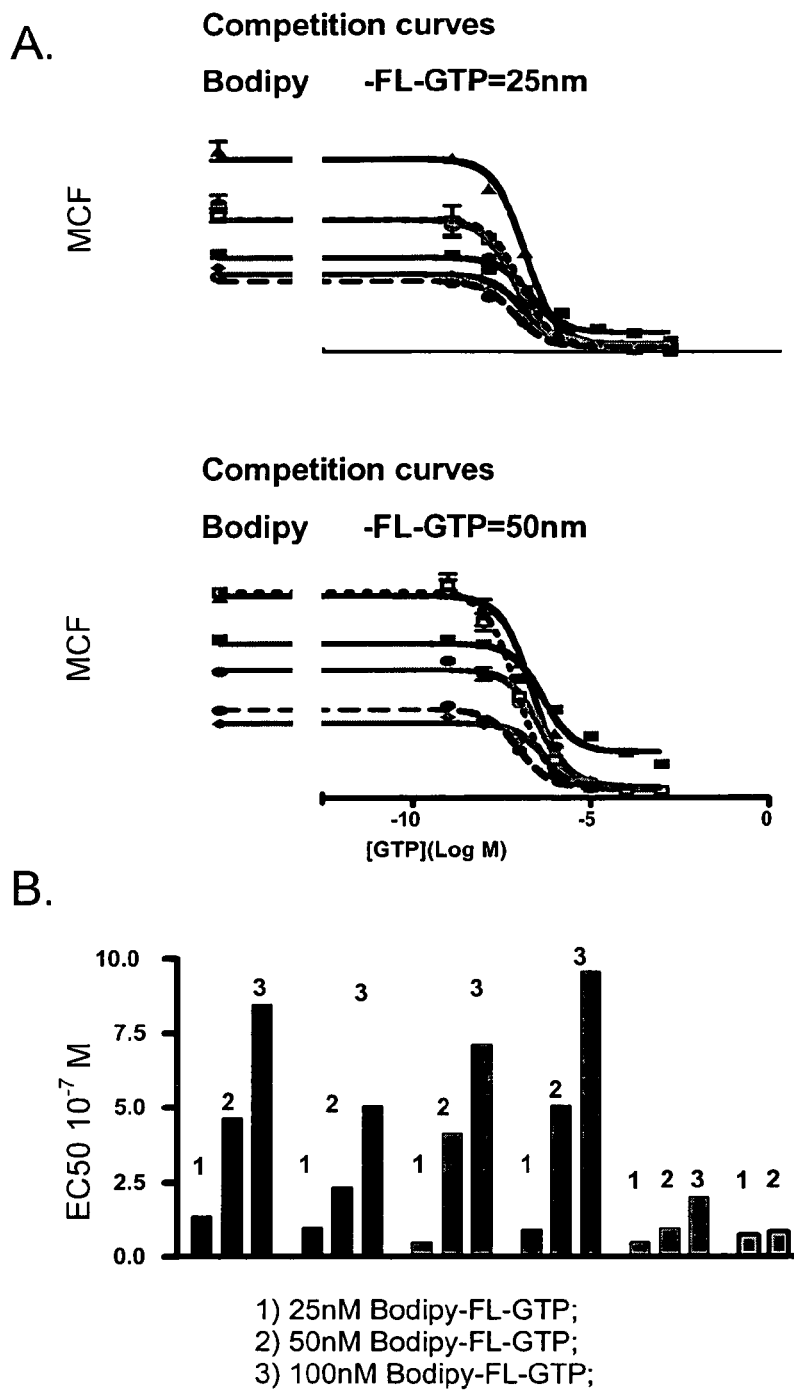
FIG. 12 shows that six Ras superfamily members exhibit $EC_{50}$s for GTP within the Same Order of Magnitude. Competition curves for six Ras superfamily members were generated simultaneously in a sixplex assay. A) Bound Bodipy-Fl-GTP (25 or 50 nM) was displaced using unlabeled GTP. Individual GTPases display differential affinities for Bodipy-FL-GTP vs. unlabeled GTP. B) EC50s calculated from the competition curves confirm that all values are within the same order of magnitude.
Figure 13:
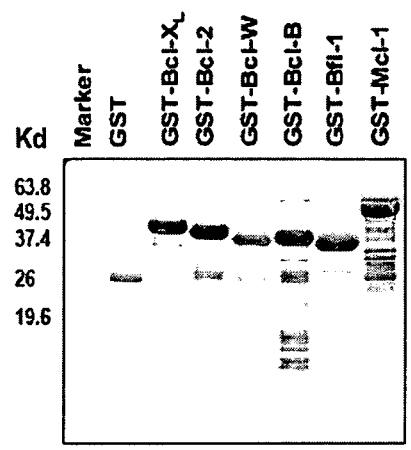
FIG. 13 shows the purification of GST-Bcl-2 proteins. 10 µg of each purified protein was analyzed by SDS-PAGE followed by Counnassie Blue Staining. GST protein was used as a control.

The Bodipy-FL-GTP binding assay established using wild-type GST-Rab7 was adapted for multiplex, high-throughput assays by Sklar and colleagues. FIG. 10 shows raw fourplex data relative to single bead data. The specific binding affinities of various Ras superfamily members for Bodipy-FL-GTP were within a factor of two of each other, and the probe was competed by GTP at $EC_{50}$s within the same order of magnitude (FIGS. 11-12). The results of fourplex and sixplex assays for Bodipy-FL-GTP binding and GTP competition studies demonstrate our ability to implement a multiplex assay in which multiple GTPases may be simultaneously screened against the molecular library of compounds. The observation that individual GTPases, including wt and activated forms, exhibit measurably distinct affinities for Bodipy-Fl-GTP vs. GTP suggests that we will be able to identify compounds with differential affinities for individual GTPases, as well as for the wild-type and activated forms of the same GTPase.

Research Design and Methods

HyperCyt® Assay Description

The UNM team has established and characterized multiplexed, homogeneous (no-wash) HyperCyt® assays for the sensitive detection of compounds that block Bodipy-FL-GTP binding to Ras and Ras-related small G proteins. These assays are helped by the fact that the Bodipy-FL-GTP fluorescence is environmentally sensitive, and the fluorescence of the aqueous fluorophore is about one tenth that of the bound fluorophore (Molecular Probes data). Thus, the unbound fluorophore does not influence the signal as much as environmentally insensitive probes, and higher concentrations of Bodipy-FL-GTP can be used in the no-wash format than have been already used successfully with fluorescein-based fluorescent probes. The $K_d$s of the test set of small G proteins are within a factor of two of one another, and the competitive assay uses a concentration just below the lower $K_d$ to ensure sensitivity to potential competitors in the NIH Roadmap library of compounds. The biology of individual Ras Superfamily proteins to be screened is detailed below.

HyperCyt® Molecular Library Screening Protocol.

The screen has been formatted for 384-well plates (Greiner # 784101) for a total of 15 µl in each well. 384-well microplates are configured with 64 control wells (columns 1 and 2 unblocked, and columns 23 and 24 with 1 mM GTP), leaving 320 wells to which test compounds are added as per the Roadmap compound plates supplied. Compounds from the molecular library and GTP controls are added in 5 µl, Bodipy-FL-GTP is added in 5 µl, and GST-G protein-coated beads are added in 5 µl. The buffer is an intracellular mimic, 30 mM HEPES, pH 7.5, 100 mM KCl, 20 mM NaCl, 0.01% dodecyl maltoside, 0.1% bovine serum albumin, 1% DMSO, and 1 mM EDTA. The bead sets are coated by mixing each "address level of red fluorescence" bead type individually in the presence of ~60 nM GST-small G protein for two hours with 5,000 beads per microliter. The sets are then combined together, centrifuged, and resuspended just before addition to the assay plate. The beads are kept in suspension during the competitive assay using rotation at 22° C. for 2 hours, then the plate is read at room temperature at a cytometer.

Important considerations in assay implementation are as follows:

i) DMSO Tolerance. Test compounds are stored as DMSO stocks. The fluorescent probe and proteins are stored in aqueous buffer. All are diluted in buffer so that the final concentration of DMSO in test plates is between 0.5% and 1%, which are well tolerated by the assay.

ii) Temperature. All reagents tolerate room temperature for 6 hours, longer than the assay.

iii) Microsphere suspension. Microspheres remain in suspension on an end-over-end rotator and during the 20 minutes required for two readings of the plate, if a second reading is deemed desirable.

iv) Microsphere concentration. A starting bead stock of $2\times10^6$ microspheres/ml of each type is diluted 1:3 in the final assay suspension. This results in the analysis of ~1,000 beads of each type from each well when sampling at 40 wells/min (aspirated volume ~2 μl; some losses occur). Higher bead concentrations, up to $2\times10^7$ beads/ml, have been used successfully.

v) Fluorescent probe concentration. To ensure maximal sensitivity, the fluorescent probe is used at just below the $K_d$ of the small G proteins, 50 nM. In blocking (control) wells, GTP is used at 1 mM.

vi) Test compound concentration. Test compounds are typically screened at final concentrations of 7-10 μM, allowing detection of compounds with a $K_i$ as high as 10 μM.

vii) Automated data analysis. Immediately after data acquisition by the flow cytometer, proprietary software (IDLQuery, developed by Bruce Edwards and available at the NM MLSCN) is used to analyze the data file. The program automatically detects the time-resolved data clusters of events (wells) of beads with bound fluorescent probe, ensures that there are 384, and analyzes each to determine the mean channel fluorescence of bound green peptide for each "address level of red fluorescence" bead type. These reduced data are automatically exported to a Microsoft Excel spreadsheet template that instantly calculates the assay quality control Z' factor and fluorescent probe binding inhibition percent for each small G protein in each well. Thus, comprehensive assay results are available within 10 minutes after assay plate sampling is completed. This provides ample opportunity to detect and correct any technical problems that may occur. Procedures have been implemented that enable rapid detection of errors such as an empty well or difficulties in resolving data clusters from adjoining wells (both relatively rare occurrences). Because each sample consists of 2 μl from a 15 μl volume in each well, we are able to sample and analyze each plate twice and average the results in the Excel spreadsheet.

Confirmatory HyperCyt® Screen.

After the primary screen, compounds that display activity will be cherry picked and retested. This will identify false positives. Compounds that continue to display activity will be assessed for binding affinity by carrying out dose-response assays between 1 nM and 100 μM. In the multiplexed format, the confirmatory screen will also provide information regarding specificity and selectivity. Secondary screens will encompass in vitro and cell-based assays as detailed in the following sections.

Secondary Analysis of Ras Family Members

Biology: H-Ras and K-Ras are well-known for their roles in growth factor induced signaling [26]. When mutant, Ras oncoproteins play a central role in tumor growth and progression [26]. Recruitment of Ras proteins to the plasma membrane via the Raf kinase is of critical importance in the activation of mitogen activated protein kinase (MAPK) signaling. Membrane recruitment of Ras proteins depends on both GTP-binding and proper prenylation. Consequently, farnesylation inhibitors are the most widely used agents to interfere with Ras in tumor cells [26]. The problem with farnesyl transferase inhibitors is two-fold. First, they lack specificity and impact both wild-type and mutant Ras protein, along with other proteins requiring farnesylation for their activity or membrane targeting. Second, K-Ras and N-Ras can serve as in vitro substrates for geranylgeranyl transferase-1 and therefore, mutant forms of these Ras isoforms can escape inhibition [30]. Thus, the proposed screens are expected to identify new classes of molecules with the potential to inactivate specific Ras proteins individually and possibly target mutant Ras proteins selectively.

Ras Activity Measured In Vitro: Ras activation in response to growth factor receptor signaling (will use EGF/EGFR) results in the activation of MAPK cascades. Various cell lines derived from breast and endometrial cancers or CHO cells transfected with wild-type or hyperactivated H-Ras and K-Ras (available in Wilson lab from J. Buss, Univ. Iowa) are treated with lead compounds identified in the primary screen prior to stimulation. Cell lysates are prepared and evaluated directly for active Ras or by measuring downstream effector activation status: e.g., active Ras are scored by Raf/effector pulldown [32, 33]; ERK activation will be measured by western blot analysis of phosphorylation status [34, 35]; and phosphatidylinositol (PI) 3-kinase activation will be monitored by assaying $PIP_3$ levels [36].

Ras Activity Measured in Vivo: Established flow cytometric assays are used to monitor changes in proliferation or apoptosis in response to incubation of CHO cell lines transfected with wild-type or mutant H-Ras and K-Ras +/−lead compounds identified in the primary screen. Propidium iodide staining is routinely used to quantify increases in cells in S phase (proliferating), while annexin binding is used to quantify increases in cells undergoing apoptosis [37].

Secondary Analysis of Rab Family Members: Rab5, Rab7, Rab7 CMT mutants, Rab8, Rab9, Rab11 and Rab26

Biology: The >60 Rab GTPases are well-known regulators of exo- and endocytic membrane trafficking. Individual family members are associated with specific intracellular membranes where they serve to spatially and temporally orchestrate macromolecular assemblies that control protein sorting, vesicle budding, cytoskeletal translocation and vesicle fusion [52, 53]. On the endocytic pathway, Rab5 controls the initial internalization events and delivery to early endosomes, Rab7 and Rab26 control transport to late endosomes and Rab7 interfaces with the autophagic pathway. Rab9 controls recycling from endosomes to the Golgi, and Rab11 controls plasma membrane recycling. Rab8 functions in exocytosis from the Golgi. Together these Rab GTPases represent the best-studied members. Thus, a cohort of effector and regulatory proteins are known and cellular and biochemical assays for measuring their activities are in hand. The Wandinger-Ness lab has the requisite GST-fusions for Rab5, Rab7, Rab8, Rab9, Rab11, Rab26 wild-type and mutant proteins in hand for incorporation into high throughput, multiplex assays. The CMT Rab7 mutants are directly disease relevant and have already been tested in the flow cytometry based assay (FIG. 9B).

Use of Rab (GTP-Binding) Inhibitors or Activators:

Membrane Trafficking Assays: Compounds identified to interact with specific Rab proteins are initially be screened for inhibitory or activating effects on specific membrane transport steps. Such compounds are expected to have utility both for dissecting the molecular details of Rab GTPase function, as well as for therapeutics as detailed below.

Effector Protein Interactions: An effector of Rab8 called optineurin, when mutant, has been shown to cause open angle glaucoma in humans [71, 72]. Therefore, activators or inhibitors of Rab8 would be tested for effects on protein complexes, particularly with optineurin. Such compounds would be expected to have utility in the vision field. The Wandinger- Ness lab has identified two Rab7 effectors XAPC7, an alpha proteasome subunit [61, 73] and the PI 3-kinase hVPS34 [60, 74] and has reagents for monitoring a third effector RILP. It is of interest to study the effect of inhibitors and activators identified in the screen for differential effects on known Rab effector protein interactions that may be useful for altering host pathogen interactions, growth factor degradation and signaling or autophagic pathways.

Differential Effects on Mutant and Wild-Type Protein Activities: As detailed under preliminary results, the CMT mutants of Rab7 have been found to differentially alter effector protein interactions, growth factor receptor downregulation and signaling. Therefore, it is of significant interest to test compounds that are identified as activators or inhibitors of Rab7 for differential effects on wild-type and mutant proteins. Such compounds would be expected to have utility as possible therapeutics by allowing inactivation of dominant negative mutant forms, yet still permitting any wild-type protein that may be present to function. Point mutations in Rab27 cause Griscelli syndrome, an autoimmune and pigmentation disorder. Interestingly, mutant forms of Rab27 also exhibit GTP binding but are dominant negatives [17]. Therefore, if compounds are identified for Rab7 with differential activity toward the wild-type and mutant proteins, it would provide proof-of-principle that such compounds could be identified for other disease relevant Rab family members.

Summary. The examples identify new compounds with the potential of selectively inhibiting or activating members of the Ras superfamily of GTPases. The primary screen is performed on representative members of the Ras, Rho and Rab subfamilies for which secondary functional screens in cell and in vitro based systems are readily available. The identification of compounds that selectively inhibit individual Ras superfamily members is expected to have broad utility both for further cell and molecular analyses of the GTPases, as well as for possible application in cancer, neuropathy, glaucoma, immunodeficiency and other human disease treatments.

Example of Protein-Protein Interaction Screen: Small GTPases

Ras and Ras-superfamily members are subject to regulation through the interaction with multiple binding partners and like kinases serve as protein scaffolds to effect temporal and spatial regulation of cellular processes. Therefore, it is of significant interest to both identify previously unknown binding partners and to identify how the interactions of known binding partners may be modulated.

The present invention may be used to screen libraries of proteins and regulatory domains thereof to identify new binding partners. For example, small GTPases have specific protein cofactors that regulate their nucleotide binding, nucleotide exchange and hydrolysis. To date these protein cofactors have been identified and characterized for only a small number of the total Ras superfamily of GTPases. The present invention may be applied by immobilizing the GTPase of interest on beads and screening for fluorescently conjugated binding partners in available protein libraries of guanine nucleotide exchange factors, GTPase activating proteins, etc. This application of the invention is not restricted to small GTPases and is broadly applicable for identifying new protein-protein interactions using a known GST-fusion protein and screening an expression library as defined above for an interacting protein or regulatory domain.

The present invention may also be used to screen for small molecule or macromoleular regulators, agonists or antagonists of known protein-protein or protein regulatory domain interactions. For example, small GTPases interact with specific protein effectors in their activated state. Interaction with the effectors is critical to downstream function and cellular responses. Thus, it is possible to enhance the response through an agonist or regulator or to diminish the response through an antagonist or regulator. Using the small GTPases as examples, the present application may be used to study the binding or displacement of protein effectors by small molecules or macromolecules. For example, Rab7 has multiple effectors including RILP, XAPC7, p150, Rabring7, and ORP1L among others which have yet to be identified. The invention allows the study of the binding characteristics of Rab7 with each effector (in fluorescently labeled form) or domain thereof. Thus, displacement or increased binding in the presence of a macromolecule or small molecule may be directly measured as a change in the binding of the fluorescently tagged effector or domain thereof. This application of the invention is not restricted to small GTPases and is broadly applicable for identifying hierarchies of regulatory protein or domain interactions using a known GST-fusion protein or regulatory domain and screening for alterations in molecular interactions between the fusion protein and a known protein binding partner when in the presence of another macromolecule or a small molecule. Note: as laid out in the introduction the fusion protein may be an enzyme, a nucleic acid binding protein or a protein scaffold. The binding partner may be a protein, peptide or other macromolecule (DNA, RNA) that is fluorescently tagged. Further details of such an application of the invention are exemplified by the following application related to Bcl2 proteins.

Example Identifying Agonists/Antagonists/Regulators that Alter Molecular Interactions—Bcl2 Proteins Apoptosis is governed in part by Bcl-2 family proteins. The human genome contains six genes that encode anti-apoptotic Bcl-2 family members. Each of these proteins can be bound to endogenous proteins that contain a conserved peptidyl domain called the Bcl-2 homology region 3 (BH3). Pro-apoptotic family members include both multidomain proteins, including Bak, and "BH3-only" proteins, including Bim. As proof of concept, pro-apoptotic BH3 peptides that dock at this site in Bcl-2 and Bcl-XL also increased apoptosis of leukemia and lymphoma cells in culture and in SCID mice (Holinger et al., 1999; Wang et al., 2000; and Walensky et al., 2004). The binding of fluorochrome-conjugated BH3 peptides to Bcl-2 family proteins thus provides the basis for construction of fluorescence assays, suitable for high throughput screening (HTS). Two fluorescent peptides, F-Bim and F-Bak that bind to six and four members of the Bcl-2 family, respectively have been developed and procedures have been devised for producing multi-milligram quantities of purified recombinant proteins and devised a generic fluorescence polarization assay (FPA), using F-Bim (Zhai et al., 2006). A preliminary screen has been performed of ~10, 000 compounds with Bfl-1 and F-Bim, demonstrating the suitability of this homogeneous assay for the high-throughput environment.

The above approaches have been applied to a multiplex analysis by HyperCyt high throughput flow cytometry. The results from assays performed one at a time are shown in the table Bcl-2, below. In addition, we have shown that all six members of the family can be screened simultaneously. Potential advantages of such an approach include single step analysis of specificity and selectivity, small reaction volumes and the discrimination of free and bound assemblies that is conservative with respect to reagent usage as compared to fluorescence polarization assays. The comparison of such an important assay across different platforms is likely to have significant impact on the Molecular Library Screening Center Network.

TABLE Bcl-2

|        | F-Bim, nM | F-Bak, nM |
|--------|-----------|-----------|
| Bcl-XL | 60        | 20        |
| Bcl-2  | 30        | 80        |
| Bcl-B  | 20        | 50        |
| Bcl-W  | <10       | <10       |
| Bfl-1  | 30        | No        |
| Mcl-1  | 20        | No        |

Apoptosis is governed in part by Bcl-2-family proteins. The human genome contains six genes that encode anti-apoptotic members of the Bcl-2 family, which have both apoptotic and anti-apoptotic interactions with other family members (Reed et al., 2004). We propose to identify and optimize chemical regulators of the family of interacting components. To this end, procedures have been devised for producing multi-milligram quantities of purified recombinant proteins of all of the family members, and has devised a fluorescence polarization assay (FPA), using synthetic peptides conjugated with FITC, F-Bim and F-Bak (Zhai et al., 2006). A preliminary screen has been performed for ~10,000 compounds, demonstrating the suitability of this homogeneous assay for the high-throughput environment. Methods for have been developed for high throughput multiplex flow cytometry that have now been applied to the Bcl-2 family members. In these examples, we screen a six-plex of interactions with F-Bim and a four-plex with F-Bak using high through flow cytometry.

The Bcl-2 Family

Apoptosis is governed in part by Bcl-2-family proteins. The human genome contains six genes that encode members of the Bcl-2 family which have anti-apoptotic activity (Reed et al., 2004). FPAs for each of anti-apoptotic members of the mammalian Bcl-2 family, Bcl-2, Bcl-XL, Bfl-1, Mcl-1, Bcl-W, and Bcl-B, are based on F-Bim. F-Bak interacts with four members of the family.

X01 for Bfl-1 (also known as A1 in mice), a NF-KB-inducible member of the Bcl-2 family are to be analyzed. Bfl-1 is highly expressed in lymphoid tissues. The endogenous functions of Bfl-1 are largely unknown, due to difficulties with accomplishing targeted gene ablation in mouse models. Unlike the other anti-apoptotic members of the Bcl-2 family that have all been successfully ablated in mice, the mouse ortholog of Bfl-1 consists of a cluster of four replicated genes (i.e., four copies of the gene, termed A1a, A1b, A1c, and A1d).

The approach is to identify and optimize chemical inhibitors of Bfl-1. To this end, procedures have been devised for producing multi-milligram quantities of purified recombinant Bfl-1 protein and devised a fluorescence polarization assay (FPA), using a Bfl-1-binding synthetic peptide conjugated with FITC. A preliminary screen has been performed of ~10,000 compounds, demonstrating the suitability of this homogeneous assay for the high-throughput environment.

To identify compounds selective for Bfl-1, FPAs for each of the other five anti-apoptotic members of the mammalian Bcl-2 family, Bcl-2, Bcl-XL, Mcl-1, Bcl-W, and Bcl-B were produced. Compounds that inhibit Bfl-1 but not other members of the Bcl-2-family are identified, providing chemical probes for studying the biological role of Bfl-1. Of note, there has been a systemic analysis of all chemical inhibitors of Bcl-2 thus far described in the literature (Reed and Pellecchia, 2005), using FPAs for each of the six anti-apoptotic members of the Bcl-2 family (Zhai et al., 2006). None of the synthetic compounds or natural products previously reported selectively binds Bfl-1 with a biologically relevant affinity, based on competition assays using FITC-BH3 peptides. Several compounds however bind the various members of the Bcl-2 family with affinities in the 0.1-3 uM range, and some bind selectively to certain subsets of the Bcl-2 family (Oltersdorf et al., 2005). Thus, the pocket on Bfl-1 that binds BH3 peptides is presumably sufficiently different from other Bcl-2 family members that it should be possible to obtain selective inhibitors, either directly from screens of diverse libraries or secondarily through chemical analoging of hits that interact with Bfl-1. We note that while siRNA or antisense could be used to ablate Bfl-1 expression in human cells to test the function of this protein, compounds allow us to ask more subtle questions about the role of Bfl-1 as a "sink" for endogenous BH3-containing proteins and the specific role of the BH3-binding pocket of Bfl-1. In this regard, we have determined that Bfl-1 binds other proteins besides BH3-containing pro-apoptotic molecules (such as TR3/nur77) and these other (non-BH3) proteins do not compete for the BH3-binding pocket. Thus, to knock-out expression of the entire Bfl-1 protein would not allow us to ask questions about the specific function of Bfl-1 as an endogenous neutralizer of BH3-containing pro-apoptotic proteins.

The present method takes a next logical step in using high throughput, multiplexed flow cytometry, for identifying small molecules that have potential not merely as probes for the activity of one specific member of the Bcl-2 family, but as leads for drug discovery for the entire family.

Assay Components, Fluorescence Polarization Assays and Competitive Assays.

Purification of GST-Bcl-2 family proteins. Expression plasmids for all six human anti-apoptotic Bcl-2 family proteins have been prepared for protein production in bacteria. In each case, the C-terminal transmembrane (TM) domain was excluded from the construct to ensure protein solubility. The protein yield for the GST-Bcl-2 family proteins is approximately 5 mg per liter cells. After single-step glutathione-Sepharose affinity chromatography, the purity is over 95%, as determined by Coumassie Blue staining of material analyzed by SDS-PAGE.

Figure 14:
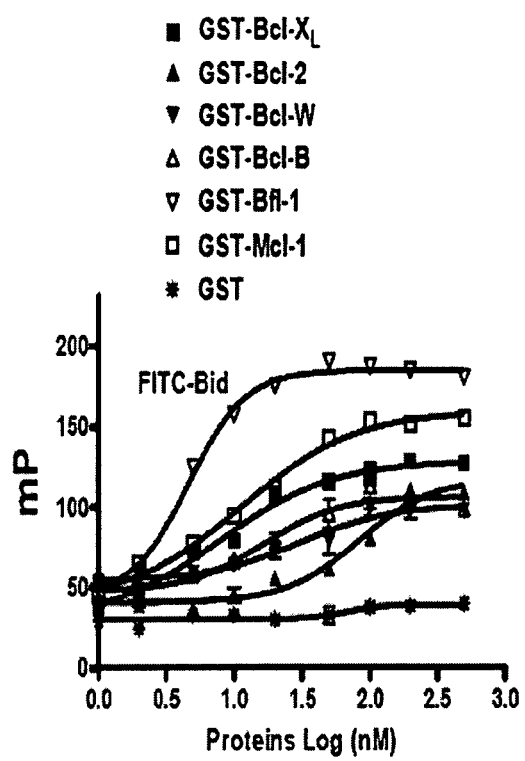
FIG. 14 shows an FPA analsysi of Bcl-2-family proteins using FITC-Bid BH3 peptide. Various concentrations of GST or GST-Bcl-2-family fusion proteins were incubated with 5 nM FITC-conjugated-Bid-BH3 peptide in PBS [pH 7.4]. Fluorescence polarization (in milli-polars) was measured after 10 minutes.

FPA binding curves for Bcl-2-family proteins. Various concentrations of GST-fusion proteins containing ATM versions of Bcl-2, Bcl-XL, Bfl-1, Mcl-1, Bcl-W, and Bcl-B were incubated with a fixed concentration of FITC-conjugated BH3 peptide from Bid, and fluorescence polarization was measured (milli-Polars). All Bcl-2 family proteins caused fluorescence polarization, but to variable extents, consistent with differences in their individual affinities for this particular BH3 peptide. Note that Bfl-1 binds best among the anti-apoptotic Bcl-2 family members to Bid BH3 peptide. Note that GST control protein does not cause fluorescence polarization. See FIG. 14.

Figure 15:
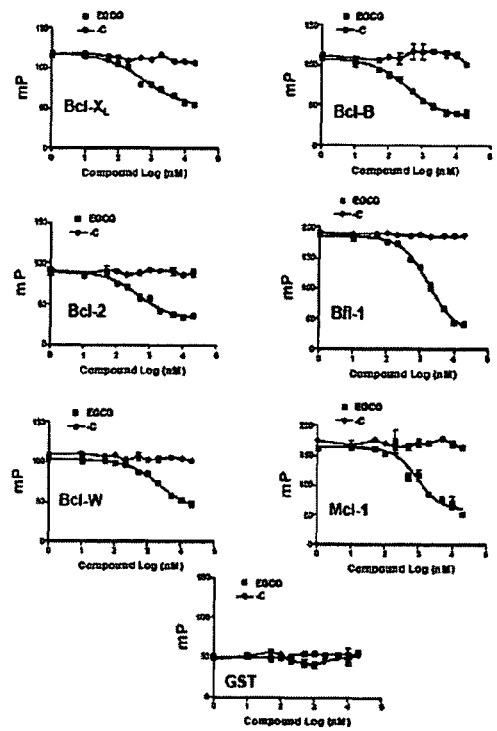
FIG. 15 shows the competition assay analysis of the green tea compound EGCG. 100 nM of GST-Bcl-2 fusion proteins were incubated with various concentrations of EGCG or control compound ECG ("C") for 2 min in PBS buffer in 50 µL. Then, 5 nM FITC-conjugated-Bid BH3 peptide was added, bringing final volume to 100 µL and final DMSO concentration to 1%. Fluorescence polarization was measured after 20 minutes.

C1.3 FPA competition assay for Bcl-2-binding compounds. The green tea compound epigallecatechin (EGCG) has been reported to bind Bcl-2 and Bcl-XL (Leone et al., 2003). The ability of EGCG to compete with fluorochrome-labeled BH3 peptides was confirmed by FPA. Note that ECGC binds to all six anti-apoptotic members of the Bcl-2-family, to variable extents. This compound therefore can serve as a positive control when performing high throughput screens of any compound library, including the NIH library. See FIG. 15.

Figures 16A, 16B, 16C:
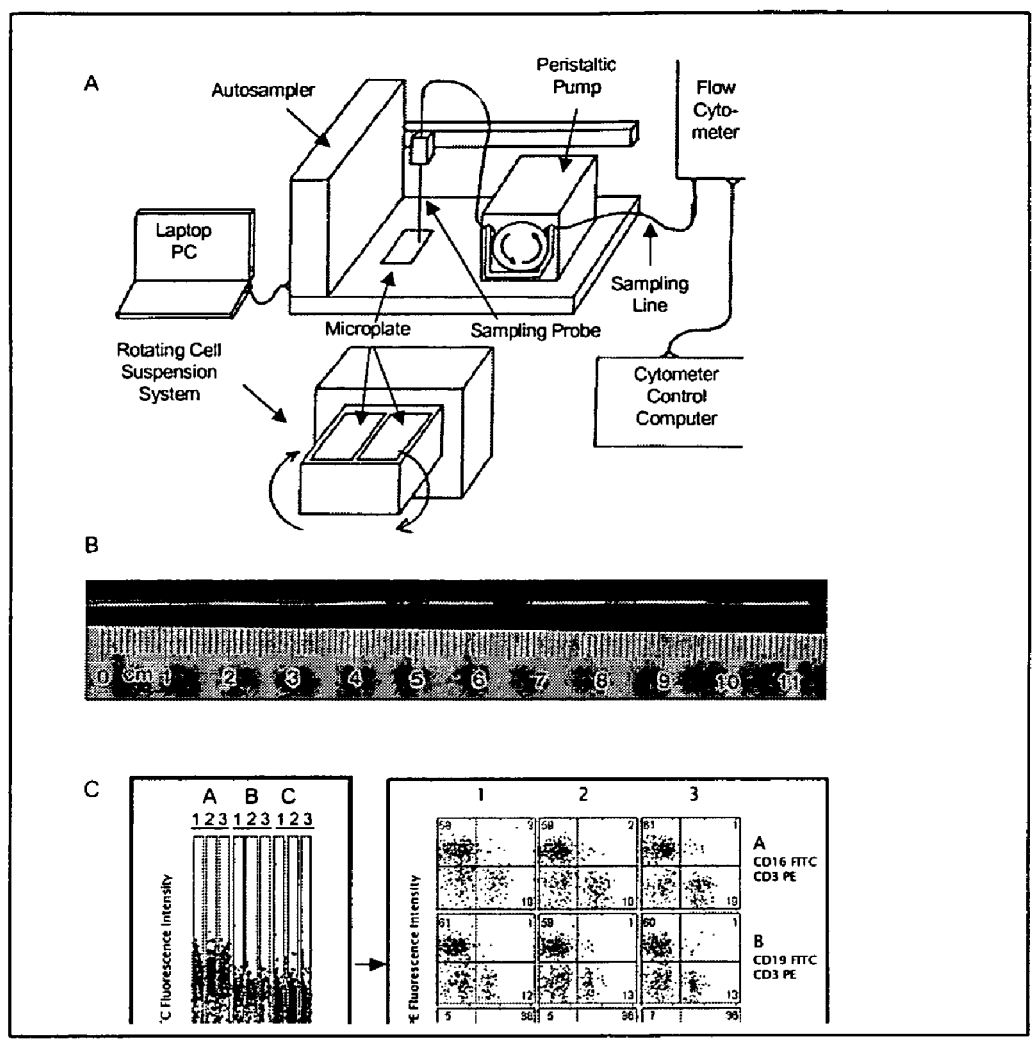
FIG. 16 shows a typical HyperCyt® flow cytometer. A. Shows Endpoint assay configuration. B. Shows Air bubble-separated samples in the sampling line for serial delivery to flow cytometer

High Throughput Flow Cytometry, for Use in Individual Assays or Throughput Multiplexing is Used HyperCyt®. The HyperCyt® system (Kuckuck et al., 2001, Ramirez et al., 2003) interfaces a flow cytometer and autosampler (FIG. 16A). As the sampling probe of the autosampler moves from one well to the next of a multi-well microplate, a peristaltic pump sequentially aspirates sample particle suspensions from each well. Between wells, the continuously running pump draws a bubble of air into the sample line. This results in the generation of a tandem series of bubble-separated samples for delivery to the flow cytometer (FIG. 16B). Sample and bubble volumes are determined by the time that the autosampler probe is in a microplate well or above a well intaking air.

Cell-based high throughput endpoint assays for ligand binding, surface antigen expression, and immunophenotyping (Ramirez et al., 2003) are used. Accurate quantitative measurements have been demonstrated in endpoint assays at rates to 40 samples/min over a 4-decade range of fluorescence intensity using input cell concentrations of 1-20 million/ml and source well volumes of 5-15 µl. Typical sample volumes of 1-2 µl allow scarce quantities of test cells or reagents to go a long way.

Commercial alternatives are as much as 20 times slower due both to differences in the way samples are delivered and data are acquired. In HyperCyt®, the air bubble-separated samples are delivered in a continuous stream to the flow cytometer. Likewise, the data are collected in a continuous stream, the accumulated data from all wells of a microplate representing a single data file. The time-resolved data, with periodic gaps corresponding to the passage of the sample-separating air bubbles (FIG. 16B), are analyzed by proprietary software developed by Bruce Edwards of the NM MLSC, FCSQuery. Now IDLQuery, a more advanced analysis package, takes advantage of powerful array processing algorithms, graphics support and multi-platform compatibility features of the IDL programming language [RSI Inc.].

Assay Construction

Figure 17:
FIG. 17 shows a typical microsphere assay assembly schematic which is used in the present invention.

Assays are constructed as illustrated generically in FIG. 17. Each assay consists of a glutathione labeled bead, a GST fusion protein, and a fluorescent peptide. Six proteins (Bcl-XL, Bcl-2, Bcl-B, Bcl-W, Bfl-1, Mfl-1) are available from the Burnham team as GST fusions. The two peptide probes, F-Bim and F-Bak, are conjugated to fluorescein. The multiplex is derived by using beads that have been colored with varying intensities of a red color, so that each assay is built on a separate bead set. We have shown previously that while individual GSH-GST interactions are weak, GST dimerization allows us to create assemblies that are stable enough to make multiplexing possible (Tessema et al., 2006).

TABLE Bcl

|  | F-Bim, nM | F-Bak, nM |
| --- | --- | --- |
| Bcl-XL | 60 | 20 |
| Bcl-2 | 30 | 80 |
| Bcl-B | 20 | 50 |
| Bcl-W | <10 | <10 |
| Bfl-1 | 30 | no |
| Mcl-1 | 20 | no |

Figure 18A:
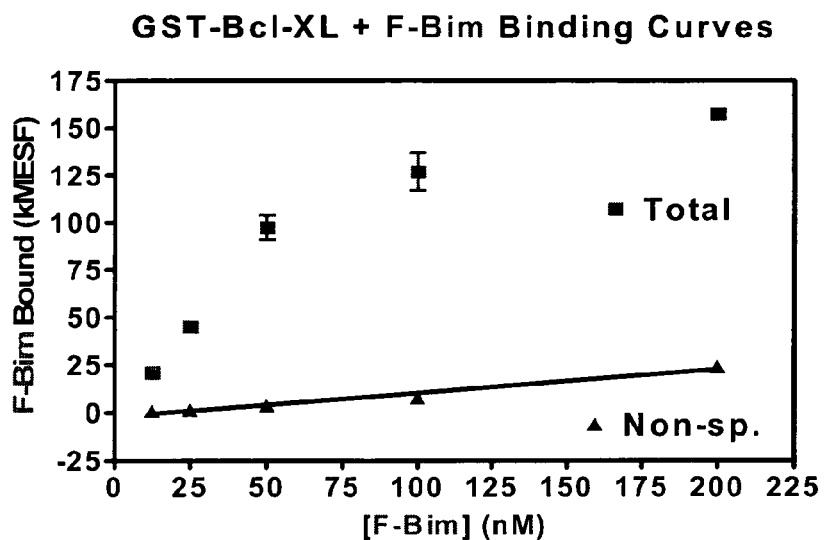
FIG. 18 shows the binding curves for F-Bim binding to Bcl-XL. The data show that about 180,000 GST-Bcl-XL molecules were bound to the beads, and that F-Bim bound with a $K_d$ of about 60 nM. Data are collated in the Table.
Figure 18:
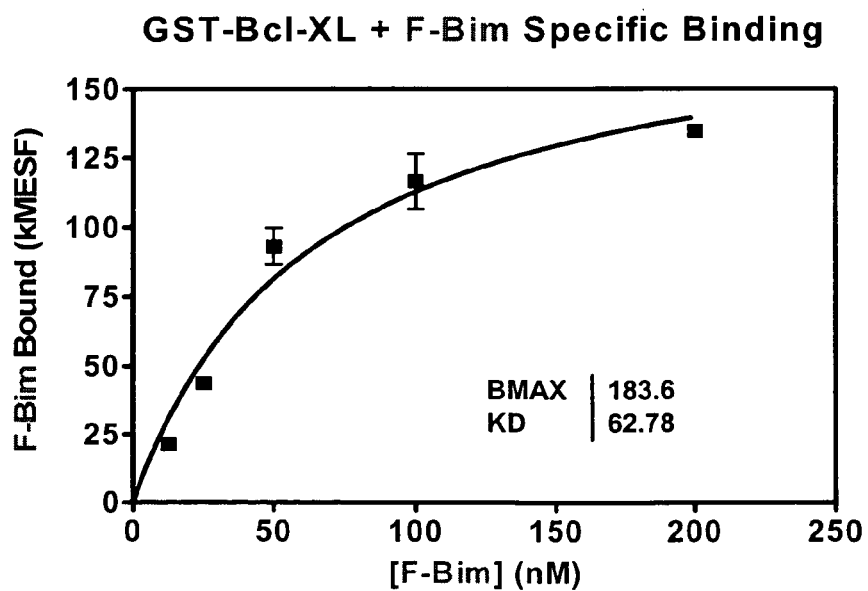

A typical manual flow cytometric binding assay is shown in FIG. 18 for F-Bim binding to Bcl-XL on uncolored beads. The total, non-specific, and specific binding components are defined as they would normally be defined in terms of the total signal, the signal in the presence of excess inhibitory peptide, and the difference between the two. $B_{max}$ is an estimate of the number of sites per bead and $K_d$ is the affinity. We have previously defined methods using standardized bead sets that allow the fluorescence to be expressed in fluorescein equivalents. The table summarizes the results for the Bcl-2 family.

Figure 19:
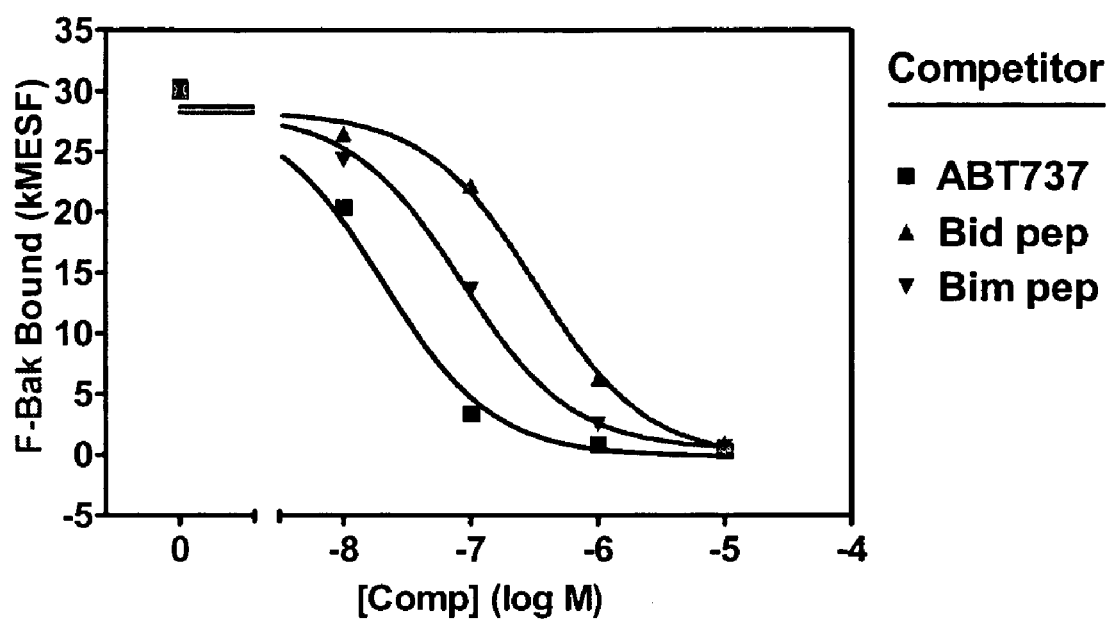
FIG. 19 shows the competition between F-Bak and three small molecules, for binding to GST-Bcl-2. Using the $K_d$ of 80 nM shown in the Table, and a concentration of 20 nM F-Bak, $K_i$ values were calculated using the Cheng-Prusoff relationship: ABT737 binds better than the Bim peptide, which binds better than the Bid peptide.
Figure 20:
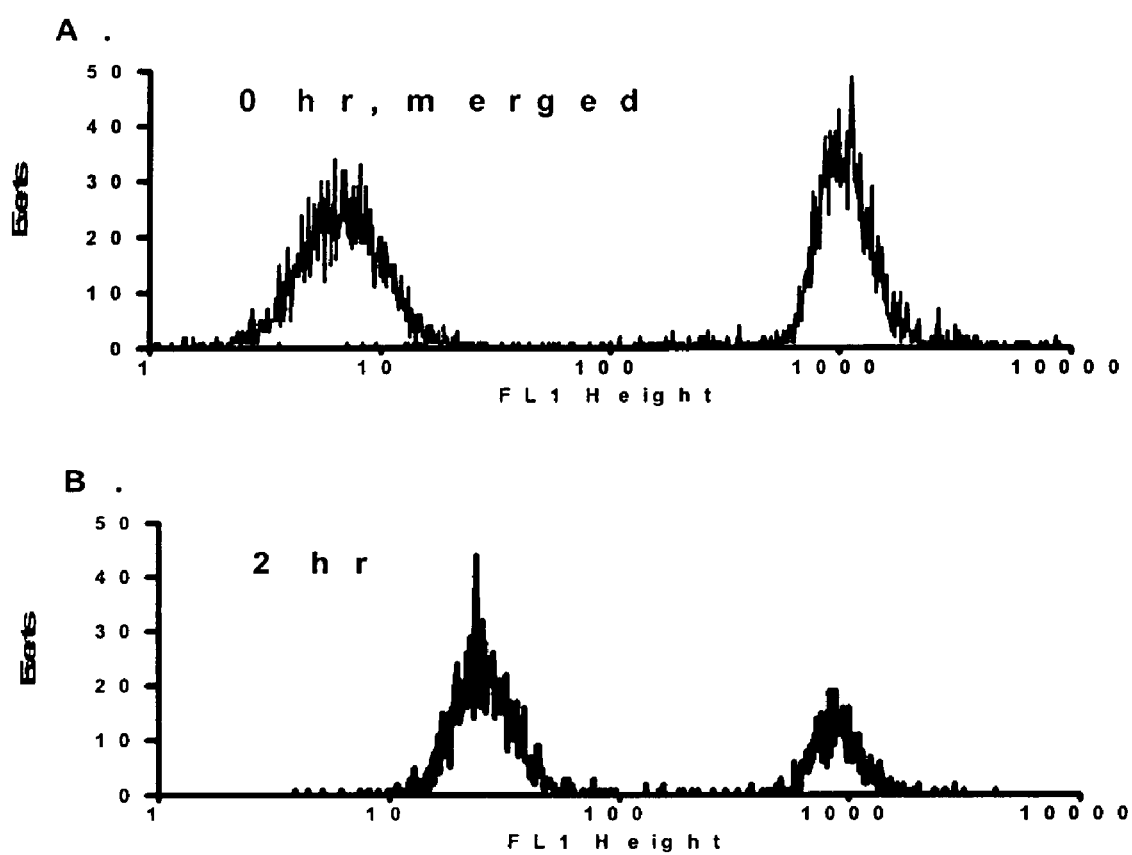
FIG. 20 shows that GST-GFP bead hopping using glutathione beads according to the present invention is slow. A. One set of GSH beads was coated with GST-GFP, while another was left uncoated. Histograms of these two bead sets are shown merged. B. The two sets of beads were mixed together for 2 hours, and a histogram of the mixture was obtained. About 8% of the GST-GFP was lost from the coated beads, with about 2% of the GST-GFP transferring to the uncoated beads. GST-Bcl proteins should also hop to other beads in a multiplex assay this slowly.

FIG. 19 shows that the assay can be performed in a competitive manner, with both unlabelled peptides or the small molecule inhibitor ABT737 as competitor. The binding constant of ABT737 obtained here, ~10 nM, is limited by the presence of about 20 nM GST-Bcl-XL in the assay, which is removed before a multiplex assay. This therefore agrees with a value of <1 nM obtained earlier (Oltersdorf et al., 2005). It is possible that the noncovalent GSH to GST interaction would allow a fraction of the GST-Bcl protein to dissociate from one set of beads during the assay, then bind again to the same beads or to other beads. To define the rate at which this happens, we first used GST-GFP on one set of beads and followed the transfer, or hopping, of this to another set of beads during mixing. In FIG. 20A, a histogram of uncoated GSH beads (left cluster) is shown merged with a histogram of GST-GFP coated beads (right cluster) at the start of the experiment. The coated beads were centrifuged, the supernatant and unbound GST-GFP were removed, the bead sets were mixed together. After two hours of mixing, another histogram was obtained (FIG. 20B). Analysis of this data shows that 8% of the GST-GFP had dissociated from the coated beads, and only 2% of the GST-GFP rebound to the uncoated beads. This transfer was unexpectedly slow; the reasons for this slow rate include rate theory for millions of sites on micrometer-sized particles, and GST dimerization (Tessema et al., 2006). The results suggest that no more than 10% of a signal on any bead in a six bead-type experiment might come from the other beads, a result confirmed below with GST-Bcl proteins in an automated, multiplexed experiment.

Figure 21:
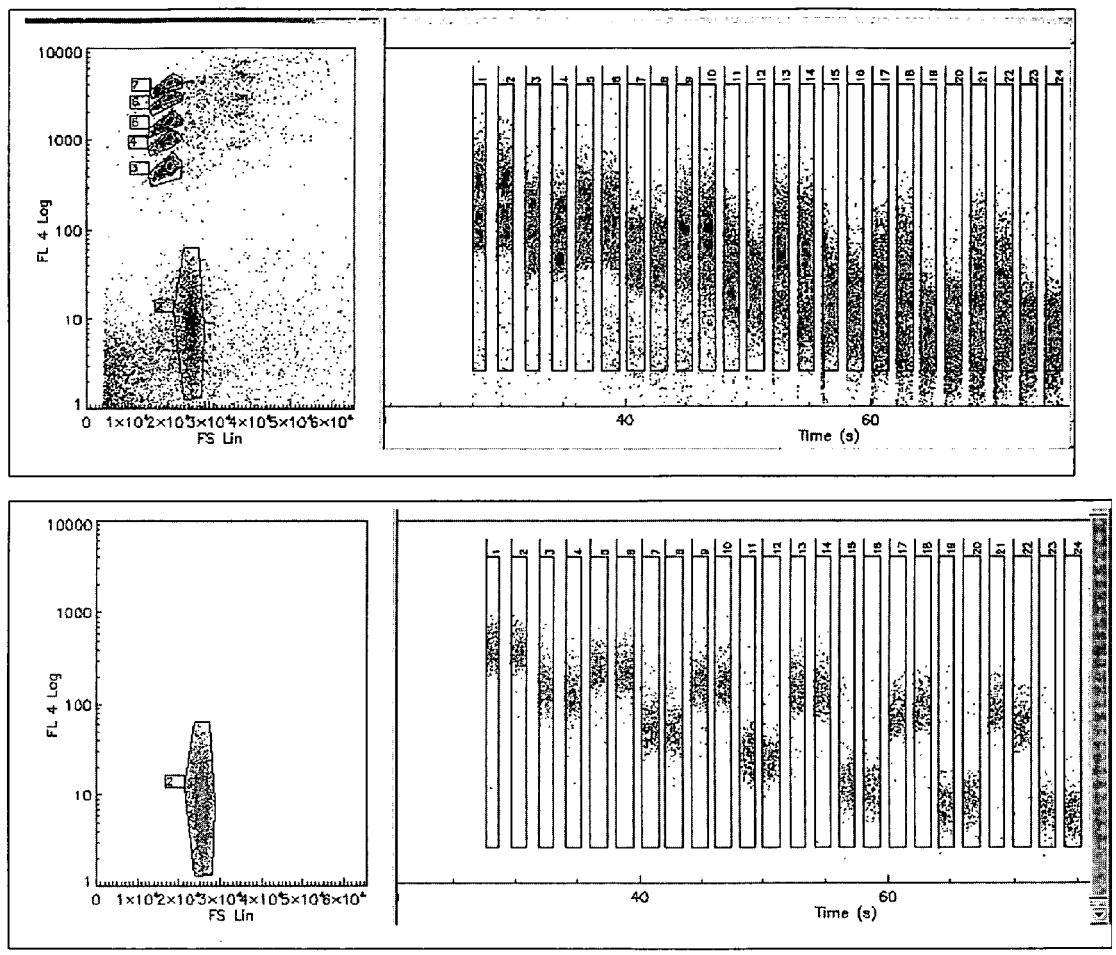
FIG. 21 shows plate based multiplex, automated assays. GSH beads with 6 levels of red address label (indicated by gates 2, 3, 4, 5, 6, 7) were bound individually to the six Bcl proteins, then resuspended in fresh buffer to perform binding and competition assays in 38 wells total. Upper left. A plot of forward scatter (X axis) versus log of address label (Y axis, FL4 log channel) shows six distinct sets. Upper Right. A plot of time (X axis) versus log of green fluorescence on beads (Y axis, FL1 log) is shown. Time bins have been automatically drawn by an in-house program around the clusters of beads, each cluster corresponding to one well, while the Y axis displays the amount of green F-Bim (FL1 log channel) shown by all six bead sets in that well. Lower left. The beads with the lowest level of address label (Bcl-XL) have been selected. Lower Right. The green fluorescence of F-Bim bound to the Bcl-XL on the selected beads is shown on a log scale. The data consist of pairs of wells showing total and nonspecific binding for a six point binding curve (high [F-Bim] first), followed by pairs of wells showing a seven point competition curve (low concentration of competitor first).

Binding and competition assays are multiplexed, read automatically using HyperCyt®, and data reduced using IDLQuery software. GSH bead sets with 6 levels of red address label (coated individually with the six anti-apoptotic Bcl-2 family members) were mixed and used to perform binding and competition assays in a total of 38 wells of a 384 well plate. In FIG. 21 we show the part of the readout from the IDLQuery program for this 1 minute data file. The upper left is a plot of forward scatter (X axis) versus log of the red address label (Y axis), and the six bead sets are clearly distinguished. The upper right is a plot of time (X axis) versus log of the green fluorescence (F-Bim) on the beads (Y axis); the data have been binned by the program automatically into clusters of beads, each cluster corresponding to a well in which all six bead sets are represented. The lower left shows how one bead set from panel the upper left has been selected, and the lower right shows the green F-Bim fluorescence on the selected bead set. The mean channel fluorescence (MCF) of each cluster is automatically computed and output to an EXCEL file.

Figure 22:
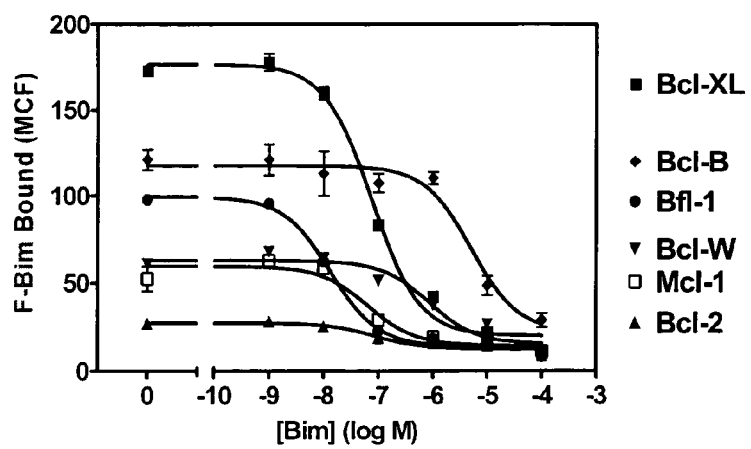
FIG. 22 shows Competition curves resulting from the sixplex analysis which is depicted in FIG. 21, above. The beads were coated with 100 nM Bcl-XL, Bcl-B and Bfl-1, limiting amounts of Bcl-W and Mcl-1, and denatured Bcl-2, showing the dynamic range of the assay. A wide range of specificities is observed, and the low signal given by the denatured Bcl-2-coated beads serves as an upper limit of how much GST-Bcl-protein has been transferred, from all the other beads combined, to the Bcl-2 set during the incubation.

Competition curves resulting from the sixplex are shown in FIG. 22. The beads were coated with 100 nM Bcl-XL, Bcl-B and Bfl-1, limiting amounts of Bcl-W and Mcl-1, and denatured Bcl-2, showing the dynamic range of the assay. A wide range of specificities is observed, and the low signal given by the denatured Bcl-2-coated beads serves as an upper limit of how much GST-Bcl-protein has been transferred, from all the other beads combined, to the Bcl-2 set during the incubation. The Cheng-Prusoff approximation was used to calculate $K_i$ values for unlabelled Bim peptide for each of the proteins, using the $K_d$ values for F-Bim obtained earlier and the $EC_{50}$ values for F-Bim displacement given in FIG. 6. All the proteins bound Bim with a $K_i$ of 10-40 nM except for Bcl-W, which displayed a $K_d$ of 140 nM, and Bcl-B, which displayed a $K_i$ of 1.4 µM. The addition of fluorescein to a peptide has the potential to impact its binding which may explain the results for Bcl-W and Bcl-B). Binding enhancement has been observed before in the formyl peptide receptor system (Vilven et al., 1998). This result should not impact our ability to screen the sixplex for active molecules in the small molecule repository.

Materials and Methods

Protein purification: GST-fusion proteins containing Bcl-XL, Bcl-2, Bcl-W, Bcl-B, Bfl-1 and Mcl-1 lacking their C-terminal transmembrane domains (~last 20 amino-acids) ("ΔTM") were expressed from pGEX 4T-1 plasmid in XL-1 Blue cells (Stratagene, Inc.). Briefly, cells were grown in 2 L of LB with 50 µg/mL ampicillin at 37° C. to an OD600 nm of 1.0., then IPTG (0.5 M) was added, and the cultures were incubated at 25° C. for 6 h. Cells were then recovered in 20 mM phosphate buffer (pH 7.4), 150 mM NaCl, 1 mM DTT, 1 mM EDTA, 1 mM, followed by sonication. Cellular debris were sedimented by centrifugation at 27,500 g for 20 min, and the resulting supernatants were incubated with 10 mL of glutathione-Sepharose (Pharmacia) at 4° C. for 2 h. The resin was washed 3 times with 20 mM phosphate buffer (pH 7.4), 150 mM NaCl, and 1 mM DTT, and then 10 mM of reduced glutathione dissolved in 50 mM Tris-HCl (pH 8.0) was used to elute the GST-fusion proteins.

HyperCyt® Assay

A multiplexed, homogeneous no-wash HyperCyt® assays for sensitive detection of compounds that block F-Bim (6 plex) and F-Bak (4 plex) binding to Bcl-2 family proteins was used. These assay use the peptides at a fixed concentration in a concentration range in the midrange of the $K_d$s for the binding to the whole family of Bcl-2 members.

Assay Protocol. The screen has been formatted for 384 well plates (Greiner #784101) for a total of 15 µl in each well. 384-well microplates are configured with 32 control wells (columns 1 and 24 for unblocked and receptor blocking controls, respectively) and 352 wells to which test compounds are added (columns 2-23). The competitor is added in 5 µl, the fluorescent peptide is added in 5 µl, and the coated beads are added in 5 µl. The buffer is an intracellular mimic, 30 mM HEPES, pH 7.5, 100 mM KCl, 20 mM NaCl, and also has 0.01% dodecyl maltoside and 0.1% bovine serum albumin to suppress nonspecific binding. The bead sets are coated by mixing each set individually in the presence of ±100 nM GST-Bcl protein with 5,000 beads per microliter for two hours, then centrifuging the beads and removing the unbound protein with the supernatant. The sets are resuspended together just before addition to the assay plate. The beads are kept suspended during the assay using an orbital shaker at 4° C. for two hours, then the plate is read at a cytometer at room temperature.

Important considerations in the assay implementation are as follows:

i) Solvent. Test compounds are stored as DMSO stocks. Peptides and proteins are stored in aqueous buffer. All are diluted in buffer so that final DMSO concentrations in test plates are between 0.5 and 1%, and well tolerated by the assay.

ii) Temperature. Reagents and coated beads are pre-chilled and maintained at 4° C. until automated reading at a cytometer, done at room temperature.

iii) Microsphere suspension. Best flow cytometry sampling and analysis results are obtained with uniform suspensions. To maintain uniform suspensions during the 2 hr incubations, microplates are placed on an orbital shaker in a refrigerator. HyperCyt® sampling of a 384-well plate is completed in 10 min.

iv) Microsphere concentration. A starting bead stock of $6 \times 10^6$ microsphere/ml ($10^6$/ml of each bead type) is diluted 1:3 in the final assay mixture (~$2 \times 10^6$ bead/ml, 15 µl total volume). This results in analysis of ~1,000 beads of each cell type from each well when sampling at 40 wells/min (aspirated sample volume ~2 µl; some losses occur). Higher bead concentrations (up to $2 \times 10^7$/ml final in wells) may be used, if desired.

v) Peptide concentration. To ensure maximal assay sensitivity and response, the fluorescent ligand peptide is used at a final concentration approximating 50 nM. In blocking control wells, unlabeled peptide is used at a 100× higher concentration (3 µM).

vi) Test compound concentration. Test compounds are typically screened at final concentrations of up to ~50 µM. This has permitted detection of compounds with Ki as high as ~50 µM.

vii) Automated data analysis. Immediately after data acquisition by the flow cytometer, proprietary software (IDLQuery, developed by Bruce Edwards and available at the NM MLSCN) is used analyze the data file. The program automatically detects the time-resolved data clusters (wells), ensures that there are 384, and analyzes each to determine the mean channel fluorescence (MCF) of bound peptide. These reduced data are automatically exported to a Microsoft Excel spreadsheet template that instantly calculates the assay quality control Z' factor and peptide binding inhibition percent for each well. Thus, comprehensive assay results are available within 1 to 2 min after assay plate sampling is completed. This provides ample opportunity to detect and correct any technical problems that may occur. Procedures have been implemented that enable rapid detection of errors such as an empty well or difficulties in resolving data clusters from adjoining wells (both relatively rare occurrences). Because each sample consists of 2 µl taken from a 15 µl volume in each well, we are able to sample and analyze each plate twice and average the results in the Excel spreadsheet.

Confirmatory Screen. After the primary screen, compounds that displayed activity are cherry picked and retested. This will identify false positives. Compounds that continue to display activity will be assessed for binding affinity by carrying out dose-response assays between 1 nM and 100 µM. In the multiplexed format, the confirmatory screen will also provide information regarding specificity and selectivity.

Secondary Assays. Secondary assays are performed in engineered stably transfected human cell lines which express Bcl-2 family members using a tetracycline-inducible promoter systems. In these cells, turning on expression of anti-apoptotic Bcl-2-family member Bcl-XL was shown to protect against apoptosis induced by cytotoxic anticancer drugs such as doxorubicin (Wang, 2004). Addition of Bcl-XL neutralizing compounds overcomes this protection. This assay can be used accordingly with compounds identified using the flow cytometry method of the present invention.

Chemical optimization. Following the complete characterization of the original hit compounds, they compounds are assessed in collaboration with chemists for their potential for further development. Where suitable, a large range of analogues are generated and tested in binding and biological assays, thus exploring the structure-activity relationship.

REFERENCES

Glutathione Conjugated Beads

1. Wu G, Fang Y Z, Yang S, Lupton J R, Turner N D. Glutathione metabolism and its implications for health. J Nutr 2004; 134(3):489-92.
2. Djordjevic V B. Free radicals in cell biology. Int Rev Cytol 2004; 237:57-89.
3. Cook J A, Gius D, Wink D A, Krishna M C, Russo A, Mitchell J B. Oxidative stress, redox, and the tumor microenvironment. Semin Radiat Oncol 2004; 14(3):259-66.
4. Liu H, Wang H, Shenvi S, Hagen T M, Liu R M. Glutathione metabolism during aging and in Alzheimer disease. Ann N Y Acad Sci 2004; 1019:346-9.
5. Fonnum F, Lock E A. The contributions of excitotoxicity, glutathione depletion and DNA repair in chemically induced injury to neurones: exemplified with toxic effects on cerebellar granule cells. J Neurochem 2004; 88(3):513-31.
6. Simons P C, Vander Jagt D L. Purification of glutathione S-transferases from human liver by glutathione-affinity chromatography. Anal Biochem 1977; 82(2):334-41.
7. Vikis H G, Guan K L. Glutathione-S-transferase-fusion based assays for studying protein-protein interactions. Methods Mol Biol 2004; 261:175-86.
8. Simons P C, Biggs S M, Waller A, Foutz T, Cimino D F, Guo Q, Neubig R R, Tang W J, Prossnitz E R, Sklar L A. Real-time analysis of ternary complex on particles: direct evidence for partial agonism at the agonist-receptor-G protein complex assembly step of signal transduction. J Biol Chem 2004; 279(14):13514-21.
9. Simons P C, Shi M, Foutz T, Cimino D F, Lewis J, Buranda T, Lim W K, Neubig R R, McIntire W E, Garrison J and others. Ligand-receptor-G-protein molecular assemblies on beads for mechanistic studies and screening by flow cytometry. Mol Pharmacol 2003; 64(5):1227-38.
10. Goldstein B, Posner R G, Torney D C, Erickson J, Holowka D, Baird B. Competition between solution and cell surface receptors for ligand. Dissociation of hapten bound to surface antibody in the presence of solution antibody. Biophys J 1989; 56(5):955-66.
11. Hiraku Y, Murata M, Kawanishi S. Determination of intracellular glutathione and thiols by high performance liquid chromatography with a gold electrode at the femtomole level: comparison with a spectroscopic assay. Biochim Biophys Acta 2002; 1570(1):47-52.
12. Zacharias D A, Violin J D, Newton A C, Tsien R Y. Partitioning of lipid-modified monomeric GFPs into membrane microdomains of live cells. Science 2002; 296:913-916.
13. Baer K, Al-Hasani H, Corona T, Rufer A, Nolle V, Bergschneider E, Klein H W. Dimerization-induced activation of soluble insulin/IGF-1 receptor kinases: an alternative mechanism of activation. Biochem 2001; 40:14268-78.
14. Jencks W P. On the attribution and additivity of binding energies. Proc Nat Acad Sci USA 1981; 78:4046-50.
15. Kaufman E N, Jain, R K. Effect of bivalent interaction upon apparent antibody affinity: Experimental confirmation of theory using fluorescence photobleaching and implications for antibody binding assays. Cancer Res 1992; 52:4157-67.

REFERENCES

GTPases-RAS and Ras-Related

1. Bucci C Chiariello M Signal transduction grabs attention. Cell Signal 18:1-8, 2006
2. Gomez GA Daniotti J L H-ras dynamically interacts with recycling endosomes in cho-k1 cells: Involvement of rab5 and rab11 in the trafficking of h-ras to this pericentriolar endocytic compartment. J Biol Chem 280:34997-35010, 2005
3. Holly S P, Larson M K and Parise L V The unique n-terminus of r-ras is required for rac activation and precise regulation of cell migration. Mol Biol Cell 16:2458-2469, 2005
4. Ehrenreiter K, Piazzolla D, Velamoor V, Sobczak I, Small J V, Takeda J, Leung T and Baccarini M Raf-1 regulates rho signaling and cell migration. J Cell Biol 168:955-964, 2005
5. Takai Y, Sasaki T and Matozaki T Small gtp-binding proteins. Physiol Rev 81:153-208, 2001
6. Wennerberg K, Rossman K L and Der C J The ras superfamily at a glance. J Cell Sci 118:843-846, 2005
7. Kahn R A, Cherfils J, Elias M, Lovering R C, Munro S and Schurmann A Nomenclature for the human art family of gtp-binding proteins: Arf, arl, and sar proteins. J Cell Biol 172:645-650, 2006
8. Farnsworth C L, Marshall M S, Gibbs J B, Stacey D W and Feig L A Preferential inhibition of the oncogenic form of rash by mutations in the gap binding/"effector" domain. Cell 64:625-633, 1991
9. Sukumar S, Notario V, Martin-Zanca D and Barbacid M Induction of mammary carcinomas in rats by nitroso-methylurea involves malignant activation of h-ras-1 locus by single point mutations. Nature 306:658-661, 1983
10. Taparowsky E, Suard Y, Fasano O, Shimizu K, Goldfarb M and Wigler M Activation of the t24 bladder carcinoma transforming gene is linked to a single amino acid change. Nature 300:762-765, 1982
11. Boylan J F, Jackson J, Steiner M R, Shih T Y, Duigou G J, Roszman T, Fisher P B and Zimmer S G Role of the ha-ras (rash) oncogene in mediating progression of the tumor cell phenotype (review). Anticancer Res 10:717-724, 1990
12. Hruban R H, van Mansfeld A D, Offerhaus G J, van Weering D H, Allison D C, Goodman S N, Kensler T W, Bose K K, Cameron J L and Bos J L K-ras oncogene activation in adenocarcinoma of the human pancreas. A study of 82 carcinomas using a combination of mutant-enriched polymerase chain reaction analysis and allele-specific oligonucleotide hybridization. Am J Pathol 143:545-554, 1993
13. Abrams S I, Hand P H, Tsang K Y and Schlom J Mutant ras epitopes as targets for cancer vaccines. Semin Oncol 23:118-134, 1996
14. Houlden H, King R H, Muddle J R, Warner T T, Reilly M M, Orrell R W and Ginsberg L A novel rab7 mutation associated with ulcero-mutilating neuropathy. Ann Neurol 56:586-590, 2004
15. Verhoeven K, De Jonghe P, Coen K, Verpoorten N, Auer-Grumbach M, Kwon J M, Fitzpatrick D, Schmedding E, De Vriendt E, Jacobs A, Van Gerwen V, Wagner K, Hartung H P and Timmerman V Mutations in the small gtp-ase late endosomal protein rab7 cause charcot-marie-tooth type 2b neuropathy. Am J Hum Genet. 72:722-727, 2003
16. Williams D A, Tao W, Yang F, Kim C, Gu Y, Mansfield P, Levine J E, Petryniak B, Derrow C W, Harris C, Jia B, Zheng Y, Ambruso DR, Lowe J B, Atkinson S J, Dinauer M C and Boxer L Dominant negative mutation of the hematopoietic-specific rho gtpase, rac2, is associated with a human phagocyte immunodeficiency. *Blood* 96:1646-1654, 2000
17. BAHADORAN P, BUSCA R, CHIAVERINI C, WESTBROEK W, LAMBERT J, BILLE K, VALONY G, FUKUDA M, NAEYAERT J M, ORTONNE J P and BALLOTTI R Characterization of the molecular defects in rab27a, caused by rab27a missense mutations found in patients with griscelli syndrome. *J Biol Chem* 278:11386-11392, 2003
18. MORGILLO FLEE H Y Lonafarnib in cancer therapy. *Expert Opin Investig Drugs* 15:709-719, 2006
19. RUSSELL R G Bisphosphonates: From bench to bedside. *Ann N Y Acad Sci* 1068:367-401, 2006
20. PARK H J, KONG D, IRUELA-ARISPE L, BEGLEY U, TANG D and GALPER J B 3-hydroxy-3-methylglutaryl coenzyme a reductase inhibitors interfere with angiogenesis by inhibiting the geranylgeranylation of rhoa. *Circ Res* 91:143-150, 2002
21. GAO Y, DICKERSON J B, GUO F, ZHENG J and ZHENG Y Rational design and characterization of a rac gtpase-specific small molecule inhibitor. *Proc Natl Acad Sci USA* 101:7618-7623, 2004
22. NASSAR N, CANCELAS J, ZHENG J, WILLIAMS D A and ZHENG Y Structure-function based design of small molecule inhibitors targeting rho family gtpases. *Curr Top Med Chem* 6:1109-1116, 2006
23. NOLAN JPSKLAR L A The emergence of flow cytometry for sensitive, real-time measurements of molecular interactions. *Nat Biotechnol* 16:633-638, 1998
24. DE ROSA S C, BRENCHLEY J M and ROEDERER M Beyond six colors: A new era in flow cytometry. *Nat Med* 9:112-117, 2003
25. KUCKUCK F W, EDWARDS B S and SKLAR L A High throughput flow cytometry. *Cytometry* 44:83-90, 2001
26. TESSEMA M, SIMONS P C, CIMINO D F, SANCHEZ L, WALLER A, POSNER R G, WANDINGER-NESS A, PROSSNITZ E R and SKLAR L A Glutathiones-transferase-green fluorescent protein fusion protein reveals slow dissociation from high site density beads and measures free gsh. *Cytometry A* 69:326-334, 2006
27. SHY M E Charcot-marie-tooth disease: An update. *Curr Opin Neurol* 17:579-585, 2004
28. RAK A, PYLYPENKO O, NICULAE A, PYATKOV K, GOODY R S and ALEXANDROV K Structure of the rab7:Rep-1 complex: Insights into the mechanism of rab prenylation and choroideremia disease. *Cell* 117:749-760, 2004
29. JORDENS I, FERNANDEZ-BORJA M, MARSMAN M, DUSSELJEE S, JANSSEN L, CALAFAT J, JANSSEN H, WUBBOLTS R and NEEFJES J The rab7 effector protein rilp controls lysosomal transport by inducing the recruitment of dynein-dynactin motors. *Curr Biol* 11:1680-1685, 2001
30. ZHANG J, BERENSTEIN E H, EVANS R P and SIRAGANIAN R P Transfection of syk protein tyrosine kinase reconstitutes high affinity ige receptor-mediated degranulation in a syk-negative variant of rat basophilic leukemia rbl-2h3 cells. *J Exp Med* 184:71-79, 1996
31. GRAHAM T E, PFEIFFER J R, LEE R J, KUSEWITT D F, MARTINEZ A M, FOUTZ T, WILSON B S and OLIVER J M Mek and erk activation in ras-disabled rbl-2h3 mast cells and novel roles for geranylgeranylated and farnesylated proteins in fc epsilonri-mediated signaling. *J Immunol* 161:6733-6744, 1998
32. BAR-SAGI DHALL A Ras and rho gtpases: A family reunion. *Cell* 103:227-238, 2000
33. DE ROOIJ JBOS J L Minimal ras-binding domain of raf1 can be used as an activation-specific probe for ras. *Oncogene* 14:623-625, 1997
34. BLUMER KJJOHNSON G L Diversity in function and regulation of map kinase pathways. *Trends Biochem Sci* 19:236-240, 1994
35. BOULTON T G, YANCOPOULOS G D, GREGORY J S, SLAUGHTER C, MOOMAW C, HSU J and COBB M H An insulin-stimulated protein kinase similar to yeast kinases involved in cell cycle control. *Science* 249:64-67, 1990
36. TRAYNOR-KAPLAN A E, THOMPSON B L, HARRIS A L, TAYLOR P, OMANN G M and SKLAR L A Transient increase in phosphatidylinositol 3,4-bisphosphate and phosphatidylinositol trisphosphate during activation of human neutrophils. *J Biol Chem* 264:15668-15673, 1989
37. AUBRY J P, BLAECKE A, LECOANET-HENCHOZ S, JEANNIN P, HERBAULT N, CARON G, MOINE V and BONNEFOY J Y Annexin v used for measuring apoptosis in the early events of cellular cytotoxicity. *Cytometry* 37:197-204, 1999
38. HOTCHIN NAHALL A Regulation of the actin cytoskeleton, integrins and cell growth by the rho family of small gtpases. *Cancer Surv* 27:311-322, 1996
39. BOKOCH G M Regulation of innate immunity by rho gtpases. *Trends Cell Biol* 15:163-171, 2005
40. RIDLEY A J, ALLEN W E, PEPPELENBOSCH M and JONES G E Rho family proteins and cell migration. *Biochem Soc Symp* 65:111-123, 1999
41. WITTMANN T, BOKOCH G M and WATERMAN-STORER C M Regulation of microtubule destabilizing activity of op18/stathmin downstream of rac1. *J Biol Chem* 279:6196-6203, 2004
42. WITTMANN TWATERMAN-STORER C M Spatial regulation of clasp affinity for microtubules by rac1 and gsk3beta in migrating epithelial cells. *J Cell Biol* 169:929-939, 2005
43. BOKOCH GMDIEBOLD B A Current molecular models for nadph oxidase regulation by rac gtpase. *Blood* 100:2692-2696, 2002
44. DIEBOLD BABOKOCH G M Rho gtpases and the control of the oxidative burst in polymorphonuclear leukocytes. *Curr Top Microbiol Immunol* 291:91-111, 2005
45. BENARD V, BOKOCH G M and DIEBOLD B A Potential drug targets: Small gtpases that regulate leukocyte function. *Trends Pharmacol Sci* 20:365-370, 1999
46. FRITZ GKAINA B Rho gtpases: Promising cellular targets for novel anticancer drugs. *Curr Cancer Drug Targets* 6:1-14, 2006
47. WITTMANN T, BOKOCH G M and WATERMAN-STORER C M Regulation of leading edge microtubule and actin dynamics downstream of rac1. *J Cell Biol* 161:845-851, 2003
48. EDWARDS D C, SANDERS L C, BOKOCH G M and GILL G N Activation of lim-kinase by pak1 couples rac/cdc42 gtpase signalling to actin cytoskeletal dynamics. *Nat Cell Biol* 1:253-259, 1999
49. HUANG T Y, DERMARDIROSSIAN C and BOKOCH G M Cofilin phosphatases and regulation of actin dynamics. *Curr Opin Cell Biol* 18:26-31, 2006
50. ZHAO T, BENARD V, BOHL B P and BOKOCH G M The molecular basis for adhesion-mediated suppression of reactive oxygen species generation by human neutrophils. *J Clin Invest* 112:1732-1740, 2003
51. HEYWORTH P G, KNAUS U G, XU X, UHLINGER D J, CONROY L, BOKOCH G M and CURNUTTE J T Requirement for posttranslational processing of rac gtp-binding proteins for activation of human neutrophil nadph oxidase. *Mol Biol Cell* 4:261-269, 1993
52. STEIN M P, DONG J and WANDINGER-NESS A Rab proteins and endocytic trafficking: Potential targets for therapeutic intervention. *Adv Drug Deliv Rev* 55:1421-1437, 2003
53. PFEFFER S A model for rab gtpase localization. *Biochem Soc Trans* 33:627-630, 2005

54. BUCCI C, WANDINGER-NESS A, LUTCKE A, CHIARIELLO M, BRUNI C B and ZERIAL M Rab5a is a common component of the apical and basolateral endocytic machinery in polarized epithelial cells. *Proc Natl Acad Sci USA* 91:5061-5065, 1994

55. FENG Y, PRESS B and WANDINGER-NESS A Rab 7: An important regulator of late endocytic membrane traffic. *J Cell Biol* 131:1435-1452, 1995

56. PRESS B, FENG Y, HOFLACK B and WANDINGER-NESS A Mutant rab7 causes the accumulation of cathepsin d and cation-independent mannose 6-phosphate receptor in an early endocytic compartment. *J Cell Biol* 140:1075-1089, 1998

57. CHEN W, FENG Y, CHEN D and WANDINGER-NESS A Rab11 is required for trans-golgi network-to-plasma membrane transport and a preferential target for gdp dissociation inhibitor. *Mol Biol Cell* 9:3241-3257, 1998

58. CHEN W WANDINGER-NESS A Expression and functional analyses of rab8 and rab11a in exocytic transport from trans-golgi network. *Methods Enzymol* 329:165-175, 2001

59. FENG Y, PRESS B, CHEN W, ZIMMERMAN J and WANDINGER-NESS A Expression and properties of rab7 in endosome function. *Methods Enzymol* 329:175-187, 2001

60. STEIN M P, FENG Y, COOPER K L, WELFORD A M and WANDINGER-NESS A Human vps34 and p150 are rab7 interacting partners. *Traffic* 4:754-771, 2003

61. DONG J, CHEN W, WELFORD A and WANDINGER-NESS A The proteasome alpha-subunit xapc7 interacts specifically with rab7 and late endosomes. *J Biol Chem* 279:21334-21342, 2004

62. LI Y, WANDINGER-NESS A, GOLDENRING J R and COVER T L Clustering and redistribution of late endocytic compartments in response to *helicobacter pylori* vacuolating toxin. *Mol Biol Cell* 15:1946-1959, 2004

63. DERETIC D, PULEO-SCHEPPKE B and TRIPPE C Cytoplasmic domain of rhodopsin is essential for post-golgi vesicle formation in a retinal cell-free system. *J Biol Chem* 271:2279-2286, 1996

64. DERETIC D Rab proteins and post-golgi trafficking of rhodopsin in photoreceptor cells. *Electrophoresis* 18:2537-2541, 1997

65. MORITZ O L, TAM B M, HURD L L, PERANEN J, DERETIC D and PAPERMASTER D S Mutant rab8 impairs docking and fusion of rhodopsin-bearing post-golgi membranes and causes cell death of transgenic xenopus rods. *Mol Biol Cell* 12:2341-2351, 2001

66. CHUA J, VERGNE I, MASTER S and DERETIC V A tale of two lipids: *Mycobacterium tuberculosis* phagosome maturation arrest. *Curr Opin Microbiol* 7:71-77, 2004

67. DERETIC V, VIA L E, FRATTI R A and DERETIC D Mycobacterial phagosome maturation, rab proteins, and intracellular trafficking. *Electrophoresis* 18:2542-2547, 1997

68. VIA L E, DERETIC D, ULMER R J, HIBLER N S, HUBER L A and DERETIC V Arrest of mycobacterial phagosome maturation is caused by a block in vesicle fusion between stages controlled by rab5 and rab7. *J Biol Chem* 272:13326-13331, 1997

69. VERGNE I, CHUA J, SINGH S B and DERETIC V Cell biology of mycobacterium tuberculosis phagosome. *Annu Rev Cell Dev Biol* 20:367-394, 2004

70. DERETIC V, SINGH S, MASTER S, HARRIS J, ROBERTS E, KYEI G, DAVIS A, DE HARO S, NAYLOR J, LEE H H and VERGNE I *Mycobacterium tuberculosis* inhibition of phagolysosome biogenesis and autophagy as a host defence mechanism. *Cell Microbiol* 8:719-727, 2006

71. REZAIE T, CHILD A, HITCHINGS R, BRICE G, MILLER L, COCA-PRADOS M, HEON E, KRUPIN T, RITCH R, KREUTZER D, CRICK R P and SARFARAZI M Adult-onset primary open-angle glaucoma caused by mutations in optineurin. *Science* 295:1077-1079, 2002

72. SARFARAZI MREZAIE T Optineurin in primary open angle glaucoma. *Opthalmol Clin North Am* 16:529-541, 2003

73. MUKHERJEE S, DONG J, HEINCELMAN C, LENHART M, WELFORD A and WANDINGER-NESS A Functional analyses and interaction of the xapc7 proteasome subunit with rab7. *Methods Enzymol* 403:650-663, 2005

74. STEIN M P, CAO C, TESSEMA M, FENG Y, ROMERO E, WELFORD A and WANDINGER-NESS A Interaction and functional analyses of human vps34/p150 phosphatidylinositol 3-kinase complex with rab7. *Methods Enzymol* 403:628-649, 2005

REFERENCES

Bcl-2 Family Proteins

Becattini B, Kitada S, Leone M, Monosov E, Chandler S, Zhai D, Kipps T J, Reed J C, and Pellecchia M (2004). Rational design and real time in-cell detection of the pro-apoptotic activity of a novel compound targeting Bcl-Xl. *Chem Biol* 11: 389-395.

De Rosa S C, Brenchley J M and Roederer M (2003). Beyond six colors: a new era in flow cytometry. Nat Med 9: 112-117, Edwards B S, Kuckuck F, and Sklar L A. Plug flow cytometry: An automated coupling device for rapid sequential flow cytometric sample analysis. *Cytometry* 37: 156-159, 1999.

Edwards B S, Kuckuck F W, Prossnitz E R, Okun A, Ransom J T and Sklar L A (2001). Plug flow cytometry extends analytical capabilities in cell adhesion and receptor pharmacology. *Cytometry* 43: 211-216.

Edwards B S, Kuckuck F W, Prossnitz E R, Ransom J T and Sklar L A (2001). HTPS flow cytometry: a novel platform for automated high throughput drug discovery and characterization. *J Biomol Screen* 6: 83-90.

Holinger E P, Chittendon T, and Lutz R J (1999). Bak BH3 peptides antagonize Bcl-XL function and induce apoptosis through cytochrome c-independent activation of caspases. *J. Biol. Chem.* 274: 13298-13304.

Kuckuck F W, Edwards B S and Sklar L A. High throughput flow cytometry (2001). *Cytometry* 44: 83-90.

Leone M, Zhai D, Sareth S, Kitada S, Reed JC, and Pellecchia M (2003). Cancer prevention by tea polyphenols is linked to their direct inhibition of anti-apoptotic Bcl-2 family proteins. *Cancer Res* 63: 8118-8121.

Nolan J P and Sklar L A (1998). The emergence of flow cytometry for the sensitive, real-time analysis of molecular assembly. *Nature Biotechnology* 16: 833-838.

Oltersdorf T, Elmore S W, Shoemaker A R, Armstrong R C, Augeri D J, Belli B A, Bruncko, M, Deckwerth, T. L, Dinges J, Hajduk, P J, et al. (2005). An inhibitor of Bcl-2 family proteins induces regression of solid tumours. *Nature* 435, 677-681.

Palmer A E, Jin C, Reed J C, and Tsien R Y (2004). Bcl-2-mediated alterations in endoplasmic reticulum Ca2+ analyzed with an improved genetically encoded fluorescent sensor. *Proc Natl Acad Sci USA* 101, 17404-17409.

Ramirez S, Aiken C T, Andrzejewski B, Sklar L A and Edwards B S (2003). High-throughput flow cytometry: validation in microvolume bioassays. *Cytometry A* 53: 55-65.

Reed J C, Doctor K S, and Godzik A (2004). The domains of apoptosis: a genomics perspective. *Sci STKE* 2004, re9.

Reed J C, and Pellecchia M (2005). Apoptosis-based therapies for hematologic malignancies. *Blood* 106, 408-418.

Tessema M, Simons P C, Cimino D F, Sanchez L, Waller A, Posner R G, Wandinger-Ness A, Prossnitz E R, and Sklar L A (2006). Glutathione-S-transferase-GFP fusion protein reveals slow dissociation from high site density beads and measures free GSH. *Cytometry Part A* 69A: 326-334.

Vilven J C, Domalewski M, Prossnitz E R, Ye R D, Muthukumaraswamy N, Harris R B, Freer R J, and Sklar L A (1998). Strategies for positioning fluorescent probes and crosslinkers on formyl peptide ligands. *J Recept Signal Transuct Res* 18: 187-221.

Walensky L D, Kung A L, Escher I, Malia T J, Barbuto S, Wright R D, Wagner G, Verdine G L, and Korsmeyer S J (2004). Activation of apoptosis in vivo by a hydrocarbon-stapled BH3 helix. *Science* 305: 1466-1470.

Wang Z, Cuddy M, Samuel T, Welsh K, Schimmer A, Hanaii F, Houghten R, Pinilla C, and Reed J C (2004). Cellular, biochemical, and genetic analysis of mechanism of small molecule IAP inhibitors. *J Biol Chem* 279, 48168-48176.

Wang J-L, Zhang Z-J, Choksi S, Shan S, Lu Z, Croce C M, Alnemri E S, Korngold R and Huang Z (2000). Cell-permeable Bcl-2 binding peptides: A chemical approach to apoptosis induction in tumor cells. *Cancer Res.* 60: 1498-1502.

Zhai D, Ke N, Zhang H, Ladror U, Joseph M, Eichinger A, Godzik A, Ng S C, and Reed J C (2003). Characterization of the anti-apoptotic mechanism of Bcl-B. *Biochem J* 376, 229-236.

Zhai D, Jin C, Satterwait A C, and Reed J C (2006). Comparison of the chemical inhibitors of antiapoptotic Bcl-2 family proteins. *Cell Death & Diff.* (in press).

---

The invention claimed is:

1. A high site density glutathione derivatized flow cytometer bead comprising glutathione molecules covalently linked through a crosslinking agent to a polymeric bead, said bead having a diameter ranging from about 1 microns to about 30 microns, said bead having a high site binding density.

2. The derivatized flow cytometer bead according to claim 1 wherein said binding site density of said bead ranges from about $7.5 \times 10^3$ binding sites/$\mu m^2$ to about $5 \times 10^5$ binding sites/$\mu m^2$.

3. The derivatized flow cytometer bead according to claim 1 wherein said binding site density of said bead ranges from about $1 \times 10^4$ binding sites/$\mu m^2$ to about $1 \times 10^5$ binding sites/$\mu m^2$.

4. The derivatized flow cytomer bead according to claim 1 wherein said binding site density of said bead ranges from about $1 \times 10^4$ binding sites/$\mu m^2$ to about $5 \times 10^4$ binding sites/$\mu m^2$.

5. The derivatized flow cytometer bead according to claim 1 wherein said crosslinking agent is linked to said polymeric bead through a hydroxyl group or an amine group on said polymer bead.

6. The derivatized flow cytometer bead according to claim 1 wherein said crosslinking agent has two electrophilic groups or an electrophilic group and a nucleophilic group.

7. The derivatized flow cytometer bead according to claim 6 wherein said crosslinking agent has two electrophilic groups.

8. The derivatized flow cytometer bead according to claim 1 wherein said crosslinking agent is a bis-epoxide crosslinking agent.

9. The derivatived flow cytometer bead according to claim 7 wherein said crosslinking agent is 1,4-butanediyl diglyciyl ether.

10. The derivatized flow cytometer bead according to claim 7 wherein said crosslinking agent is succinimidyl-4-(N-maleimidomethyl)cyclohexane-1-carboxylate (SMCC) or sulfosuccinimidyl-4-(N-maleimidomethyl)cyclohexane-1-carboxylate (Sulfo-SMCC).

11. The derivatized flow cytometer bead according to claim 7 wherein said crosslinking agent is SMCC.

12. The derivatized flow cytometer bead having a diameter of about 3 microns to about 10 microns.

13. The derivatized flow cytometer bead wherein said polymeric bead comprises a polymeric material selected from the group consisting of amino-polystyrene, latex, polycarbohydrate and glass.

14. The derivatized flow cytometer bead according to claim 1 wherein said polymeric bead comprises a crosslinked agarose-dextran composite (Superdex).

15. The derivatized flow cytometer bead according to claim 13 wherein said polymeric material is amino-polystyrene.

16. The derivatized flow cytometer bead according to claim 1 further comprising a GST-fusion protein bound thereto.

17. The derivatized flow cytometer bead according to claim 16 wherein said GST fusion protein comprises GST and a fused protein.

18. The derivatized flow cytometer bead according to claim 17 wherein said fused protein is Bcl-2 protein.

19. The derivatized flow cytometer bead according to claim 17 wherein said fused protein is bound to a binding partner of said protein.

20. The derivatized flow cytometer bead according to claim 17 wherein said binding partner is a protein, peptide, DNA, RNA or a small molecule.

21. The derivatized flow cytometer bead according to claim 17 wherein said fused protein is a Bcl-2 protein.

22. The derivatized flow cytometer bead according to claim 21 wherein said Bcl-2 protein is Bcl-2, Bcl-XL, Bfl-1, Mcl-1, Bcl-W or Bcl-B.

23. The derivatized flow cytometer bead according to claim 19 wherein said fused protein is a Bcl-2 protein.

24. The derivatized flow cytometer bead according to claim 23 wherein said fused protein is Bcl-2, Bcl-XL, Bfl-1, Mcl-1, Bcl-W or Bcl-B.

25. The derivatized flow cytometer bead according to claim 19 wherein said binding partner is fluorescently labeled.

26. The derivatized flow cytometer bead according to claim 25 wherein said binding partner is a fluorescently labeled peptide.

27. The derivatized flow cytometer bead according to claim 26 wherein said peptide is a BH3 peptide based upon sequences found in Bcl-2 proteins.

28. The derivatized flow cytometer bead according to claim 27 wherein said peptide is a Bim BH3 peptide.

29. The derivatized flow cytometer bead according to claim 27 wherein said peptide is a Bid BH3 peptide.

30. The derivatized flow cytometer bead according to claim 27 wherein said peptide is a PUMA BH3 peptide.

31. The derivatized flow cytometer bead according to claim 27 wherein said peptide is a Bak BH3 peptide.

32. The derivatized flow cytometer bead according to claim 19 where said fused protein is a Bcl-2 protein and said binding partner is FITC conjugated epigallocachechin (ECGC).

33. The derivatized flow cytometer bead according to claim 19 wherein said fused protein is a GTPase.

34. The derivatized flow cytometer bead according to claim 33 wherein said GTPase is a Rab, Rac, Rho, Cdc42 or Ras GTPase.

35. The derivatized flow cytometer bead according to claim 34 wherein said binding partner is GTP.

36. The derivatized flow cytometer bead according to claim 34 wherein said GTPase is a Rab GTPase.

37. The derivatized flow cytometer bead according to claim 36 wherein said binding partner is HVps150, hVps34 or a myotubularin.

* * * * *